(12) United States Patent
D'Addio et al.

(10) Patent No.: US 10,682,391 B2
(45) Date of Patent: Jun. 16, 2020

(54) INHIBITORS OF IGFBP3 BINDING TO TMEM219 FOR TREATMENT OF INTESTINAL DISEASES

(71) Applicant: OSPEDALE SAN RAFFAELE SRL, Milan (IT)

(72) Inventors: Francesca D'Addio, Milan (IT); Paolo Fiorina, Milan (IT)

(73) Assignee: Ospedale San Raffaele SRL, Milan (IT)

( * ) Notice: Subject to any disclaimer, the term of this patent is extended or adjusted under 35 U.S.C. 154(b) by 0 days.

(21) Appl. No.: 15/579,573

(22) PCT Filed: Jun. 6, 2016

(86) PCT No.: PCT/EP2016/062790
§ 371 (c)(1),
(2) Date: Dec. 4, 2017

(87) PCT Pub. No.: WO2016/193496
PCT Pub. Date: Dec. 8, 2016

(65) Prior Publication Data
US 2018/0172708 A1 Jun. 21, 2018

(30) Foreign Application Priority Data
Jun. 4, 2015 (EP) .................................... 15170679

(51) Int. Cl.
| A61K 38/17 | (2006.01) |
| C07K 16/18 | (2006.01) |
| A61K 45/06 | (2006.01) |
| G01N 33/68 | (2006.01) |

(52) U.S. Cl.
CPC ........ *A61K 38/177* (2013.01); *A61K 38/1709* (2013.01); *A61K 45/06* (2013.01); *C07K 16/18* (2013.01); *C07K 2317/76* (2013.01); *G01N 33/6893* (2013.01); *G01N 2333/4745* (2013.01); *G01N 2800/06* (2013.01); *G01N 2800/065* (2013.01)

(58) Field of Classification Search
None
See application file for complete search history.

(56) References Cited

U.S. PATENT DOCUMENTS

| 3,773,919 A | 11/1973 | Boswell et al. |
| 5,215,534 A | 6/1993 | De Harde et al. |
| 6,066,464 A | 5/2000 | Khosravi et al. |
| 6,602,684 B1 | 8/2003 | Umana et al. |
| 7,083,784 B2 | 8/2006 | Dall'Acqua et al. |
| 7,521,541 B2 | 4/2009 | Eigenbrot et al. |
| 8,323,962 B2 | 12/2012 | Dall'Acqua et al. |
| 9,248,242 B2 | 2/2016 | Verespej et al. |
| 9,427,531 B2 | 8/2016 | Hourmand et al. |
| 9,566,395 B2 | 2/2017 | Denny et al. |
| 2003/0157108 A1 | 8/2003 | Presta |
| 2004/0093621 A1 | 5/2004 | Shitara et al. |
| 2004/0132028 A1 | 7/2004 | Stumpp et al. |
| 2005/0123546 A1 | 6/2005 | Umana et al. |
| 2015/0044209 A1 | 2/2015 | Brodt et al. |
| 2018/0169184 A1 | 6/2018 | D'Addio et al. |
| 2018/0243367 A1 | 8/2018 | D'Addio et al. |

FOREIGN PATENT DOCUMENTS

| WO | WO 1997/030087 A1 | 8/1997 |
| WO | WO 97/39032 A1 | 10/1997 |
| WO | WO 1998/058964 A1 | 12/1998 |
| WO | WO 1999/022764 A1 | 5/1999 |
| WO | WO 2001/053837 | 7/2001 |
| WO | WO 2001/087238 | 11/2001 |
| WO | WO 2002/020565 A2 | 3/2002 |
| WO | WO 2002/034916 A2 | 5/2002 |
| WO | WO 2003/011878 A2 | 2/2003 |
| WO | WO 2006/113880 A2 | 10/2006 |
| WO | WO 2007/024715 | 3/2007 |
| WO | WO 2008/153788 | 12/2008 |
| WO | WO 2011/133886 | 10/2011 |
| WO | WO 2012/113900 A1 | 8/2012 |
| WO | WO 2013/152989 | 10/2013 |
| WO | WO 2014/089262 | 6/2014 |
| WO | WO 2016/062792 A1 | 4/2016 |
| WO | WO 2016/193496 A1 | 12/2016 |
| WO | WO 2016/193497 A1 | 12/2016 |

OTHER PUBLICATIONS

Kuemmerle et al. Am. J. Physiol. Gastrointest. Liver Physiol. 287: G795-G802, 2004.*
Ingernnann et al. J. Biol. Chem. 285(39): 30233-30246, 2010.*
Katsanos et al. Growth Hormone and IGF Res. 11: 364-367, 2001.*
Kirman et al. Digestive Diseases and Sci. 50(4): 780-784, 2005.*
Bortvedt, S., et al., "Insulin-like growth factor 1," Current Opinion in Gastroenterology, Mar. 1, 2012, vol. 28, No. 2, pp. 89-98.
D'Addio, F., et al., "Circulating IGF-I and IGFBP3 levels control human colonic stem cell function and are disrupted in diabetic enteropathy," Cell Stem Cell, Oct. 1, 2015, vol. 17, No. 4, pp. 486-498.
Flynn, R., et al., "Endogenous IGFBP-3 regulates excess collagen expression in intestinal smooth muscle cells of Crohn's disease strictures," Inflammatory Bowel Diseases, Jan. 1, 2011, vol. 17, No. 1, pp. 193-201.
PCT International Search Report and Written Opinion for PCT/EP2016/062790, dated Sep. 26, 2016, 12 Pages.

(Continued)

*Primary Examiner* — Christine J Saoud
(74) *Attorney, Agent, or Firm* — Fenwick & West LLP

(57) ABSTRACT

The present invention relates to an inhibitor of IGFBP3 binding to TMEM219 and uses thereof for the treatment and/or prevention of an intestinal disease in a subject, in particular the treatment and/or prevention of diabetic enteropathy or inflammatory bowel disease.

10 Claims, 44 Drawing Sheets
(1 of 44 Drawing Sheet(s) Filed in Color)
Specification includes a Sequence Listing.

(56) References Cited

OTHER PUBLICATIONS

PCT International Search Report and Written Opinion for PCT/EP2016/062792, dated Sep. 30, 2016, 9 Pages.
PCT International Preliminary Report on Patentability for PCT/EP2016/062792, dated May 23, 2017, 10 Pages.
Baxter, R., IGF binding proteins in cancer: mechanistic and clinical insights, Nature Reviews, 2014, vol. 14, pp. 329-341.
Muzumdar, R., et al., "Central and Opposing Effects of IGF-1 and IGF-Binding Protein-3 on Systemic Insulin Action," Diabetes, October 2006, pp. 2788-2796, vol. 55.
Abdiche, Y.N. et al., "Exploring blocking assays using Octet, ProteOn, and Biacore biosensors," Analytical Biochemistry, Mar. 2009, vol. 386, No. 2, pp. 172-180.
Alper, C.A. et al., "Incomplete penetrance of susceptibility genes for MHC-determined immunoglobin deficiencies in monozygotic twins discordant for type 1 diabetes," Journal of Autoimmunity, 2006, vol. 27, pp. 89-95.
Angal, S. et al., "A single amino acid substitution abolishes the heterogeneity of chimeric mouse/human (IgG4) antibody," Molecular Immunology, 1993, vol. 30, No. 1, pp. 105-108.
Atkinson, M.A. et al., "Current concepts on the pathogenesis of type 1 diabetes-considerations for attempts to prevent and reverse the disease," Diabetes Care, 2015, vol. 38, pp. 979-988.
Atkinson, M.A. et al., "Does the gut microbiata have a role in type 1 diabetes? Early evidence from humans and animal models of the disease," Diabetologia, 2012, vol. 55, pp. 2868-2877.
Atkinson, M.A. et al., "Type 1 diabetes," Lancet, 2013, vol. 383, pp. 69-82.
Barker, N., "Adult intestinal stem cells: critical drivers of epithelial homeostasis and regeneration," Nat Rev Mol Cell Biol, 2014, vol. 15, pp. 19-33.
Bartfeld, S. et al., "In Vitro Expansion of Human Gastric Epithelial Stem Cells and Their Responses to Bacterial Infection," Gastroenterology, 2015, vol. 148, pp. 126-136.
Baxter, R.C., "Insulin-like growth factor binding protein-3 (IGFBP-3): Novel ligands mediate unexpected functions," J Cell Commun Signal, 2013, vol. 7, pp. 179-189.
Beck, A. et al., "Strategies and challenges for the next generation of therapeutic antibodies," Nature Reviews Immunology, 2010, vol. 10, pp. 345-352.
Ben Nasr, M. et al., "Co-transplantation of autologous MSCs delays islet allograft rejection and generates a local immunoprivileged site," Acta Diabetologica, 2015, vol. 52, pp. 917-927.
Ben Nasr, M. et al., "The rise, fall, and resurgence of immunotherapy in type 1 diabetes," Pharmacological Research, 2015, vol. 98, pp. 31-38.
Binz, H.K. et al., "Designing Repeat Proteins: Well-expressed, Soluble and Stable Proteins from Combinatorial Libraries of Consensus Ankyrin Repeat Proteins," J Mol Biol, 2003, vol. 332, pp. 489-503.
Bluestone, J.A. et al., "Genetics, pathogenesis and clinical interventions in type 1 diabetes," Nature, 2010, vol. 464, pp. 1293-1300.
Boman, B.M. et al., "Human colon cancer stem cells: a new paradigm in gastrointestinal oncology," Journal of Clinical Oncology, 2008, vol. 26, pp. 2828-2838.
Bondy, C.A. et al., "Clinical uses of insulin-like growth factor I.," Ann Intern Med, 1994, vol. 120, pp. 593-601.
Boucher, J. et al., "A kinase-independent role for unoccupied insulin and IGF-1 receptors in control of apoptosis," Sci Signal, 2010, vol. 3, pp. ra87.
Breault, D.T. et al., "Generation of mTert-GFP mice as a model to identify and study tissue progenitor cells," Proc Natl Acad Sci, 2008, vol. 105, pp. 10420-10425.
Brennand, K. et al., "Slow and steady is the key to beta-cell replication," Journal of Cellular and Molecular Medicine, 2009, vol. 13, pp. 472-487.
Brooks, B.D., "The Importance of Epitope Binning in Drug Discovery," Current Drug Discovery Technology, 2014, vol. 11, pp. 109-112.

Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, Nov. 1990, vol. 111, pp. 2129-2138.
Bytzer, P. et al., "GI symptoms in diabetes mellitus are associated with both poor glycemic control and diabetic complications," Am J Gastroenterol, 2002, vol. 97, pp. 604-611.
Camilleri, M., "Diabetic gastroparesis," N Engl J Med, 2007, vol. 356, pp. 820-829.
Cano, A.E. et al., "Gastrointestinal symptoms in patients with end-stage renal disease undergoing treatment by hemodialysis or peritoneal dialysis," Am J Gastroenterol, 2007, vol. 102, pp. 1990-1997.
Carlone, D.L. et al., "Tales from the crypt: the expanding role of slow cycling intestinal stem cells," Cell Stem Cell, 2012, vol. 10, pp. 2-4.
Carpentino, J.E. et al., "Aldehyde dehydrogenase-expressing colon stem cells contribute to tumorigenesis in the transition from colitis to cancer," Cancer Res, 2009, vol. 69, pp. 8208-8215.
Carrington, E.V. et al., "Traditional measures of normal anal sphincter function using high-resolution anorectal manometry (HRAM) in 115 healthy volunteers," Neurogastroenterology and Motility: The Official Journal of the European Gastrointestinal Motility Society, 2014, vol. 26, pp. 625-635.
Carvello, M. et al., "Inotuzumab ozogamicin murine analog-mediated B-cell depletion reduces anti-islet alto- and autoimmune responses," Diabetes, 2012, vol. 61, pp. 155-165.
Chothia, C. et al., "Structural repertoire of the human VH segments," Journal of Molecular Biology, 1992, vol. 227, No. 3, pp. 799-817.
Cui, S. et al., "Current understanding concerning intestinal stem cells," World J Gastroenterol, 2016, vol. 22, No. 31, pp. 7099-7110.
D'Addio, F. et al., "Autologous nonmyeloablative hematopoietic stem cell transplantation in new-onset type 1 diabetes: a multicenter analysis," Diabetes, 2014, vol. 63, pp. 3041-3046.
Dall'Acqua, W.F. et al., "Properties of Human IgG1s Engineered for Enhanced Binding to the Neonatal Fc Receptor (FcRn)*," The Journal of Biological Chemistry, 2006, vol. 281, No. 33, pp. 23514-23524.
De Kort, S. et al., "Diabetes mellitus, genetic variants in the insulin-like growth factor pathway and colorectal cancer risk," International Journal of Cancer, 2019, vol. 145, pp. 1774-1781.
De Santi, M. et al., "Use of hormones in doping and cancer risk," Annali di igiene: medicina preventiva e di comunita, 2019, vol. 31, No. 6, pp. 590-594.
Dhingra, A.K. et al., "An update on anti-inflammatory compounds: a review," Anti-Inflammatory & Anti-Allergy Agents in Medicinal Chemistry, 2015, vol. 14, No. 2, pp. 81-97.
Di Cairano, E.S. et al., "The glial glutamate transporter (GLT1) is expressed by pancreatic beta-cells and prevents glutamate-induced beta-cell death," The Journal of Biological Chemistry, 2011, vol. 286, pp. 14007-14018.
D'Mello, S. et al., "Innate Dysfunction Promotes Linear Growth Failure in Pediatric Crohn Disease and Growth Hormone Resistance in Murine Ileitis," Inflammatory Bowel Diseases, 2012, vol. 18, pp. 236-245.
Domenech, A. et al., "Morphofunctional changes underlying intestinal dysmotility in diabetic RIP-I/hIFNbeta transgenic mice," Int J Exp Pathol, 2011, vol. 92, pp. 400-412.
Drogan, D. et al., "Insulin-Like Growth Factor 1 and Insulin-Like Growth Factor-Binding Protein 3 in Relation to the Risk of Type 2 Diabetes Mellitus: Results from the EPIC-Potsdam Study," Am J Epidemiol, 2016, vol. 183, No. 6, pp. 553-560.
Eichele, D.D. et al., "Dextran sodium sulfate colitis murine model: an indispensable tool for advancing our understanding of inflammatory bowel disease pathogenesis," World J Gastroenterol, 2017, vol. 23, No. 33, pp. 6016-6029.
Eisenbarth, G.S., "Type I diabetes mellitus. A chronic autoimmune disease," The New England Journal of Medicine, 1986, vol. 314, pp. 1360-1368.

(56) References Cited

OTHER PUBLICATIONS

Faraj, J. et al., "Oesophageal dysmotility, delayed gastric emptying and gastrointestinal symptoms in patients with diabetes mellitus," Diabet Med, 2007, vol. 24, pp. 1235-1239.
Feldman, M. et al., "Disorders of gastrointestinal motility associated with diabetes mellitus," Ann Intern Med, 1983, vol. 98, pp. 378-384.
Filippi, C.M. et al., "Viral trigger for type 1 diabetes: pros and cons," Diabetes, 2008, vol. 57, pp. 2863-2871.
Fiorina, P. et al., "Effects of kidney-pancreas transplantation on atherosclerotic risk factors and endothelial function in patients with uremia and type 1 diabetes," Diabetes, 2001, vol. 50, pp. 496-501.
Fiorina, P. et al., "Long-term beneficial effect of islet transplantation on diabetic macro-/microangiopathy in type 1 diabetic kidney-transplanted patients," Diabetes Care, 2003, vol. 26, pp. 1129-1136.
Fiorina, P. et al., "Natural history of kidney graft survival, hypertrophy, and vascular function in end-stage renal disease type 1 diabetic kidney-transplanted patients: beneficial impact of pancreas and successful islet cotransplantation," Diabetes Care, 2005, vol. 28, pp. 1303-1310.
Fiorina, P. et al., "Normalization of multiple hemostatic abnormalities in uremic type 1 diabetes patients after kidney-pancreas transplantation," Diabetes, 2004, vol. 53, pp. 2291-2300.
Folli, F. et al., "Proteomics reveals novel oxidative and glycolytic mechanisms in type 1 diabetic patients' skin which are normalized by kidney-pancreas transplantation," PLoS One, 2010, vol. 5, pp. e9923.
Forbes, K. et al., "Transforming growth factor-β (TGFβ) receptors I/II differentially regulate TGFβ1 and IGF-binding protein-3 mitogenic effects in the human placenta," Endocrinology, 2010, vol. 151, pp. 1723-1731.
GenBank: AAH17488.1 "TMEM219 protein, partial [*Homo sapiens*]" NCBI, Jun. 16, 2008, 2 Pages, can be retrieved at <URL:https://www.ncbi.nlm.nih.gov/protein/AAH17488>.
George, M.J. et al., Current Treatment Option for Type 2 Diabetes Mellitus in Youth: Today's Realities and Lessons from the Today Study, Curr Diab Rep, 2013, vol. 13, No. 1, pp. 72-80.
Gersemann, M. et al., "From intestinal stem cells to inflammatory bowel diseases," World Journal of Gastroenterology, 2011, vol. 17, pp. 3198-3203.
Giustina, A. et al., "Insulin and GH-IGF-I axis: endocrine pacer or endocrine disruptor?" Acta Diabetol, 2014, vol. 52, pp. 433-443.
Goswami, S. et al., "Developments and Challenges for mAb-Based Therapeutics," Antibodies, 2013, vol. 2, pp. 452-500.
Gracz, A.D. et al., "Brief Report: CD24 and CD44 mark human intestinal epithelial cell populations with characteristics of active and facultative stem cells," Stem Cells, 2013, vol. 31, pp. 2024-2030.
Hinton, P.R. et al., "An Engineered Human IgG1 Antibody with Longer Serum Half-Life," The Journal of Immunology, 2006, vol. 176, No. 1, pp. 346-356.
Huch, M. et al., "In vitro expansion of single Lgr5+ liver stem cells induced by Wnt-driven regeneration," Nature, 2013, vol. 494, pp. 247-250.
Hughes, K.R. et al., "Expression profiling of Wnt family of genes in normal and inflammatory bowel disease primary human intestinal myofibroblasts and normal human colonic crypt epithelial cells," Inflamm Bowel Dis, 2011, vol. 17, pp. 213-220.
Jain, V., "Management of Type 1 Diabetes in Children and Adolescents," Indian J Pediatr, 2014, vol. 81, No. 2, pp. 170-177.
Jung, P. et al., "Isolation and in vitro expansion of human colonic stem cells," Nat Med, 2011, vol. 17, pp. 1225-1227.
Kam, N.W.S. et al., "Carbon nanotubes as multifunctional biological transporters and near-infrared agents for selective cancer cell destruction," PNAS, 2005, vol. 102, No. 33, pp. 11600-11605.
Kaplan, G.G., "The global burden of IBD: from 2015 to 2025," Nat Rev Gastroenterol Hepatol, 2015, vol. 12, No. 12, pp. 720-727.
Keenan, H.A. et al., "Residual insulin production and pancreatic β-cell turnover after 50 years of diabetes: Joslin Medalist Study," Diabetes, 2010, vol. 59, No. 11, pp. 2846-2853.

Kohl, A. et al., "Designed to be stable: Crystal structure of a consensus ankyrin repeat protein," PNAS, 2003, vol. 100, No. 4, pp. 1700-1705.
Kosinksi, C. et al., "Gene expression patterns of human colon tops and basal crypts and BMP antagonists as intestinal stem cell niche factors," Proceedings of the National Academy of Sciences of the United States of America, 2007, vol. 104, pp. 15418-15423.
Kundu, P. et al., "An EphB-Abl signaling pathway is associated with intestinal tumor initiation and growth," Science Translational Medicine, 2015, vol. 7, pp. 281ra44.
Lazar, E. et al., "Transforming Growth Factor alpha: mutation of aspartic acid 47 and leucine 48 results in different biological activities," Molecular and Cellular Biology, Mar. 1988, vol. 8, No. 3, pp. 1247-1252.
Le Roith, D., "Seminars in medicine of the Beth Israel Deaconess Medical Center. Insulin-like growth factors," N Engl J Med, 1997, vol. 336, pp. 633-640.
Lin, M.C. et al. "Structure-function relations in glucagon. Properties of highly purified Des-his1-, monoiodo-, and [Des-Asn28, Thr29](homoserine lactone27)-glucagon," Biochemistry, 1975, vol. 14, No. 8, pp. 1559-1563.
Ma, X. et al., "A new mutation in BFSP2 (G1091A) causes autosomal dominant congenital lamellar cataracts," Molecular Vision, 2008, vol. 14, pp. 1906-1911.
Mahe, M.M. et al., "Establishment of gastrointestinal epithelial organoids," Curr Protoc Mouse Biol, 2013, vol. 3, pp. 217-240.
Marsha, J.D., "Lipid Management in Patients with Type 2 Diabetes," Am Health Drug Benefits, 2011, vol. 4, No. 5, pp. 312-322.
McLean, M.H. et al., "Does the microbiota play a role in the pathogenesis of autoimmune diseases?", Gut, 2015, vol. 64, pp. 332-341.
Medema, J.P. et al., "Microenvironmental regulation of stem cells in intestinal homeostasis and cancer," Nature, 2011, vol. 474, pp. 318-326.
Meier, J.J. et al., "Sustained beta cell apoptosis in patients with long-standing type 1 diabetes: indirect evidence for islet regeneration?", Diabetologia, 2005, vol. 48, No. 11, pp. 2221-2228.
Merlos-Suarez, A. et al., "The intestinal stem cell signature identifies colorectal cancer stem cells and predicts disease relapse," Cell Stem Cell, 2011, vol. 8, pp. 511-524.
Munoz, J. et al., "The Lgr5 intestinal stem cell signature: robust expression of proposed quiescent '+4' cell markers," EMBO J, 2012, vol. 31, pp. 3079-3091.
Nano, R. et al., "Islet isolation for alltransplantation: variables associated with successful islet yield and graft function," Diabetologia, 2005, vol. 48, pp. 906-912.
Nathan, D.M., "Diabetes: Advances in Diagnosis and Treatment," Jama, 2015, vol. 314, pp. 1052-1062.
Nguyen, K.H. et al., "Human IGF Binding Protein-3 Overexpression Impairs Glucose Regulation in Mice via an Inhibition of Insulin Secretion," Endocrinology, 2011, vol. 152, No. 6, pp. 2184-2196.
Oh, Y. et al., "Antiproliferative actions of insulin-like growth factor binding protein (IGFBP)-3 in human breast cancer cells," Prog Growth Factor Res, 1995, vol. 6, pp. 503-512.
Oilinki, T. et al., "Prevalence and characteristics of diabetes among Somali children and adolescents living in Helsinki, Finland," Pediatric Diabetes, 2012, vol. 13, pp. 176-180.
Pambianco, G. et al. "The 30-year natural history of type 1 diabetes complications: the Pittsburgh Epidemiology of Diabetes Complications Study experience," Diabetes, 2006, vol. 55, pp. 1463-1469.
Peet, A. et al., "Circulating IGF1 and IGFBP3 in relation to the development of β-cell autoimmunity in young children," Eur J Endocrinol, 2015, vol. 173, No. 2, pp. 129-137.
Petkova, S.B. et al., "Enhanced half-life of genetically engineered human IgG1 antibodies in a humanized FcRn mouse model: potential application in humorally mediated autoimmune disease," International Immunology, 2006, vol. 18, No. 12, pp. 1759-1769.
Petrelli, A. et al., "IL-21 is an antitolerogenic cytokine of the late-phase alloimmune response," Diabetes, 2011, vol. 60, pp. 3223-3234.
Piscaglia, A.C. et al., "Circulating hematopoietic stem cells and putative intestinal stem cells in coeliac disease," Journal of Translational Medicine, 2015, vol. 13, pp. 220.

(56) References Cited

OTHER PUBLICATIONS

Pithadia, A.B. et al., "Treatment of inflammatory bowel disease (IBD)" Pharmacological Reports, 2011, vol. 63, pp. 629-642.
Pupim, L.B. et al., "Accelerated lean body mass loss in incident chronic dialysis patients with diabetes mellitus," Kidney Int, 2005, vol. 68, pp. 2368-2374.
Remes-Troche, J.M., et al., "Rectoanal reflexes and sensorimotor response in rectal hyposensitivity," Diseases of the Colon and Rectum, 2010, vol. 53, pp. 1047-1054.
Sato, T. et al., "Growing self-organizing mini-guts from a single intestinal stem cell: mechanism and applications," Science, 2013, vol. 340, pp. 1190-1194.
Schonhoff, S.E. et al., "Minireview: Development and Differentiation of Gut Endocrine Cells," Endocrinology, 2004, vol. 145, pp. 2639-2644.
Schwartz, G.P. et al., "A superactive insulin: [B10 Aspartic acid]insulin(human)," Proc Natl Acad Sci, Sep. 1987, vol. 84, pp. 6408-6411.
Schwarz, P.E. et al., "Nonpharmacological interventions for the prevention of type 2 diabetes mellitus," Nature Reviews Endocrinology, 2012, vol. 8, pp. 363-373.
Secchi, A. et al., "Cardiovascular disease and neoplasms after pancreas transplantation," Lancet, 1998, vol. 352, pp. 65-66.
Senger, S. et al., "Celiac Disease Histopathology Recapitulates Hedgehog Downregulation, Consistent with Wound Healing Processes Activation," PloS One, 2015, vol. 10, pp. e0144634.
Smets, Y.F. et al., "Effect of simultaneous pancreas-kidney transplantation on mortality of patients with type-1 diabetes mellitus and end-stage renal failure," Lancet, 1999, vol. 1915-1919.
Spinelli, A. et al. "Intestinal fibrosis in Crohn's disease: medical treatment or surgery?," Current Drug Targets, 2010, vol. 11, No. 2, pp. 242-248.
Sridhar, S.S. et al., "Insulin-insulin-like growth factor axis and colon cancer," J Clin Oncol, 2009, vol. 27, pp. 165-167.
Stange, D.E. et al., "Concise review: the yin and yang of intestinal (cancer) stem cells and their progenitors," Stem Cells, 2013, vol. 31, pp. 2287-2295.
Svedlund, J. et al., "GSRS—a clinical rating scale for gastrointestinal symptoms in patients with irritable bowel syndrome and peptic ulcer disease," Digestive diseases, 1988, vol. 33, pp. 129-134.
Taghipour, N. et al., "An experimental model of colitis induced by dextran sulfate sodium from acute progresses to chronicity in C57BL/6: correlation between conditions of mice and the environment," Gastroenterology and Hepatology from Bed to Bench, 2016, vol. 9, No. 1, pp. 45-52.
Talley, N.J. et al., "Impact of chronic gastrointestinal symptoms in diabetes mellitus on health-related quality of life," Am J Gastroenterol, 2001, vol. 96, pp. 71-76.
The Diabetes Control and Complications Research Group, "The effect of intensive treatment of diabetes on the development and progression of long-term complications in insulin-dependent mellitus," N Engl J Med, Sep. 30, 1993, vol. 329, pp. 977-986.
Tomlinson, I.M. et al., "The repertoire of human germline VH sequences reveals about fifty groups of VH segments with different hypervariable loops," Journal of Molecular Biology, 1992, vol. 227, No. 3, pp. 776-798.
United States Office Action, U.S. Appl. No. 15/945,644, dated Dec. 2, 2019, eight pages.
United States Office Action, U.S. Appl. No. 15/945,644, dated Jan. 8, 2019, ten pages.
United States Office Action, U.S. Appl. No. 15/945,644, dated Jul. 26, 2018, nine pages.
United States Office Action, U.S. Appl. No. 15/945,644, dated May 2, 2019, 11 pages.
Van Der Flier, L.G. et al., "Stem cells, self-renewal, and differentiation in the intestinal epithelium," Annual Review of Physiology, 2009, vol. 71, pp. 241-290.
Venepalli, N.K. et al., "Phase I Study of IGF-Methotrexate Conjugate in the Treatment of Advanced Tumors Expressing IGF-1 R," American Journal of Clinical Oncology, Nov. 2019, vol. 42, No. 11, pp. 862-869.
Vergani, A. et al., "A novel clinically relevant strategy to abrogate autoimmunity and regulate alloimmunity in NOD mice," Diabetes, 2010, vol. 59, pp. 2253-2264.
Vergani, A. et al., "Effect of the purinergic inhibitor oxidized ATP in a model of islet allograft rejection," Diabetes, 2013, vol. 62, pp. 1665-1675.
Wang, S. et al., "Circulating IGF-1 promotes prostate adenocarcinoma via FOXO31/BIM signaling in a double-transgenic mouse model," Oncogene, Jul. 16, 2019, vol. 38, pp. 6338-6353.
Wang, Z. et al., "Integrin targeted drug and gene delivery," Expert Opinion on Drug Delivery, 2010, vol. 7, No. 2, pp. 159-171.
Williams, A.C. et al., "Insulin-like growth factor binding protein 3 (IGFBP-3) potentiates Trail-induced apoptosis of human colorectal carcinoma cells through inhibition of NF-kappaB," Cell Death Differ, 2007, vol. 14, pp. 137-145.
Wright, A. et al., "Effect of glycosylation on antibody function: implications for genetic engineering," Trends in Biotechnology, 1997, vol. 15, No. 1, pp. 26-32.
Wu, M.J. et al., "Colonic transit time in long-term dialysis patients," Am J Kidney Dis, 2004, vol. 44, pp. 322-327.
Yakar, S. et al., "Serum complexes of insulin-like growth factor-1 modulate skeletal integrity and carbohydrate metabolism," FASEB J, 2009, vol. 23, No. 3, pp. 709-719.
Yancu, D. et al., "A phenotype of IGFBP-3 knockout mice revealed by dextran sulfate-induced colitis," Journal of gastroenterology and hepatology, 2017, vol. 32, No. 1, pp. 146-153.
Yeung, Y.A. et al., "Engineering Human IgG1 Affinity to Human Neonatal Fc Receptor: Impact of Affinity Improvement on Pharmacokinetics in Primates," The Journal of Immunology, 2009, vol. 182, No. 12, pp. 7663-7671.
Yi, P. et al., "Perspectives on the activities of ANGPTL8/betatrophin," Cell, 2014, vol. 159, pp. 467-468.
Zahnd, C. et al., "A Designed Ankyrin Repeat Protein Evolved to Picomolar Affinity to Her2," J Mol Biol, 2007, vol. 369, pp. 1015-1028.
Zeki, S.S. et al., "Stem cells and their implications for colorectal cancer," Nature Reviews, Gastroenterology & Hepatology, 2011, vol. 8, pp. 90-100.
Zhao, J. et al., "Biomechanical and morphometric intestinal remodelling during experimental diabetes in rats," Diabetologia, 2003, vol. 46, pp. 1688-1697.
Ziegler, A.G. et al., "Seroconversion to multiple islet autoantibodies and risk of progression to diabetes in children," Jama, 2013, vol. 309, pp. 2473-2479.
Ziskin, J.L. et al., "In situ validation of an intestinal stem cell signature in colorectal cancer," Gut, 2013, vol. 62, pp. 1012-1023.

* cited by examiner

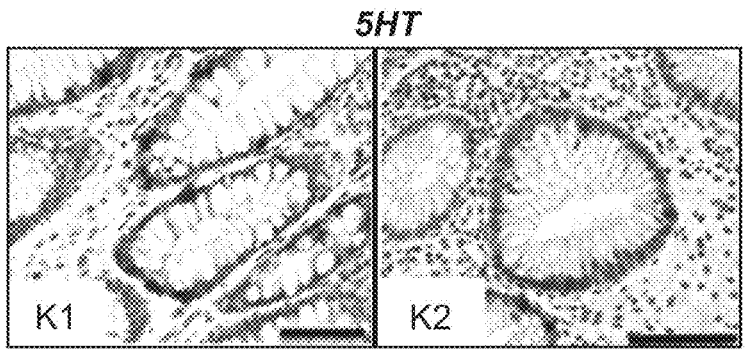
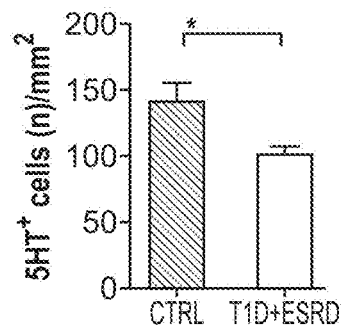
FIG. 1K  FIG. 1L
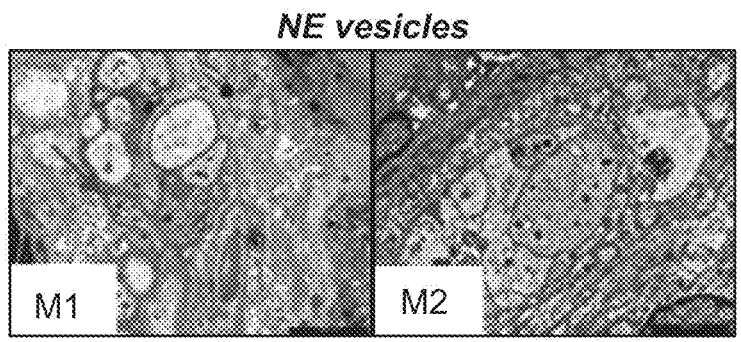
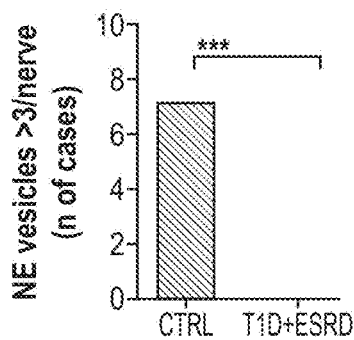
FIG. 1M  FIG. 1N
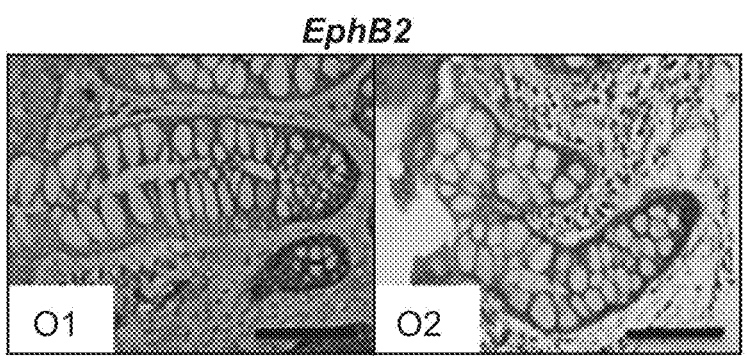
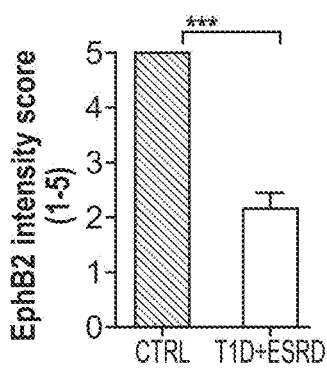
FIG. 1O  FIG. 1P
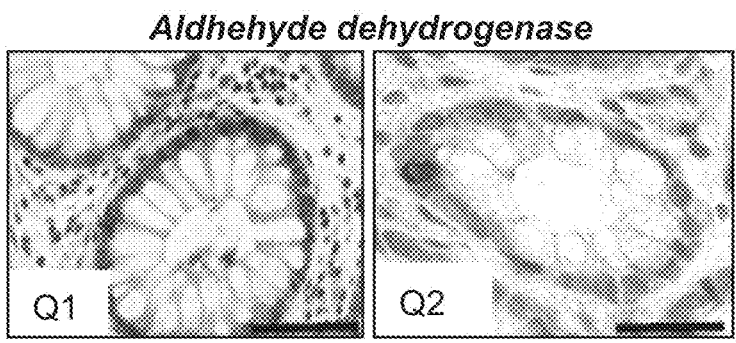
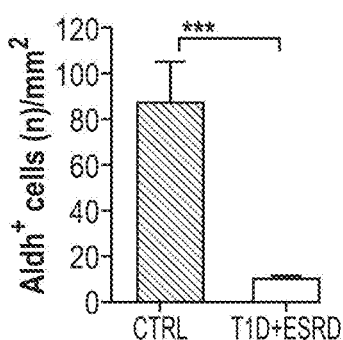
FIG. 1Q  FIG. 1R

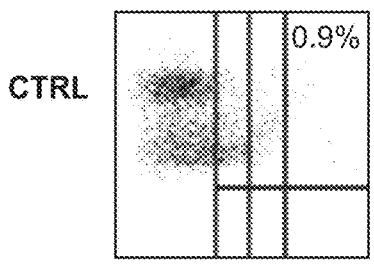
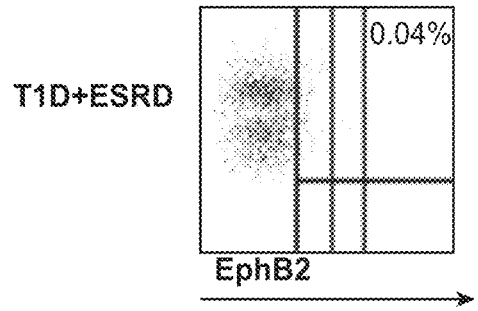
FIG. 2A
FIG. 2B
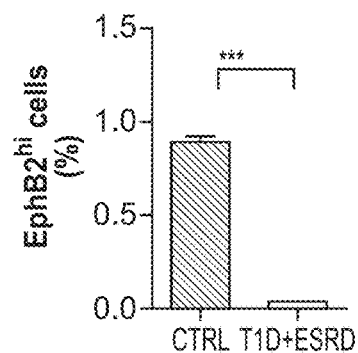
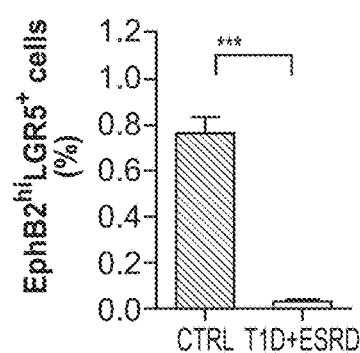
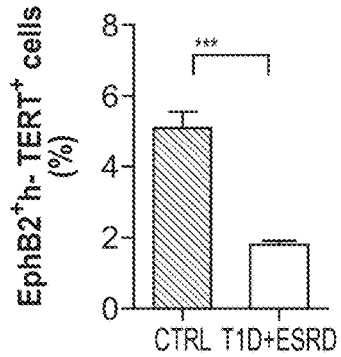
FIG. 2C
FIG. 2D
FIG. 2E
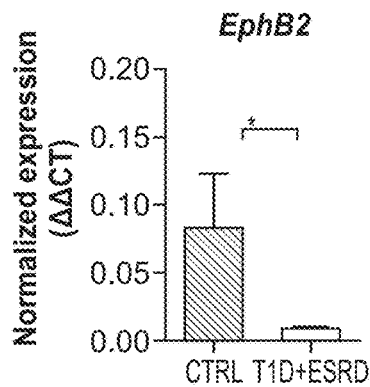
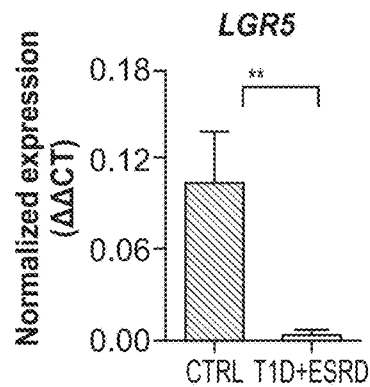
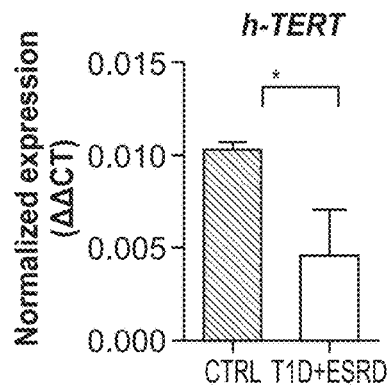
FIG. 2F
FIG. 2G
FIG. 2H

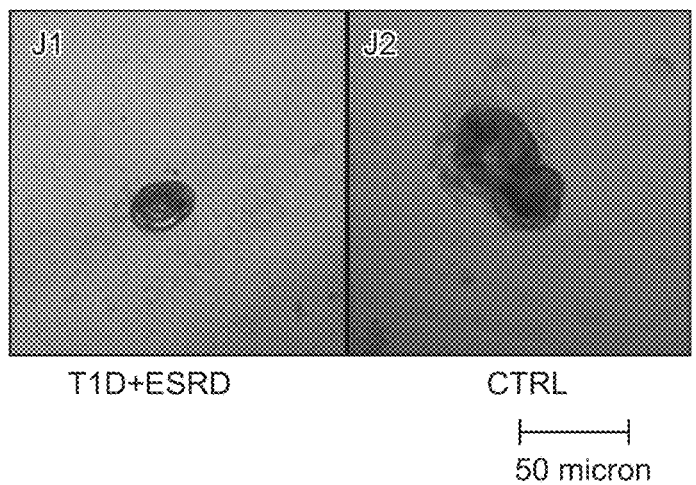
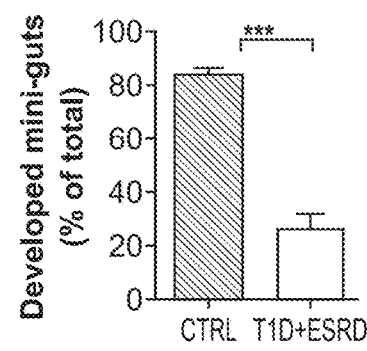
FIG. 2J
FIG. 2K
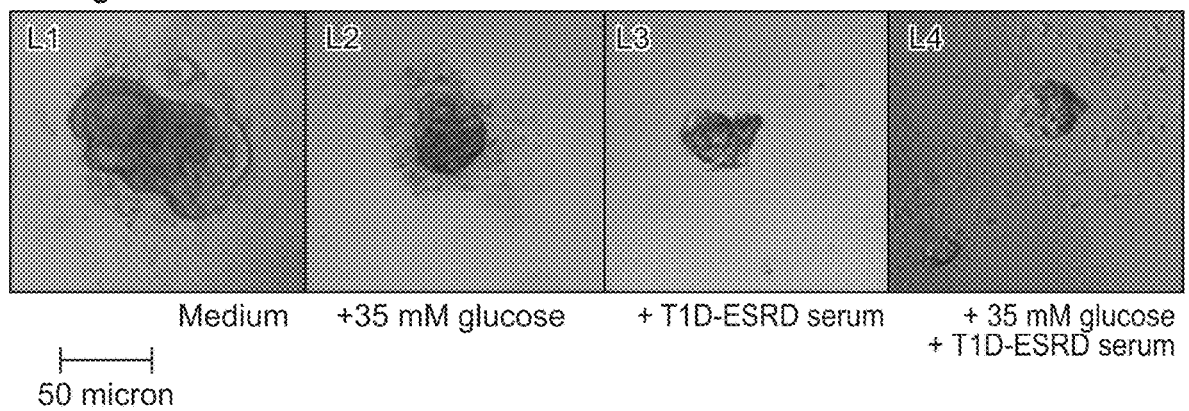
FIG. 2L

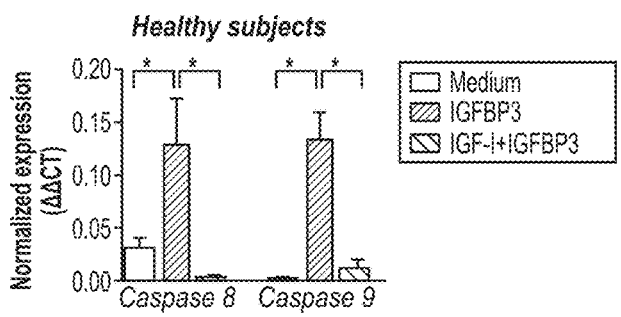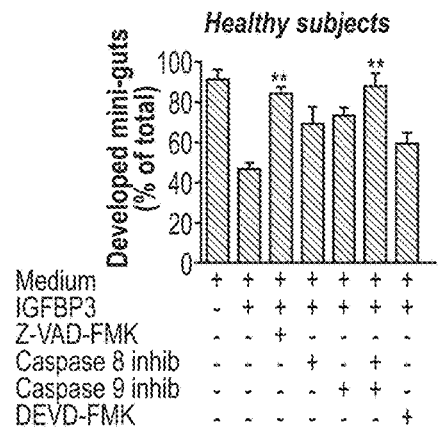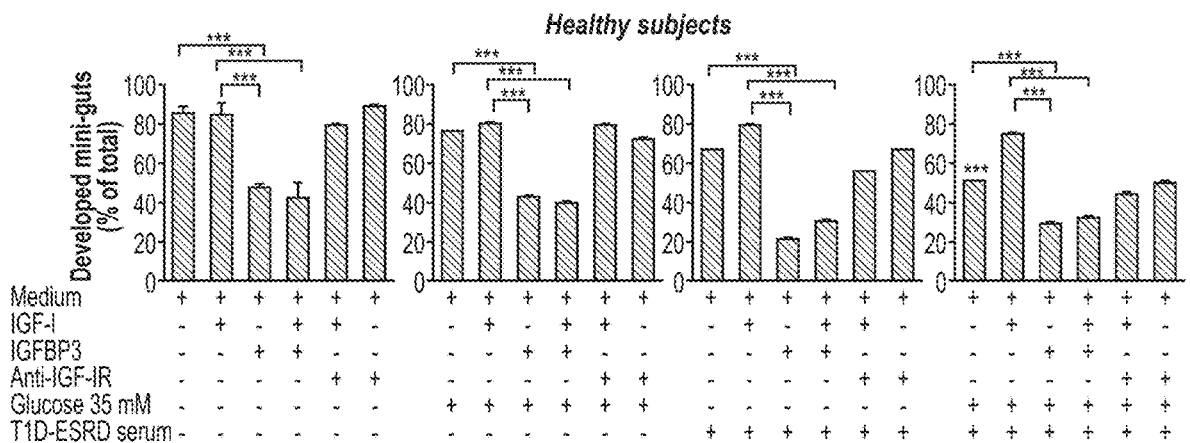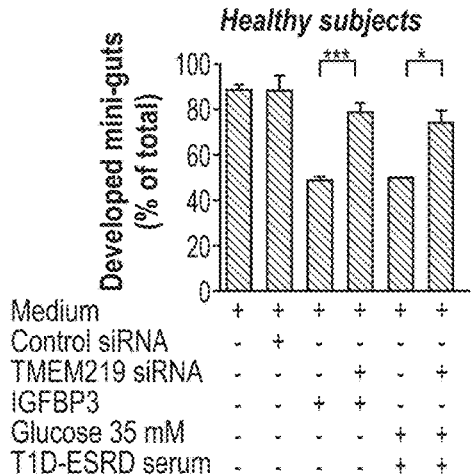
FIG. 3J
FIG. 3K
FIG. 3L
FIG. 3M

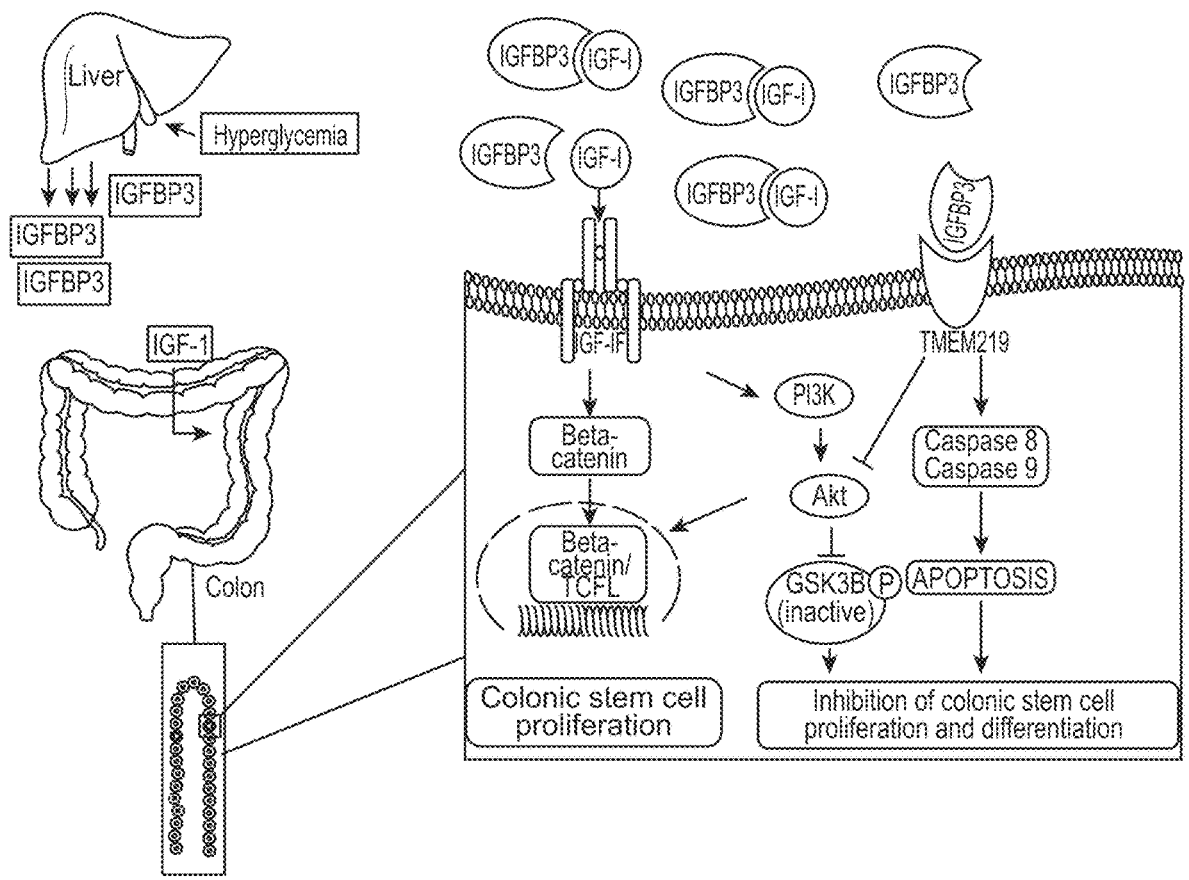
FIG. 4E
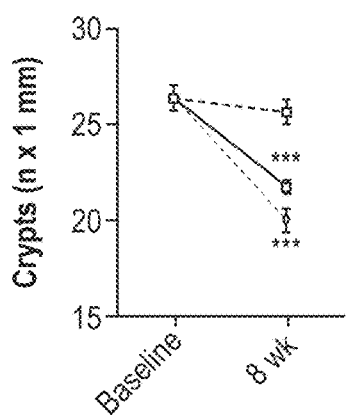
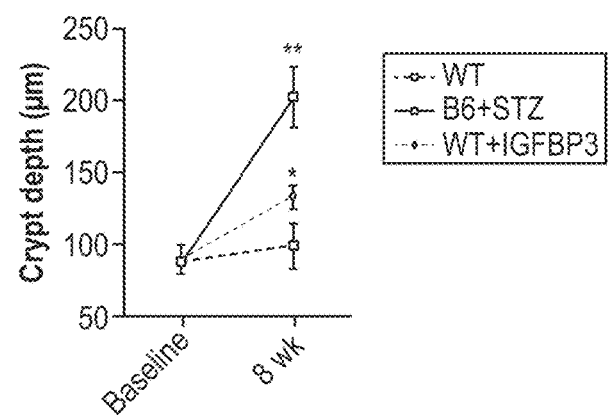
FIG. 4F
FIG. 4G

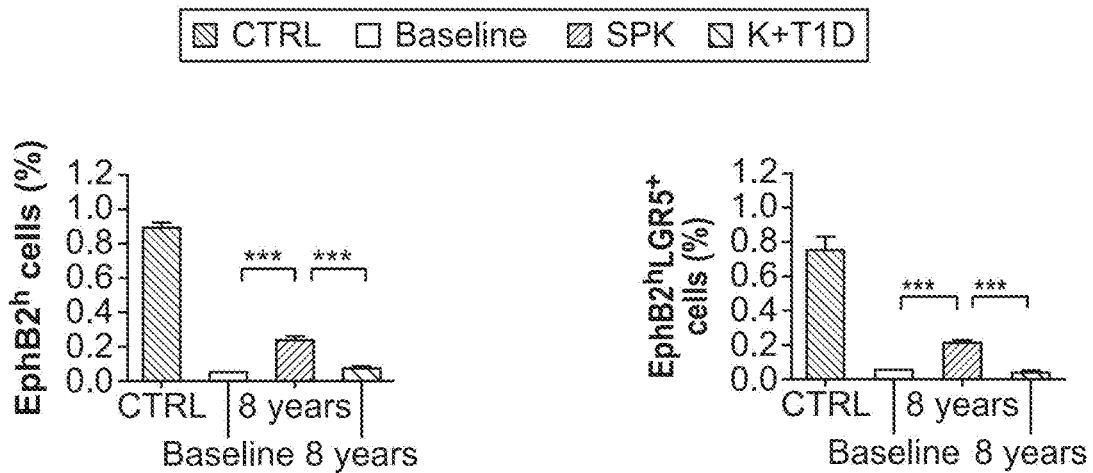
FIG. 5A
FIG. 5B
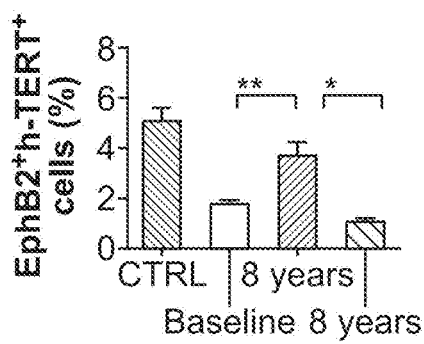
FIG. 5C
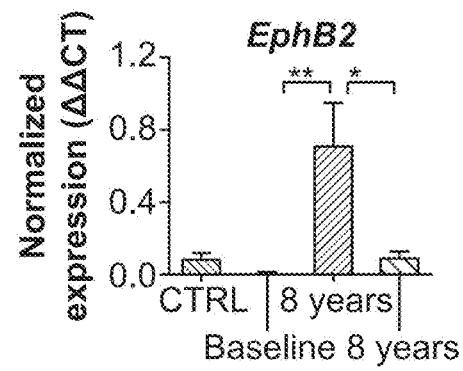
FIG. 5D
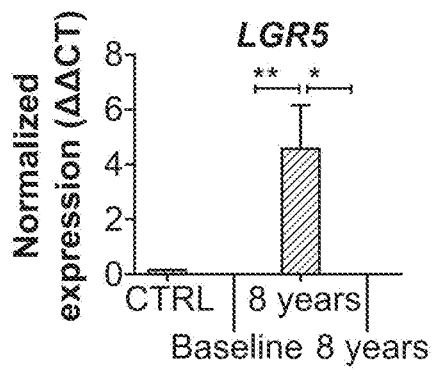
FIG. 5E
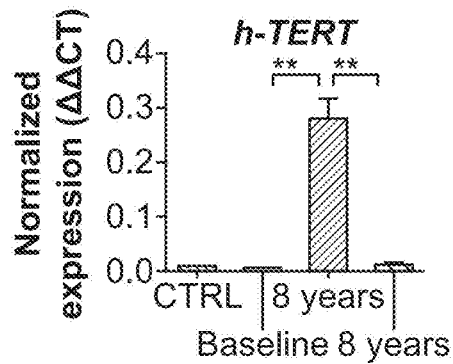
FIG. 5F

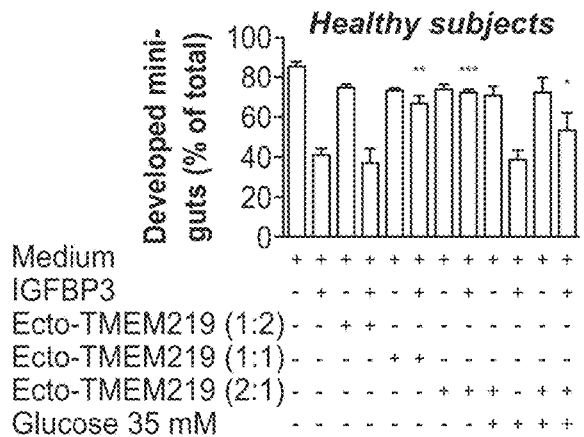
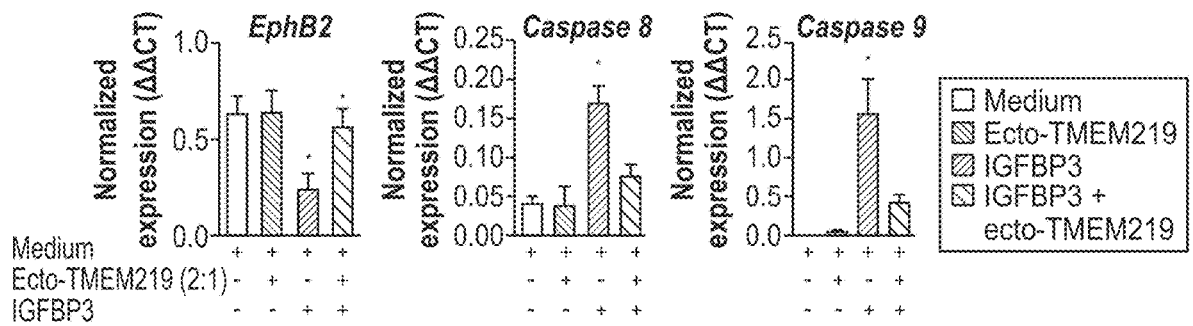
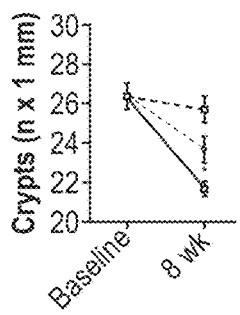
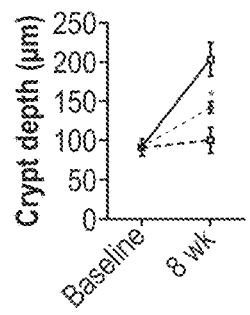
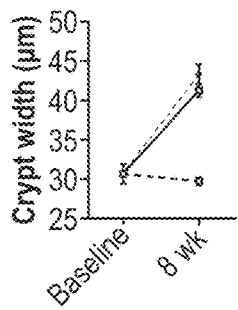
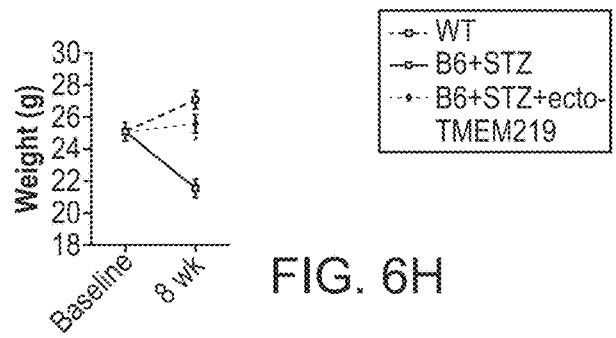
FIG. 6A
FIG. 6B  FIG. 6C  FIG. 6D
FIG. 6E  FIG. 6F
FIG. 6G  FIG. 6H

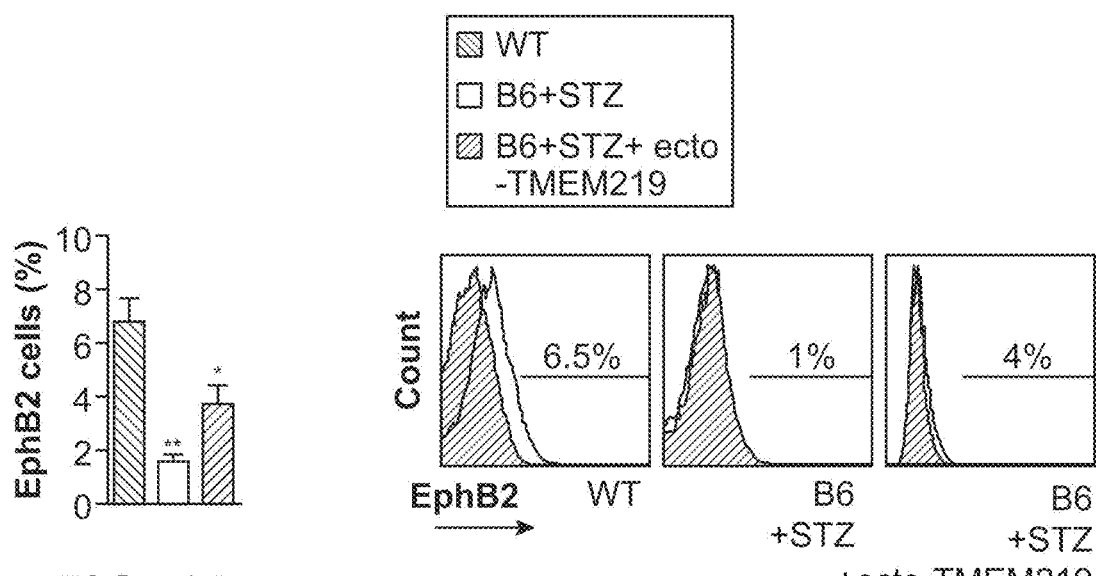
FIG. 6I
FIG. 6J
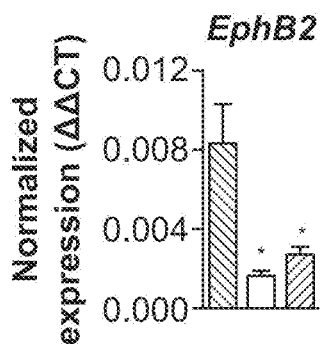
FIG. 6K
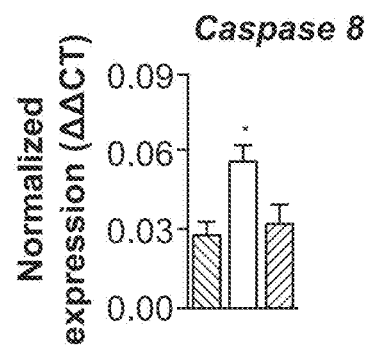
FIG. 6L
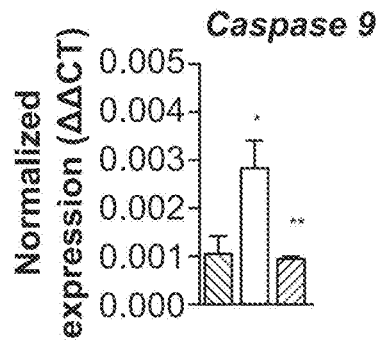
FIG. 6M
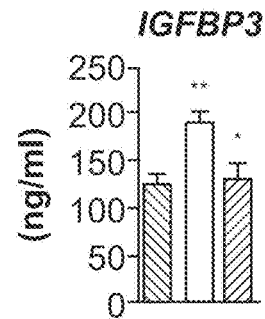
FIG. 6N

*T1D+ESRD with eGFR < 15 ml/min/m²*

*CTRL+T1D with eGFR > 15 ml/min/m²*

*No-ESRD*

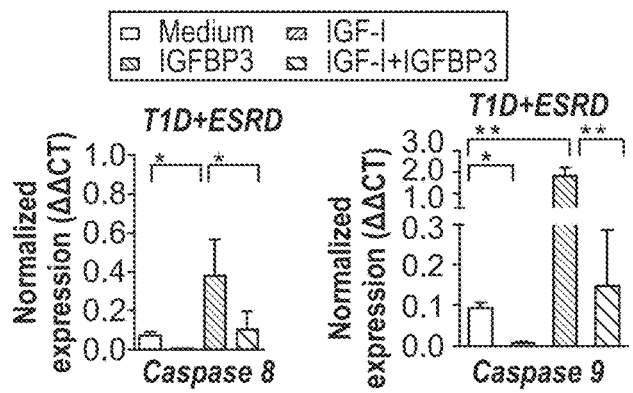
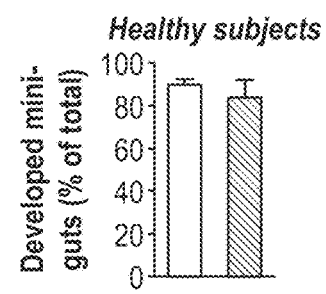
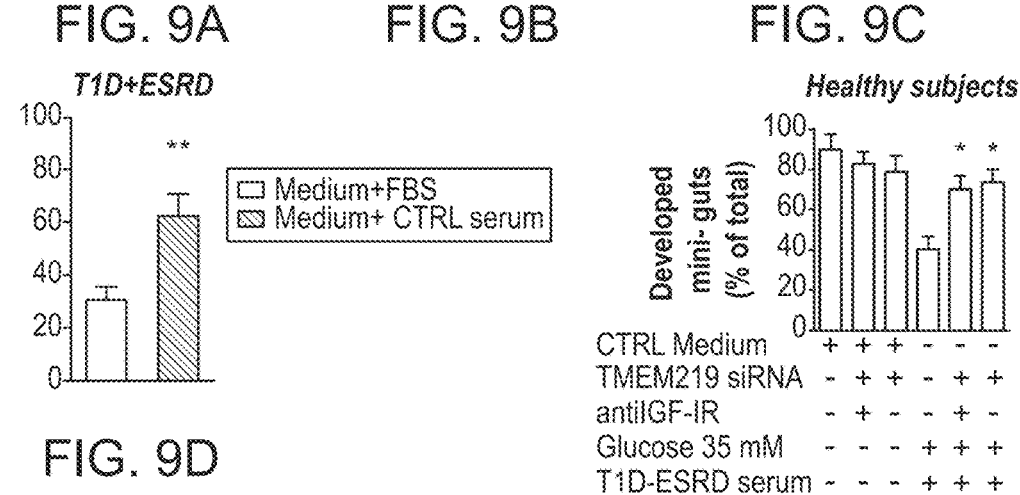
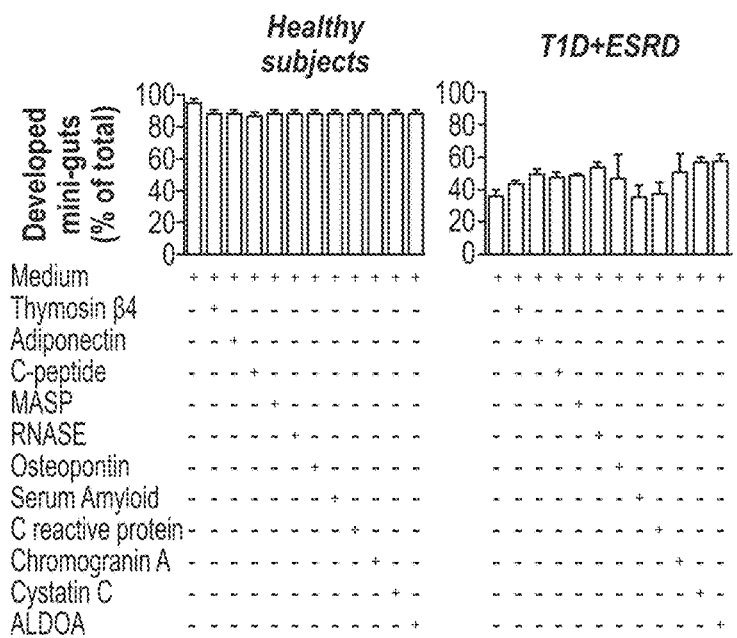
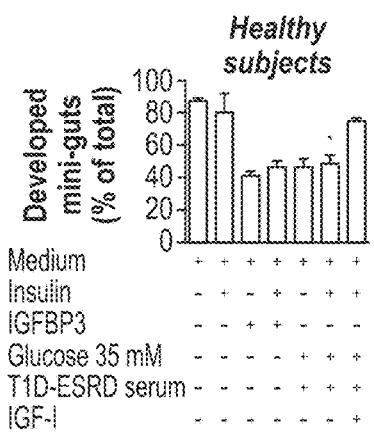

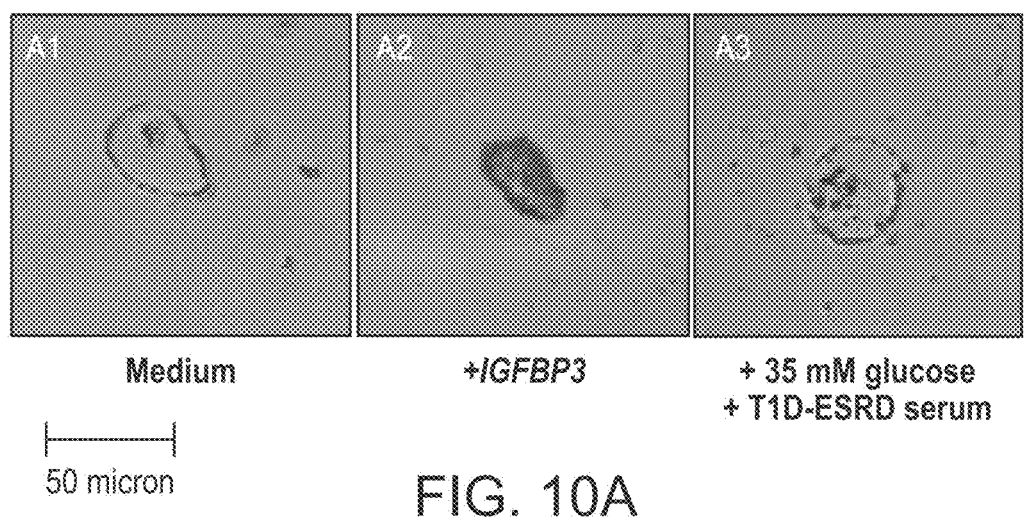
FIG. 10A
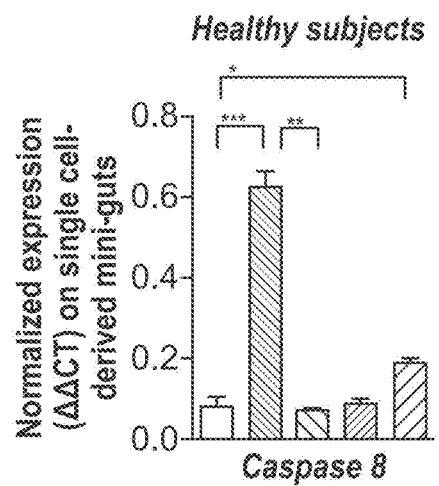
FIG. 10B
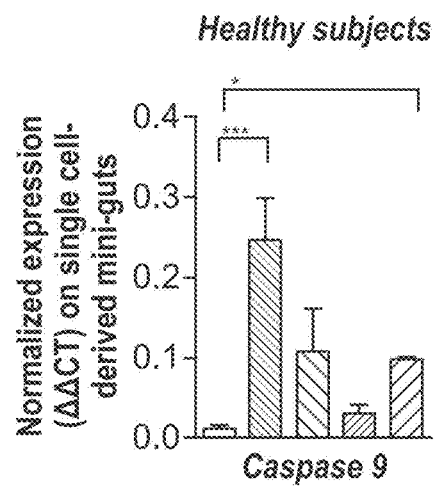
FIG. 10C
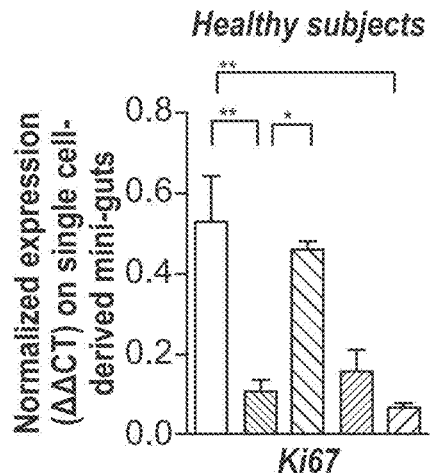
FIG. 10D
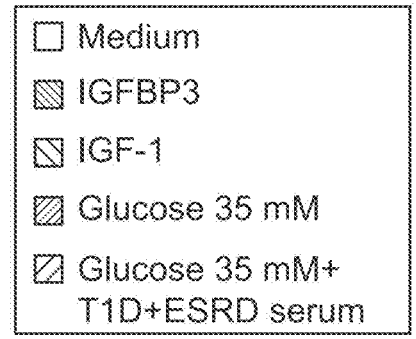

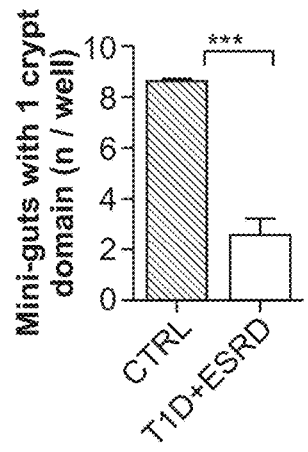
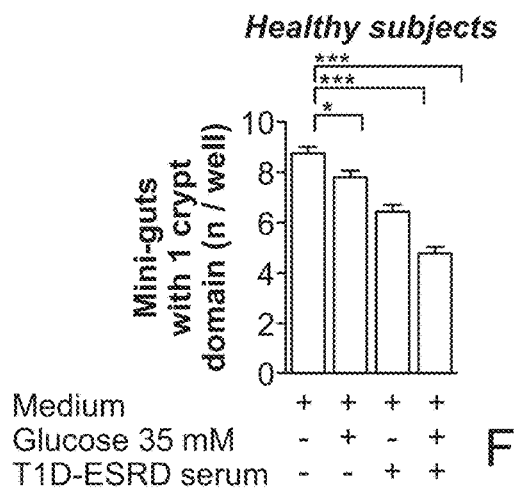
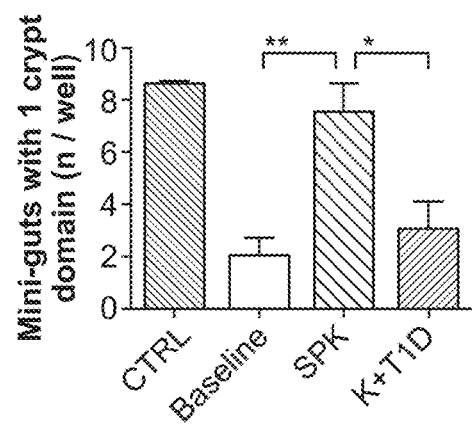
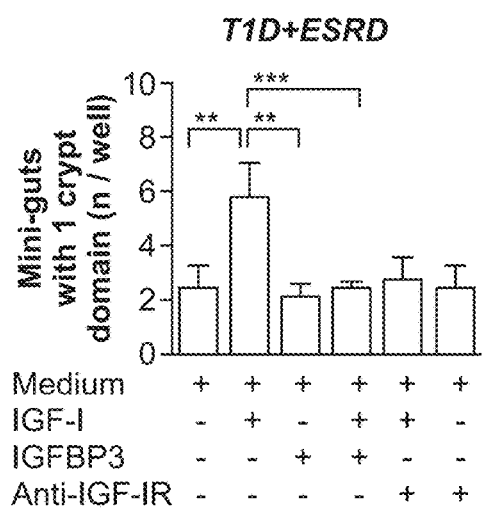
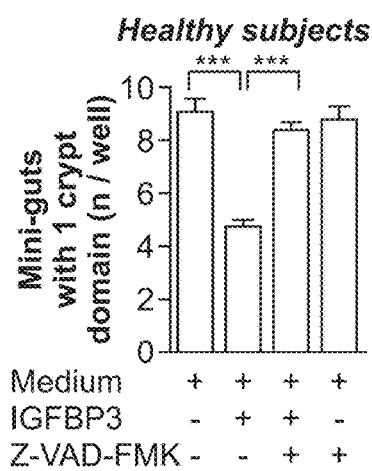
FIG. 17A
FIG. 17B
FIG. 17C
FIG. 17D
FIG. 17E

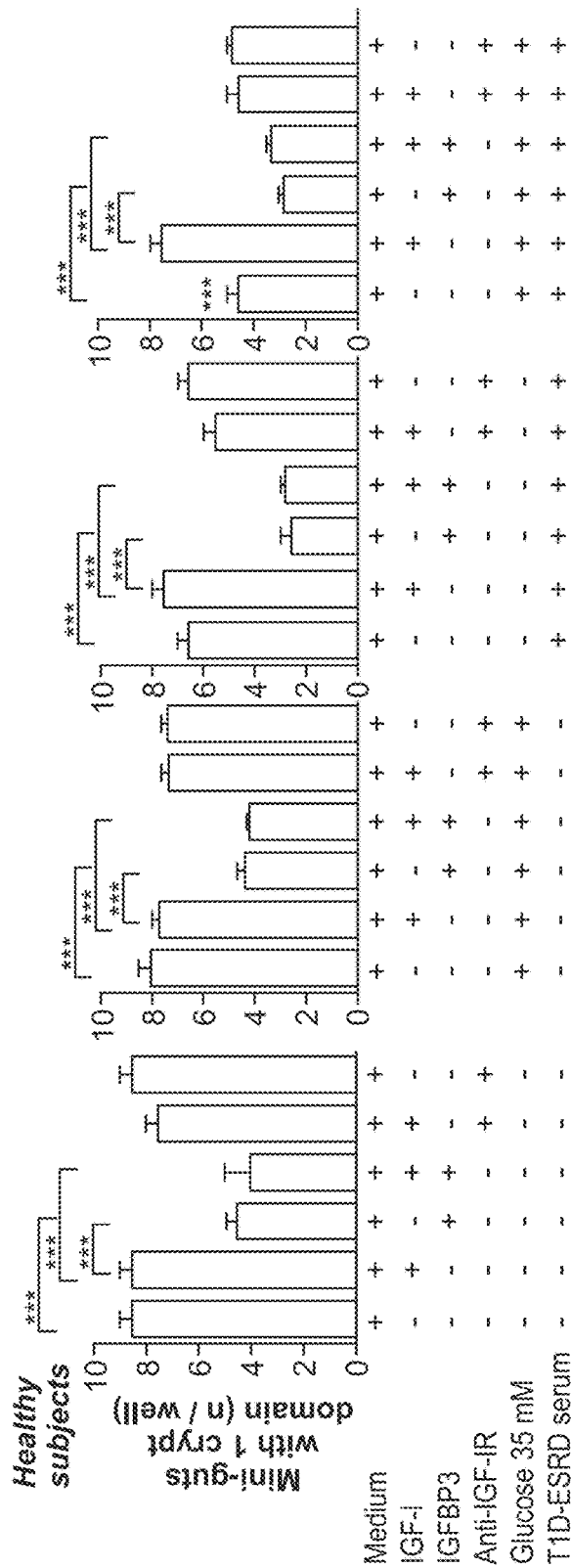
FIG. 17F
FIG. 17G
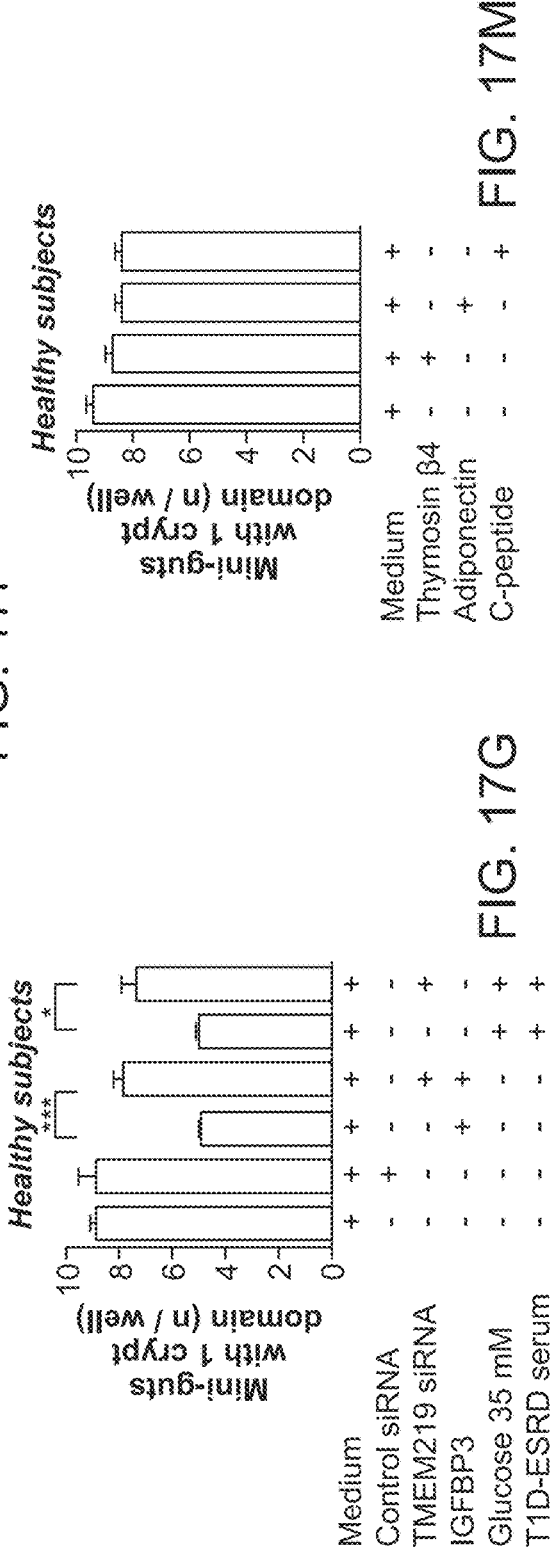
FIG. 17M

SEQUENCE LISTING

```
<160> NUMBER OF SEQ ID NOS: 4

<210> SEQ ID NO 1
<211> LENGTH: 240
<212> TYPE: PRT
<213> ORGANISM: Homo sapiens

<400> SEQUENCE: 1

Met Gly Asn Cys Gln Ala Gly His Asn Leu His Leu Cys Leu Ala His
1               5                  10                  15

His Pro Pro Leu Val Cys Ala Thr Leu Ile Leu Leu Leu Gly Leu
            20                  25                  30

Ser Gly Leu Gly Leu Gly Ser Phe Leu Leu Thr His Arg Thr Gly Leu
        35                  40                  45

Arg Ser Pro Asp Ile Pro Gln Asp Trp Val Ser Phe Leu Arg Ser Phe
    50                  55                  60

Gly Gln Leu Thr Leu Cys Pro Arg Asn Gly Thr Val Thr Gly Lys Trp
65                  70                  75                  80
```

```
Arg Gly Ser His Val Val Gly Leu Leu Thr Thr Leu Asn Phe Gly Asp
                85                  90                  95

Gly Pro Asp Arg Asn Lys Thr Arg Thr Phe Gln Ala Thr Val Leu Gly
            100                 105                 110

Ser Gln Met Gly Leu Lys Gly Ser Ala Gly Gln Leu Val Leu Ile
        115                 120                 125

Thr Ala Arg Val Thr Thr Glu Arg Thr Ala Gly Thr Cys Leu Tyr Phe
    130                 135                 140

Ser Ala Val Pro Gly Ile Leu Pro Ser Ser Gln Pro Pro Ile Ser Cys
145                 150                 155                 160

Ser Glu Glu Gly Ala Gly Asn Ala Thr Leu Ser Pro Arg Met Gly Glu
                165                 170                 175

Glu Cys Val Ser Val Trp Ser His Glu Gly Leu Val Leu Thr Lys Leu
            180                 185                 190

Leu Thr Ser Glu Glu Leu Ala Leu Cys Gly Ser Arg Leu Leu Val Leu
        195                 200                 205

Gly Ser Phe Leu Leu Leu Phe Cys Gly Leu Leu Cys Cys Val Thr Ala
    210                 215                 220

Met Cys Phe His Pro Arg Arg Glu Ser His Trp Ser Arg Thr Arg Leu
225                 230                 235                 240

<210> SEQ ID NO 2
<211> LENGTH: 162
<212> TYPE: PRT
<213> ORGANISM: Homo sapiens

<400> SEQUENCE: 2

Thr His Arg Thr Gly Leu Arg Ser Pro Asp Ile Pro Gln Asp Trp Val
1               5                   10                  15

Ser Phe Leu Arg Ser Phe Gly Gln Leu Thr Leu Cys Pro Arg Asn Gly
            20                  25                  30

Thr Val Thr Gly Lys Trp Arg Gly Ser His Val Val Gly Leu Leu Thr
        35                  40                  45

Thr Leu Asn Phe Gly Asp Gly Pro Asp Arg Asn Lys Thr Arg Thr Phe
    50                  55                  60

Gln Ala Thr Val Leu Gly Ser Gln Met Gly Leu Lys Gly Ser Ala
65                  70                  75                  80

Gly Gln Leu Val Leu Ile Thr Ala Arg Val Thr Thr Glu Arg Thr Ala
                85                  90                  95

Gly Thr Cys Leu Tyr Phe Ser Ala Val Pro Gly Ile Leu Pro Ser Ser
            100                 105                 110

Gln Pro Pro Ile Ser Cys Ser Glu Glu Gly Ala Gly Asn Ala Thr Leu
        115                 120                 125

Ser Pro Arg Met Gly Glu Glu Cys Val Ser Val Trp Ser His Glu Gly
    130                 135                 140

Leu Val Leu Thr Lys Leu Leu Thr Ser Glu Glu Leu Ala Leu Cys Gly
145                 150                 155                 160

Ser Arg

<210> SEQ ID NO 3
<211> LENGTH: 166
<212> TYPE: PRT
<213> ORGANISM: Homo sapiens

<400> SEQUENCE: 3
```

```
Ser Phe Leu Leu Thr His Arg Thr Gly Leu Arg Ser Pro Asp Ile Pro
1               5                   10                  15

Gln Asp Trp Val Ser Phe Leu Arg Ser Phe Gly Gln Leu Thr Leu Cys
            20                  25                  30

Pro Arg Asn Gly Thr Val Thr Gly Lys Trp Arg Gly Ser His Val Val
            35                  40                  45

Gly Leu Leu Thr Thr Leu Asn Phe Gly Asp Gly Pro Asp Arg Asn Lys
50                  55                  60

Thr Arg Thr Phe Gln Ala Thr Val Leu Gly Ser Gln Met Gly Leu Lys
65                  70                  75                  80

Gly Ser Ser Ala Gly Gln Leu Val Leu Ile Thr Ala Arg Val Thr Thr
            85                  90                  95

Glu Arg Thr Ala Gly Thr Cys Leu Tyr Phe Ser Ala Val Pro Gly Ile
            100                 105                 110

Leu Pro Ser Ser Gln Pro Pro Ile Ser Cys Ser Glu Glu Gly Ala Gly
            115                 120                 125

Asn Ala Thr Leu Ser Pro Arg Met Gly Glu Glu Cys Val Ser Val Trp
130                 135                 140

Ser His Glu Gly Leu Val Leu Thr Lys Leu Leu Thr Ser Glu Glu Leu
145                 150                 155                 160

Ala Leu Cys Gly Ser Arg
            165

<210> SEQ ID NO 4
<211> LENGTH: 297
<212> TYPE: PRT
<213> ORGANISM: Homo sapiens

<400> SEQUENCE: 4

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
            35                  40                  45

Ala Gln Cys Ala Pro Pro Pro Ala Val Cys Ala Glu Leu Val Arg Glu
50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
            85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
            115                 120                 125

Pro Ala Pro Pro Ala Pro Gly Glu Pro Ala Pro Gly Asn Ala Ser
130                 135                 140

Glu Ser Glu Glu Asp Arg Ser Ala Gly Ser Val Glu Ser Pro Ser Val
145                 150                 155                 160

Ser Ser Thr His Arg Val Ser Asp Pro Lys Phe His Pro Leu His Ser
            165                 170                 175

Lys Ile Ile Ile Ile Lys Lys Gly His Ala Lys Asp Ser Gln Arg Tyr
            180                 185                 190

Lys Val Asp Tyr Glu Ser Gln Ser Thr Asp Thr Gln Asn Phe Ser Ser
            195                 200                 205
```

-continued

```
Glu Ser Lys Arg Glu Thr Glu Tyr Gly Pro Cys Arg Arg Glu Met Glu
    210                 215                 220

Asp Thr Leu Asn His Leu Lys Phe Leu Asn Val Leu Ser Pro Arg Gly
225                 230                 235                 240

Val His Ile Pro Asn Cys Asp Lys Lys Gly Phe Tyr Lys Lys Lys Gln
                245                 250                 255

Cys Arg Pro Ser Lys Gly Arg Lys Arg Gly Phe Cys Trp Cys Val Asp
                260                 265                 270

Lys Tyr Gly Gln Pro Leu Pro Gly Tyr Thr Thr Lys Gly Lys Glu Asp
        275                 280                 285

Val His Cys Tyr Ser Met Gln Ser Lys
290                 295
```

INHIBITORS OF IGFBP3 BINDING TO TMEM219 FOR TREATMENT OF INTESTINAL DISEASES

TECHNICAL FIELD

The present invention relates to an inhibitor of IGFBP3 and uses thereof for the treatment and/or prevention of an intestinal disease, in particular of diabetic enteropathy or inflammatory bowel disease.

The present invention also relates to IGFBP3 and uses thereof for the diagnosis, prognosis or an intestinal disease, in particular of diabetic enteropathy or inflammatory bowel disease.

BACKGROUND ART

Gastrointestinal disorders, consisting of gastroparesis, abdominal distension, irritable bowel syndrome and fecal incontinence, are common in individuals with type 1 diabetes (T1D)(1993). Indeed up to 80% of individuals with long-standing T1D, who are generally affected by several diabetic complications including end stage renal disease (ESRD) (1993; Atkinson et al., 2013; Fiorina et al., 2001), show intestinal symptoms. The presence of these gastrointestinal symptoms, known as diabetic enteropathy (DE), significantly reduces the quality of life (1993; Atkinson et al., 2013; Camilleri, 2007; Talley et al., 2001) and has a largely unknown pathogenesis (Feldman and Schiller, 1983). Preclinical studies showed significant derangement of the intestinal mucosa morphology in diabetic rodents (Domenech et al., 2011; Zhao et al., 2003), suggesting that in T1D intestinal homeostasis may be altered; however, little data are available in humans. The intestinal epithelium is maintained by intestinal stem cells and their niche, which respond to physiological stress and to environmental injury (Barker, 2014; Medema and Vermeulen, 2011). Colonic stem cells (CoSCs), located at the crypt base of the large intestine and expressing the ephrin B receptor 2 (EphB2), leucine-rich repeat containing G protein-coupled receptor 5 (LGR5), h-TERT and aldehyde dehydrogenase (Aldh), among other markers (Carlone and Breault, 2012; Carpentino et al., 2009; Jung et al., 2011; Sato and Clevers, 2013), constitute with the local microenvironment the CoSC niche (van der Flier and Clevers, 2009; Zeki et al., 2011). Recent studies have established conditions that recapitulate many features of intestinal homeostasis and generate normal self-renewing large crypt organoids in vitro, or so-called "mini-guts" (Sato and Clevers, 2013). Whether systemic factors, such as circulating hormones, serve to control the CoSCs remains to be established (Stange and Clevers, 2013).

The treatment of gastrointestinal disorders, in particular diabetic enteropathy, includes symptomatic drugs and reliever medications for diarrhea, abdominal pain, constipation, and dyspepsia. Up to date there is no specific treatment available for diabetic enteropathy. The diagnosis of gastrointestinal disorders, in particular diabetic enteropathy includes colon endoscopy, gastric endoscopy, anorectal manometry, esophageal manometry and analysis of fecal samples, evaluation of peripheral cancer markers (i.e. CEA, Ca 19.9, alpha-fetoprotein, Ca125) and of celiac markers. None of the aforementioned method is capable of providing a certain diagnosis of diabetic enteropathy.

WO 2011133886 and WO2007024715 discloses a therapeutic composite in the form of a IGFBP3 binding antibody.

WO0187238 relates to an anticancer pharmaceutical composition comprising a therapeutically effective TMEM219, in particular for the treatment of colon cancer.

WO 2014089262 discloses the use of IGFBP3 as a marker of diagnosis of chronic inflammation (obesity) disorders (in particular, inflammatory bowel disease such as UC and Crohn's disease and colon cancer).

U.S. Pat. No. 6,066,464 relates to an immunoassay for the detection of IGFBP3 on a solid support that is paper.

WO2013152989 relates to the use of IGFBP3 as a biomarker of colorectal cancer.

WO0153837 discloses a method of monitoring or diagnosing disease conditions, that involve measuring a combination of tumor markers and at least one component of the IGF axis.

IGFBP3 is proposed as a marker of colon tumors.

Therefore there is the need for alternative treatments and diagnosis methods of gastrointestinal disorders, in particular diabetic enteropathy.

SUMMARY OF THE INVENTION

Whether systemic factors serve to control the homeostasis of colonic epithelium and of colonic stem cells (CoSCs) remains unclear. The inventors hypothesize that a circulating "hormonal" dyad controls CoSCs and is disrupted in long-standing type 1 diabetes (T1D) leading to diabetic enteropathy (DE). Individuals with long-standing T1D exhibited abnormalities of intestinal mucosa and CoSCs, and failure to generate in vitro mini-guts. Serum proteomic profiling revealed altered circulating levels of insulin-like growth factor 1 (IGF-I) and its binding protein-3 (IGFBP3) in 30 long-standing T1D individuals, with evidences of an increased hyperglycemia-mediated IGFBP3hepatic release. IGFBP3 prevented mini-gut growth in vitro via a TMEM219-dependent/caspase-mediated IGF-I-independent effect and disrupted CoSCs in preclinical models in vivo. The restoration of normoglycemia in long-standing T1D, with kidney-pancreas transplantation, and the treatment with an ecto-TMEM219 recombinant protein in diabetic mice, re-established CoSCs by restoring appropriate IGF-I/IGFBP3 circulating levels. The peripheral IGF-I/IGFBP3 dyad controls CoSCs and is dysfunctional in DE.

Here the inventors demonstrate that individuals with long-standing T1D and DE have altered CoSCs and show increased levels of IGFBP3. Administration of IGFBP3 alters CoSC regenerative properties and mucosa morphology in vitro and in vivo, in a preclinical model of DE, by quenching circulating IGF-I and by exerting a TMEM219-dependent/caspase-mediated toxic effect on CoSCs.

Further, altered IGFBP3/IGF-I ratio was found in patients with inflammatory bowel disease. A new ecto-TMEM219 recombinant protein, based on the extracellular domain of the IGFBP3 receptor (TMEM219) was generated. ecto-TMEM219 quenches peripheral IGFBP3 and prevents its binding to IGFBP3 receptor, TMEM219. Then, targeting IGFBP3 with such ecto-TMEM219 recombinant protein, expressed on CoSCs, abrogates IGFBP3 deleterious effects in vitro and in vivo.

Intestinal disorders include diabetic enteropathy, inflammatory bowel diseases, irritable bowel disease and celiac disease.

Symptoms reported in individuals with diabetic enteropathy are similar to those reported in other intestinal disorders, therefore the role of intestinal stem cells (ISCs) in various colorectal diseases has been investigated in a number of studies (Table I-A below). Table I-A: intenstinal stem cells (ISCs) and gastro-intestinal disorders

TABLE I-A intestinal stem cells (ISCs) and gastro-intestinal disorders

| Type of GI disorder | Role of ISCs | Main Findings | Refs |
|---|---|---|---|
| Inflammatory bowel diseases (IBD) | Defects in ISC differentiation | Impaired generation of Paneth and goblet cells leads to a defective anti-microbial mucosal barrier | 1, 2 |
| Celiac disease (CD) | Depletion of ISCs | ISCs favor mucosal healing and clinical remission; ISC altered signaling and deficiency favors CD | 3, 4 |
| Helicobacter Pilory (HP) gastritis | Manipulation of ISCs, Colonization of ISCs | HP colonize and alter turnover of gastric ISCs, favoring glandular hyperplasia | 5 |
| Pre-cancerous conditions (adenoma, chronic ulcerative colitis, polyposis) | Overpopulation of ISCs | In pre-cancerous conditions, ISC differentiation and turnover are abrogated, resulting in increased numbers of ISCs | 6 |
| Diabetic enteropatby (DE) | Depletion of ISCs Disruption of ISCs | IGFBP3 mediates ISC apoptosis in DE | 7 |

Abbreviations: GI, gastrointestinal; ISCs, intestinal stem cells; IBD, inflammatory bowel disease; CC, colorectal cancer; CD, celiac disease; HP, Helicobacter pilory; DE, diabetic enteropathy.
References: 1. Gersemann M, et al, 2011; 17: 3198-203, 2. Schonhoff SE, et al., 2004, 3. Piscaglia AC, et al. 2015; 4. Senger S, et al., 2015; 5. Bartfeld S, et al. 2015, 6. Boman BM, et al., 2008; 7. D'Addio F, et al., 2015.

Alterations in ISC regulation and in crypt and epithelial self-renewal properties have been described in IBD[10], in colon pre-cancerous conditions[11], and in colorectal cancer[4]. Recently, it has also been suggested that ISCs may be depleted in active celiac disease (CD), thus leading to impaired regeneration of the intestinal epithelial compartment, which may account for the disappearance of villi[5]. Considering that IGFBP3 has been demonstrated to target the colonic stem cells (CoSCs), a particular subset of ISCs located in the colonic crypts, through its binding to TMEM219, the IGFBP3 receptor, thus mediating the onset of diabetic enteropathy, it is argued that this detrimental effect may be exerted also on CoSCs in other intestinal disorders, as the aforementioned ones. Therefore, the inhibition of the TMEM219/IGFBP3 axis may represent a strategy that preserves CoSCs and ISCs from the IGFBP3-mediated detrimental effects in all intestinal disorders that may originate from a dysregulation of ISCs or CoSCs.

Therefore the present invention provides an inhibitor of IGFBP3 for use in the treatment and/or prevention of an intestinal disorder.

Preferably the inhibitor is an inhibitor of the IGFBP3/TMEM219 axis.

Preferably said inhibitor inhibits or blocks the interaction of IGFBP3 with its receptor TMEM219 (also named IGFBP3-receptor) or wherein said inhibitor inhibits or blocks the interaction of IGFBP3 with IGF-I or wherein said inhibitor inhibits or blocks IGFBP3 function.

Preferably said inhibitor is selected from the group consisting of:
 a) a polypeptide;
 b) a polynucleotide coding for said polypeptide or a polynucleotide able to inhibit or block the interaction of IGFBP3 with its receptor TMEM219 or able to inhibit or block the interaction of IGFBP3 with GF 1 or able to inhibit or block IGFBP3 expression and/or function;
 c) a vector comprising or expressing said polynucleotide;
 d) a host cell genetically engineered expressing said polypeptide or said polynucleotide;
 e) a small molecule;
 f) a peptide, a protein, an antibody, an antisense oligonucleotide, a siRNA, antisense expression vector or recombinant virus or any other agent able to inhibit or block the interaction of IGFBP3 with its receptor TMEM219 or able to inhibit or block the interaction of IGFBP3 with GF 1 or able to inhibit or block IGFBP3 expression and/or function.

Still preferably said inhibitor is the receptor TMEM219 or a fragment thereof. Preferably the fragment of TMEM219 is a fragment of the extracellular domain of TMEM219.

In a preferred embodiment the inhibitor is ecto-TMEM219.

The inhibitor may be a fusion protein comprising IGFBP3.

In a preferred embodiment the inhibitor is an antibody, preferably an IGFBP3-blocking antibody, preferably a TMEM219-blocking antibody, preferably an IGF-I-blocking antibody.

In a preferred embodiment the intestinal disorder is selected from the group consisting of: malabsorption syndromes, celiac disease, irritable bowel syndrome, inflammatory bowel disease, cachexia, diabetic enteropathy.

Preferably the intestinal disorder is diabetic enteropathy or inflammatory bowel disease (ulcerative colitis and Crohn's disease). Preferably the intestinal disorder is celiac disease.

Inflammatory bowel disease (IBD) involves chronic inflammation of all or part of the digestive tract. IBD primarily includes ulcerative colitis and Crohn's disease. Both usually involve severe diarrhea, pain, fatigue and weight loss. IBD can be debilitating and sometimes leads to life threatening complications. Ulcerative colitis is an inflammatory bowel disease that causes long lasting inflammation and sores (ulcers) in the innermost lining of the large intestine (colon) and rectum. Crohn's disease is an IBD that causes inflammation of the lining of the digestive tract. In Crohn's disease, inflammation often spreads deep into affected tissues. The inflammation can involve different areas of the digestive tract—the large intestine, small intestine or both.

Celiac disease, also known as gluten-sensitive enteropathy, is a chronic disease of the upper digestive caused by an immunologically mediated, inflammatory reaction to ingested gliadin.

Gliadin is a component of gluten, a protein found in grains such as wheat, rye, and barley.

Such inflammatory response damages the intestinal mucosa resulting in maldigestion and malabsorption.

In a further aspect the invention provides a pharmaceutical composition for use in the treatment and/or prevention of an intestinal disorder comprising the inhibitor as defined above and pharmaceutically acceptable carriers.

In a further aspect the invention provides a method for the diagnosis of an intestinal disorder in a subject comprising:
a) measuring the amount of the protein IGFBP3 or the amount of the polynucleotide coding for said protein in a biological sample obtained from the subject;
b) comparing the measured quantity of the protein IGFBP3 or measured quantity of the polynucleotide coding for said protein to a control amount, wherein if the measured quantity is higher than the control amount, the subject is diagnosed with the intestinal disorder.

Preferably the quantity of IGFBP3 is measured by an antibody.

Preferably the biological sample is selected from the group consisting of: serum, urine, cell culture supernatant.

Still preferably the intestinal disorder is selected from the group consisting of: malabsorption syndromes, irritable bowel disease, inflammatory bowel disease, cachexia, diabetic enteropathy.

Yet preferably the intestinal disorder is diabetic enteropathy.

In a further aspect the invention provides a kit for the diagnosis of an intestinal disorder comprising means to measure the amount of the protein IGFBP3 and/or means to measure the amount of the polynucleotide coding for said protein and optionally, control means. The above diagnosis method may also comprise a step of treating the subject, in particular the treatment may be an inhibitor of IGFBP3 as defined in the present invention or an existing treatment for an intestinal disorder such as anti-inflammatory agents (e.g. aminosalicyl-derivatives such as mesalazin, sulfasalazine), corticosteroids, immunosuppressive treatments (azothioprine, mercaptopurine, methotrexate, cyclosporine, micophenolate mofetil, natalizumab, vedolizumab), TNF-alpha blockers (infliximab, adalimumab, certolizumab, golimumab), antibiotics (e.g. metronidazole and ciprofloxacin), probiotics, integrin alpha inhibitors.

In the present invention an intestinal disorder comprises gastro-intestinal disorder, malabsorption syndromes, diabetic enteropathy, cachexia, celiac disease, irritable bowel syndromes, and inflammatory bowel diseases. In the present invention an intestinal disorder does not include colorectal cancers.

In the present invention "inhibits or blocks IGFBP3 function" means quenching circulating IGFBP3 and preventing its binding to IGFBP3 receptor, TMEM219, in order to halt IGFBP3 proapoptotic effect on CoSCs and colonic crypts. Such inhibition or blocking may be achieved by a fusion protein comprising IGFBP3. The expression of IGFBP3 may be measured by means of RT-PCR on tissues and cells, Western blot on tissues and cells, Immunohistochemistry on tissues.

Levels of IGFBP3 in biological fluids can be measured by immune-targeted assays and proteomic analysis.

The function of IGFBP3 may be measured by means of detecting Caspases 8 and 9 expression on target cells using RT-PCR, microarrays, by co-culturing target cells/structures with Pan Caspase inhibitor, Caspases 8 and 9 inhibitors and measuring live cells/structures.

In the present invention "inhibits or blocks the interaction of IGFBP3 with IGF-I" means removing free IGFBP3 from the circulation in order to prevent its binding to free IGF-I.

The interaction of IGFBP3 with IGF-I may be measured by means of evaluating IGF-I free levels in the circulation and/or IGFBP3 levels in the circulation.

In the present invention "inhibit or block the interaction of IGFBP3 with its receptor TMEM219" means quenching circulating IGFBP3 and preventing its binding to TMEM219 receptor expressed on CoSCs. The IGFBP3-TMEM219 binding could be prevented also by the use of an IGFBP3-blocking antibody. In addition, a TMEM219 blocking antibody could bind TMEM219 receptor thus rendering the receptor unavailable when IGFBP3 comes from the circulation.

In the present invention inhibiting the IGFBP3/TMEM219 axis means blocking IGFBP3 binding to TMEM219, for instance by quenching IGFBP3 from the circulation, it also means blocking the IGFBP3-binding site of TMEM219, blocking IGFBP3 binding site on TMEM219. It further means inhibiting TMEM219 function and/or expression and/or signaling, this may be achieved for instance by silencing TMEM219 expression, in particular with SiRNA or oligonucleotides. It also means inhibiting the function and/or expression of IGFBP3.

According to the invention, an inhibitor of IGFBP3 binding to TMEM219 can be one of the following molecules:
Soluble Ecto-TMEM219 (extracellular portion of TMEM219) which neutralizes circulating IGFBP3;
Fusion protein TMEM219-Ig, an Fc-based fusion protein composed of an immunoglobulin Fc domain that is directly linked to TMEM219 peptide or to its extracellular portion, which quenches circulating IGFBP3 and prevents its binding to TMEM219 expressed on beta cells;
Anti-IGFBP3 antibody that selectively blocks the TMEM219-binding site;
Anti-TMEM219 antibody, which occupies the IGFBP3 binding site of TMEM219 receptor thus preventing IGFBP3 binding (having antagonistic activity with respect to IGFBP3)
Oligonucleotides complementary to IGFBP3 mRNA The inhibitor of the invention may be the receptor TMEM219

(MGNCQAGHNLHLCLAHHPPLVCATLILLLLGLSGLGLGSFLLTHRTGLR

SPDIPQDWVSFLRSFGQLTLCPRNGTVTGKWRGSHVVGLLTTLNFGDGPD

RNKTRTFQATVLGSQMGLKGSSAGQLVLITARVTTERTAGTCLYFSAVPG

ILPSSQPPISCSEEGAGNATLSPRMGEECVSVWSHEGLVLTKLLTSEELA

LCGSRLLVLGSFLLLFCGLLCCVTAMCFHPRRESHWSRTRL,

SEQ ID NO: 1)

or a fragment thereof.

In particular the fragment of TMEM219 is designed such as to block/prevent IGFBP3 access and/or binding to TMEM219, it has a smaller molecular weight, it contains five cysteines that form disulfide bridges and a globular structure. Preferably the fragment is at least 50 amino acid long, preferably 100 amino acid long, still preferably 120 amino acid long, yet preferably 150 amino acid long, preferably at least 160 amino acid long.

In a preferred embodiment the fragment is at least 162, 165, 170, 175, 180, 185, 190, 195, 200, 205, 210, 215, 220, 225, 230, 235 amino acid long. Preferably the fragment has at least 65% identity with the sequence of TMEM219, preferably at least 70%, 75%, 80%, 85%, 90%, 95% or 99% identity with the sequence of TMEM219.

Preferably the fragment of TMEM219 is a fragment of an extracellular domain of TMEM219, in particular the fragment comprises the sequence:

(SEQ ID NO: 2)
THRTGLRSPDIPQDWVSFLRSFGQLTLCPRNGTVTGKWRGSHVVGLLTT

LNFGDGPDRNKTRTFQATVLGSQMGLKGSSAGQLVLITARVTTERTAGT

CLYFSAVPGILPSSQPPISCSEEGAGNATLSPRMGEECVSVWSHEGL V

LTKLLTSEELALCGSR.

Preferably the fragment of TMEM219 is an extracellular domain of TMEM219, in particular the fragment comprises the sequence:

(SEQ ID NO: 3)
SFLLTHRTGLRSPDIPQDWVSFLRSFGQLTLCPRNGTVTGKWRGSHVVGL

LTTLNFGDGPDRNKTRTFQATVLGSQMGLKGSSAGQLVLITARVTTERTA

GTCLYFSAVPGILPSSQPPISCSEEGAGNATLSPRMGEECVSVWSHEGLV

L TKLLTSEELALCGSR.

Preferably the fragment of TMEM219 consists of:

THRTGLRSPDIPQDWVSFLRSFGQLTLCPRNGTVTGKWRGSHVVGLLTTL

NFGDGPDRNKTRTFQATVLGSQMGLKGSSAGQLVLITARVTTERTAGTCL

YFSAVPGILPSSQPPISCSEEGAGNATLSPRMGEECVSVWSHEGLVLTKL

LTSEELALCGSR (SEQ ID NO: 2).

Preferably the fragment of TMEM219 consists of:

(SEQ ID NO: 3)
SFLLTHRTGLRSPDIPQDWVSFLRSFGQLTLCPRNGTVTGKWRGSHVVGL

LTTLNFGDGPDRNKTRTFQATVLGSQMGLKGSSAGQLVLITARVTTERTA

GTCLYFSAVPGILPSSQPPISCSEEGAGNATLSPRMGEECVSVWSHEGL

VL TKLLTSEELALCGSR.

In the present invention TMEM219 is preferably eukaryote TMEM219, preferably a mammal TMEM219, still preferably human TMEM219.

The interaction of IGFBP3 with TMEM219 may be measured by means of indirect assessment of the effects of IGFBP3 on target cells (increased Caspase 8 and 9 expression with RT-PCR), direct assessment of IGFBP3-IGFBP3-receptor (TMEM219) binding with Liquid or Solid Phase Ligand Binding Assays (i.e. immunoprecipitation, RT-PCR, immunoassays) and Non-radioactive Ligand Binding Assays.

In the present invention "long-standing T1D" means a history of type 1 diabetes longer than 15 years associated with the development of diabetic complications.

In a preferred aspect of the invention, the inhibitor is an antibody or synthetic or recombinant derivative thereof. Said antibody is preferably a monoclonal or polyclonal antibody, or synthetic or recombinant derivatives thereof, more preferably said antibody being a humanized monoclonal antibody.

Preferably, said polynucleotide is a RNA or DNA, preferably a siRNA, a shRNA, a microRNA or an antisense oligonucleotide.

In a preferred embodiment, the above vector is an expression vector selected from the group consisting of: plasmids, viral particles and phages.

Preferably, said host cell is selected from the group consisting of: bacterial cells, fungal cells, insect cells, animal cells, plant cells, preferably being an animal cell, more preferably a human cell.

In a preferred embodiment, the inhibitor as above defined (a) is combined with at least one therapeutic agent (b) to define a combination or combined preparation. The therapeutic agent may be an anti-diabetic agent, a pain reliever, medication for diarrhea or any other treatment for an intestinal disorder in particular diabetic enteropathy.

Examples of therapeutic agent are: insulin therapy, in any form; pramlintide; angiotensin-converting enzyme inhibitors or angiotensin II receptor blockers (ARBs); aspirin, anticoagulation and platelet anti-aggregation agents; cholesterol-lowering drugs; other blood pressure lowering agents; oral anti-diabetic agents like metformin, sulfonylureas (glyburide, glipizide and glimepiride, meglitinides (repaglinide and nateglinide), thiazolidinediones (Rosiglitazone and pioglitazone), DPP-4 inhibitors (sitagliptin, saxagliptin and linagliptin), GLP-1 receptor agonists (Exenatide and liraglutide), SGLT2 inhibitors (e.g. canagliflozin and dapagliflozin); anti-inflammatory agents (e.g. aminosalicyl-derivatives such as mesalazin, sulfasalazine); corticosteroids; immunosuppressive treatments (azothioprine, mercaptopurine, methotrexate, cyclosporine, micophenolate mofetil) integrin inhibitors (natalizumab, vedolizumab); TNF-alpha blockers (infliximab, adalimumab, certolizumab, golimumab), antibiotics (e.g. metronidazole and ciprofloxacin); probiotics.

The terms "combination" and "combined preparation" as used herein also define a "kit of parts" in the sense that the combination partners (a) and (b) as defined above can be dosed independently or by use of different fixed combinations with distinguished amounts of the combination partners (a) and (b), i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g. in order to cope with the needs of a patient sub-population to be treated or the needs of the single.

The combination therapy may result in unexpected improvement in the treatment of intestinal diseases. When administered simultaneously, sequentially or separately, the inhibitor and the other therapeutic agent may interact in a synergistic manner to reduce intestinal disease. This unexpected synergy allows a reduction in the dose required of each compound, leading to a reduction in the side effects and enhancement of the clinical effectiveness of the compounds and treatment.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients renders impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between intestinal disease models and effects seen in man suggest that synergy in animals may be demonstrated in the models as described in the Examples below.

The above pharmaceutical compositions are preferably for systemic, oral, locally, preferably rectally, or topical administration.

Control means can be used to compare the amount or the increase of amount of the compound as above defined to a proper control. The proper control may be obtained for example, with reference to known standard, either from a normal subject or from normal population.

The means to measure the amount of at least one compound as above defined are preferably at least one antibody, functional analogous or derivatives thereof. Said antibody, functional analogous or derivatives thereof are specific for said compound.

In a preferred embodiment, the kit of the invention comprises:

a solid phase adhered antibody specific for said compound;

detection means of the ligand specific-biomarker complex.

The kits according to the invention can further comprise customary auxiliaries, such as buffers, carriers, markers, etc. and/or instructions for use.

The proper control may be a sample taken from a healthy patient or from a patient affected by a disorder other than intestinal disease.

In the case of a method or a kit for monitoring the progression of the intestinal disease, the progress of the disease is monitored and the proper control may be a sample taken from the same subject at various times or from another patient, and the proper control amount may by the amount of the same protein or polynucleotide measured in a sample taken from the same subject at various times or from another patient.

In the case of a method or a kit for monitoring the efficacy of a therapeutic treatment, the proper control may be a sample taken from the same subject before initiation of the therapy or taken at various times during the course of the therapy and the proper control amount may be the amount of the same protein or polynucleotide measured in a sample taken from the same subject before initiation of the therapy or taken at various times during the course of the therapy.

In the present invention, the expression "measuring the amount" can be intended as measuring the amount or concentration or level of the respective protein and/or mRNA thereof and/or DNA thereof, preferably semi-quantitative or quantitative. Measurement of a protein can be performed directly or indirectly. Direct measurement refers to the amount or concentration measure of the biomarker, based on a signal obtained directly from the protein, and which is directly correlated with the number of protein molecules present in the sample. This signal—which can also be referred to as intensity signal—can be obtained, for example, by measuring an intensity value of a chemical or physical property of the biomarker. Indirect measurements include the measurement obtained from a secondary component (e.g., a different component from the gene expression product) and a biological measurement system (e.g. the measurement of cellular responses, ligands, "tags" or enzymatic reaction products).

The term "amount", as used in the description refers but is not limited to the absolute or relative amount of proteins and/or mRNA thereof and/or DNA thereof, and any other value or parameter associated with the same or which may result from these. Such values or parameters comprise intensity values of the signal obtained from either physical or chemical properties of the protein, obtained by direct measurement, for example, intensity values in an immunoassay, mass spectroscopy or a nuclear magnetic resonance. Additionally, these values or parameters include those obtained by indirect measurement, for example, any of the measurement systems described herein. Methods of measuring mRNA and DNA in samples are known in the art. To measure nucleic acid levels, the cells in a test sample can be lysed, and the levels of mRNA in the lysates or in RNA purified or semi-purified from lysates can be measured by any variety of methods familiar to those in the art. Such methods include hybridization assays using detectably labeled DNA or RNA probes (i.e., Northern blotting) or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled (e.g., fluorescent, or enzyme-labeled) DNA or RNA probes. Additional methods for quantifying mRNA include RNA protection assay (RPA), cDNA and oligonucleotide microarrays, representation difference analysis (RDA), differential display, EST sequence analysis, and serial analysis of gene expression (SAGE).

If by comparing the measured amount of the protein IGFBP3 or of the polynucleotide coding for said protein with the amount obtained from a control sample, the amount of said compound in the sample isolated from the subject corresponds to a higher value, the subject may present the disease or go towards an aggravation of said disease.

If by comparing the measured amount of the protein IGFBP3 or of the polynucleotide coding for said protein with the amount obtained from a control sample, the amount of said compound in the sample isolated from the subject corresponds to a similar or lower value, the subject may be not affected by the disease or go toward an amelioration of the disease, respectively.

Alternatively, the expression "detection" or "measuring the amount" is intended as measuring the alteration of the molecule. Said alteration can reflect an increase or a decrease in the amount of the compounds as above defined. An increase of the protein IGFBP3 or of the polynucleotide coding for said protein can be correlated to an aggravation of the disease. A decrease in the protein IGFBP3 or of the polynucleotide coding for said protein can be correlated to an amelioration of the disease or to recovery of the subject.

The expression "protein IGFBP3" or "IGFBP3" or "TMEM219" is intended to include also the corresponding protein encoded from a IGFBP3 or TMEM orthologous or homologous genes, functional mutants, functional derivatives, functional fragments or analogues, isoforms thereof.

The expression "gene IGFBP3" or "IGFBP3" or "gene TMEM219" or "TMEM219" is intended to include also the corresponding orthologous or homologous genes, functional mutants, functional derivatives, functional fragments or analogues, isoforms thereof.

In the present invention "functional mutants" of the protein are mutants that may be generated by mutating one or more amino acids in their sequences and that maintain their activity for the treatment of intestinal disease. Indeed, the protein of the invention, if required, can be modified in vitro and/or in vivo, for example by glycosylation, myristoylation, amidation, carboxylation or phosphorylation, and may be obtained, for example, by synthetic or recombinant techniques known in the art. The protein of the invention "IGFBP3" or "TMEM219" may be modified to increase its bioavailability or half-life by know method in the art. For instance the protein may be conjugated to a polymer, may be pegylated etc.

In the present invention the active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as injectable microspheres composed of lactic acid-glycolic acid copolymer and leuprolide acetate, and poly-d-(—)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In the present invention "functional" is intended for example as "maintaining their activity" e.g. therapeutic treatment of intestinal disease.

The term "analogue" as used herein referring to a protein means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide.

The term "derivative" as used herein in relation to a protein means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. As used herein, the term "derivatives" also refers to longer or shorter polypeptides having e.g. a percentage of identity of at least 41%, preferably at least 41.5%, 50%, 54.9%, 60%, 61.2%, 64.1%, 65%, 70% or 75%, more preferably of at least 85%, as an example of at least 90%, and even more preferably of at least 95% with IGFBP3, or with an amino acid sequence of the correspondent region encoded from a IGFBP3 orthologous or homologous gene.

As used herein "fragments" refers to polypeptides having preferably a length of at least 10 amino acids, more preferably at least 15, at least 17 amino acids or at least 20 amino acids, even more preferably at least 25 amino acids or at least 37 or 40 amino acids, and more preferably of at least 50, or 100, or 150 or 200 or 250 or 300 or 350 or 400 or 450 or 500 amino acids. According to the present invention, an "effective amount" of a composition is one that is sufficient to achieve a desired biological effect, in this case an amelioration or the treatment of an intestinal disorder or disease.

It is understood that the effective dosage will be dependent upon the age, sex, health, and weight of the recipient, kind of concurrent treatment, if any, frequency of treatment, and the nature of the effect desired. The provided ranges of effective doses of the inhibitor or molecule of the invention (e.g. from 1 mg/kg to 1000 mg/kg, in particular systemically administered) are not intended to limit the invention and represent preferred dose ranges. However, the preferred dosage can be tailored to the individual subject, as is understood and determinable by one of skill in the art, without undue experimentation.

The administration of oligonucleotides of the present invention may be carried out by known methods, wherein a nucleic acid is introduced into a desired target cell in vitro or in vivo.

An aspect of the present invention comprises a nucleic acid construct comprised within a delivery vehicle. A delivery vehicle is an entity whereby a nucleotide sequence can be transported from at least one media to another. Delivery vehicles may be generally used for expression of the sequences encoded within the nucleic acid construct and/or for the intracellular delivery of the construct. It is within the scope of the present invention that the delivery vehicle may be a vehicle selected from the group of RNA based vehicles, DNA based vehicles/vectors, lipid based vehicles, virally based vehicles and cell based vehicles. Examples of such delivery vehicles include: biodegradable polymer microspheres, lipid based formulations such as liposome carriers, coating the construct onto colloidal gold particles, lipopolysaccharides, polypeptides, polysaccharides, pegylation of viral vehicles.

In one embodiment of the present invention may comprise a virus as a delivery vehicle, where the virus may be selected from: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art. Commonly used gene transfer techniques include calcium phosphate, DEAE-dextran, transfection, electroporation and microinjection and viral methods. Another technique for the introduction of DNA into cells is the use of cationic liposomes. Commercially available cationic lipid formulations are e.g. Tfx 50 (Promega) or Lipofectamin 2000 (Life Technologies).

The compositions of the present invention may be in form of a solution, e.g. an injectable solution, a cream, ointment, tablet, suspension or the like. The composition may be administered in any suitable way, e.g. by injection, particularly by intraocular injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes.

The recombinant expression vector of the invention can be any suitable recombinant expression vector, and can be used to transform or transfect any suitable host. Suitable vectors include those designed for propagation and expansion or for expression or both, such as plasmids and viruses. The recombinant expression vectors of the invention can be prepared using standard recombinant DNA techniques. Constructs of expression vectors, which are circular or linear, can be prepared to contain a replication system functional in a prokaryotic or eukaryotic host cell. Replication systems can be derived, e.g., from CoIE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes. The recombinant expression vector can comprise a native or normative promoter operably linked to the nucleotide sequence encoding the PCYOX1 inhibitor (including functional portions and functional variants thereof), or to the nucleotide sequence which is complementary to or which hybridizes to the nucleotide sequence encoding the RNA. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. In the above IGFBP3 compositions further materials as well as processing techniques and the like may be set out in Part 5 of Remington's Pharmaceutical Sciences, 20th Edition, 2000, Merck Publishing Company, Easton, Pa., which is incorporated herein by reference.

The compounds of this invention can also be administered in sustained release forms or from sustained release drug delivery systems. A description of representative sustained release materials can also be found in the incorporated materials in Remington's Pharmaceutical Sciences. Furthermore, pharmaceutical formulations can be prepared using a process, which is generally known in the pharmaceutical art.

In the present invention, when the molecule of the invention is administered with another therapeutic agent, it may be administered simultaneously or sequentially.

Sequences

Amino Acid Sequence of IGFBP3:

(SEQ ID NO. 4)
MQRARPTLWAAALTLLVLLRGPPVARAGASSAGLGPVVRCEPCDARALAQ

CAPPPAVCAELVREPGCGCCLTCALSEGQPCGIYTERCGSGLRCQPSPDE

ARPLQALLDGRGLCVNASAVSRLRAYLLPAPPAPGEPPAPGNASESEEDR

SAGSVESPSVSSTHRVSDPKFHPLHSKIIIIKKGHAKDSQRYKVDYESQS

TDTQNFSSESKRETEYGPCRREMEDTLNHLKFLNVLSPRGVHIPNCDKKG

FYKKKQCRPSKGRKRGFCWCVDKYGQPLPGYTTKGKEDVHCYSMQSK.

Nucleotide Sequence of IGFBP3:
Homo sapiens insulin-like growth factor binding protein 3 (IGFBP3), RefSeqGene on chromosome 7, NCBI Reference Sequence: NG_011508.1.

mRNA Sequence of IGFBP3:
Homo sapiens insulin-like growth factor binding protein 3 (IGFBP3), transcript variant 1, mRNA, NCBI Reference Sequence: NM_001013398.1.

Amino Acid Sequence of TMEM219:

(SEQ ID NO. 1)
MGNCQAGHNLHLCLAHHPPLVCATLILLLLGLSGLGLGSFLLTHRTGLRS

PDIPQDWVSFLRSFGQLTLCPRNGTVTGKWRGSHVVGLLTTLNFGDGPDR

NKTRTFQATVLGSQMGLKGSSAGQLVLITARVTTERTAGTCLYFSAVPGI

LPSSQPPISCSEEGAGNATLSPRMGEECVSVWSHEGLVLTKLLTSEELAL

CGSRLLVLGSFLLLFCGLLCCVTAMCFHPRRESHWSRTRL.

Nucleotide Sequence of TMEM219:
TMEM219 transmembrane protein 219 [*Homo sapiens* (human)], Gene ID: 124446.

mRNA Sequence of TMEM219:
*Homo sapiens* transmembrane protein 219 (TMEM219), transcript variant 1, mRNA, NCBI Reference Sequence: NM_001083613.1

The present invention will be illustrated by means of non-limiting examples in reference to the following figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1R. Diabetic enteropathy in long-standing T1D is characterized by intestinal mucosa abnormalities and impairment in the colonic stem cells. FIGS. 1A-1C are bar graphs depicting the score of diarrhea, abdominal pain and constipation according to the administration of the GSRS questionnaire in healthy subjects (CTRL) and long-standing T1D individuals (T1D+ESRD). Gray area indicates normal range for the parameter. FIGS. 1G, 1I, 1K, 1M, 1O are representative images of hematoxylin and eosin (H&E) histology staining, immunostained MIB 1+cells, ultrastructural analysis of neural structures with red arrows indicating localization and presence of neuroendocrine vesicles, immunostained 5HT$^+$, aldehyde dehydrogenase (Aldh)$^+$ cells, and EphB2$^+$ expression, on bioptic samples obtained from healthy subjects (CTRL) and long-standing T1D individuals (T1D+ESRD). Ultrastructural analysis scale bar: 2000 nm. Original magnification: 100× in FIG. 1G, panels labeled G1-G2; 400× in FIG. 1I, panels labeled 11-12, FIG. 1K, panels labeled K1-K2; 40× in FIG. 1O, panels labeled O1-O2; 200×, in FIG. 1Q, panels labeled Q1-Q2. Scale bar 80 micron. FIGS. 1H, 1J, 1L, 1N, 1P, 1R are bar graphs reporting the measurement of crypts, MIB1$^+$ cells, of neuroendocrine vesicles of nerve terminals (number of cases with >3 NE vesicles detected per nerve terminal), of 5HT$^+$, Aldh$^+$ cells, and of EphB2$^+$ expression (intensity score 0-5) in CTRL and long-standing T1D subjects (T1D+ESRD). N=20 CTRL and n=60 T1D+ESRD individuals were included in the evaluation. Data are expressed as mean±standard error of the mean (SEM) unless differently reported. *p<0.01; p<0.001; *p<0.0001. Abbreviations: GSRS, Gastrointestinal Symptom Rating Scale; CoSC, intestinal stem cell; T1D, type 1 diabetes; ESRD, end stage renal disease; CTRL, healthy subjects; H&E, hematoxylin and eosin; MIB 1, antibody against Ki67; EphB2, Ephrin B receptor 2; Aldh, Aldehyde dehydrogenase; 5HT, serotonin; NE, neuroendocrine vesicles.

FIGS. 2A-2N. Diabetic enteropathy in long-standing T1D is associated with a defect in CoSCs. FIGS. 2A-2B are representative flow dot plots of EphB2$^{low}$, EphB2$^{medium}$ and EphB2$^+$ cells in healthy subjects (CTRL) and long-standing T1D individuals (T1D+ESRD). FIGS. 2C-2E are bar graphs depicting results of flow cytometric analysis of EphB2$^{hi+}$, EphB2$^{hi+}$LGR5$^+$ and EphBi$^+$h-TERT$^+$ cells in freshly isolated crypts (n=10 CTRL and n=10 T1D+ESRD). FIGS. 2F-2H are bar graphs depicting expression data of CoSC markers EphB2, LGR5, h-TERT as normalized mRNA expression measured by quantitative RT-PCR on isolated intestinal crypts. All samples were run in triplicate and normalized to expression of the housekeeping gene ACTB (ΔΔCt). FIG. 2J provides representative images of mini-guts cultured for 8 days in vitro obtained from previously isolated crypts of long-standing T1D individuals (T1D+ESRD) and healthy subjects (CTRL). 10× magnification. Scale bar 50 micron. FIG. 2K is a bar graph depicting the % of developed mini-guts of the total at 8 days of culture of freshly isolated intestinal crypts from n=10 CTRL and n=10 T1D+ESRD individuals. FIG. 2L provides representative images of mini-guts obtained from previously isolated crypts of healthy subjects (CTRL) and cultured for 8 days in the following conditions: L1=normal (FBS) serum+normal glucose (5 mM); L2=T1D+ESRD serum+ normal glucose; L3=normal serum+high glucose (35 mM); L4=T1D+ESRD serum+high glucose. 10× magnification. Scale bar 50 micron. FIG. 2M is a bar graph grouping % of developed mini-guts of the total at 8 days of culture from freshly isolated intestinal crypts cultured with the following conditions: normal (FBS) serum+normal glucose (5 mM); T1D+ESRD serum+normal glucose; normal serum+high glucose (35 mM); T1D+ESRD serum+high glucose. Statistical significance has been calculated within each group (normal glucose+normal serum, medium+high glucose, medium+long-standing T1D serum, high glucose+long-standing T1D serum) by comparing different culturing conditions. Comparison in the bar graph refers to all conditions vs. normal serum+normal glucose. FIG. 2N is a transcriptome profiling depicting CoSC signature markers expression in isolated crypts obtained from healthy subjects and cultured with/without high glucose and/or long-standing T1D serum. N=10 subjects per group were evaluated. Data are expressed as mean±standard error of the mean (SEM) unless differently reported. *p<0.01; p<0.001; *p<0.0001. Abbreviations: CoSC, colonic stem cell; T1D, type 1 diabetes; ESRD, end stage renal disease; CTRL, healthy subjects; EphB2, Ephrin B receptor 2; LGR5, leucine-rich repeat containing G protein-coupled receptor 5; RT-PCR, real-time polymerase chain reaction; ACTB, beta actin; FBS, fetal bovine serum.

FIGS. 3A-3M. Circulating IGF-I and IGFBP3 are altered in long-standing T1D and its manipulation in vitro induces profound effects on CoSC growth and self-renewal. FIG. 3A is a heat map representing the proteomic profile in long-standing T1D (T1D+ESRD) as compared to healthy subjects (CTRL). The complete dataset of identified and quantified proteins was subjected to statistical analysis (p<0.01). Significantly differentially expressed proteins were further analyzed through hierarchical clustering. Sera of n=10 CTRL and n=10 T1D+ESRD individuals were analyzed. FIG. 3B is a bar graph depicting LFQ intensity for a single protein extrapolated from the untargeted proteomic analysis, insulin-like growth factor binding protein 3 (IGFBP3). FIG. 3C provides representative images (40× magnification) of IGFBP3 expression in the liver. IGFBP3 is mildly and diffusely expressed in the liver parenchyma from health subjects (FIG. 3C, panel labeled C1), while it is more zonally positive in long-standing diabetic individuals (FIG. 3C, panel labeled C2). FIG. 3D is a bar graph representing IGFBP3 levels measured by ELISA in the supernatants of immortalized human hepatoma cell line (HuH-7) cultured for 5 days at different glucose concentrations (35 mM: high glucose; 20 mM: intermediate glucose; 5 mM: normal glucose). Experiments were run in triplicate. FIG. 3E is a bar graph representing insulin-like growth factor 1 (IGF-I) levels measured by ELISA in serum of healthy subjects and long-standing T1D (T1D+ESRD). FIG. 3F is a Western blot analysis (cropped blots) confirmed IGF-IR and TMEM219 expression on the intestinal crypt surface. Evaluation of total IGF-IR expression by WB includes the detection of IGF-IRα, a subunit of IGF-IR whole protein. Representative pictures of TMEM219 in situ hybridization (see, FIG. 3G, panel G1 shows negative control, panel G2 shows TMEM219 staining) performed on rectal mucosa biopsy samples obtained from CTRL. 20× magnification. FIG. 3G provides representative pictures of TMEM219 in situ hybridization (panel G1 shows negative control, panel G2 shows TMEM219 staining) performed on rectal mucosa biopsy samples obtained from CTRL. Magnification 400×. FIG. 3H is a bar graph depicting normalized mRNA expression of TMEM219 (IGFBP3 receptor) using the ΔΔ method. N=5 subjects per group were evaluated. FIG. 3I is a bar graph grouping % of developed mini-guts of the total obtained from long-standing T1D individuals in different conditions and showing the effect of IGF-I, IGFBP3 and anti-IGF-IR. The p values are relative to baseline conditions and addition of IGF-I to culture. FIG. 3J is a bar graph representing normalized mRNA expression of Caspase 8 and 9 in crypts isolated from healthy subjects cultured in the presence of IGFBP3 and IGF-I+IGFBP3, performed in triplicate. FIG. 3K is a bar graph grouping % of developed mini-guts of the total at 8 days of culture, obtained from healthy subjects and cultured in the presence of a Pan-Caspase inhibitor, selective inhibitors of Caspase 8, 9 and 3, and IGFBP3. Assay was performed in triplicate. FIG. 3L provides bar graphs grouping % of developed mini-guts of the total obtained from healthy subjects and cultured in different conditions (normal glucose+normal serum, high glucose+normal serum, T1D+ESRD serum+normal glucose, T1D+ESRD serum+high glucose) and showing the effect of IGF-I, IGFBP3 and anti-IGF-IR. The p values are relative to baseline condition (medium alone, medium-±high glucose, medium-±long-standing T1D serum, high glucose+long-standing T1D serum). Additional p values have been calculated to compare the difference in mini-gut growth among the following conditions: medium alone vs. medium-±high glucose, vs. medium+high glucose+long-standing T1D serum. Assay was performed in triplicate. FIG. 3M is a bar graph grouping % of developed mini-guts of the total obtained from healthy subjects, cultured for 8 days, exposed to TMEM219 targeting with siRNA and finally compared to TMEM219-expressing crypts in medium alone and in medium-±high glucose-±long-standing T1D serum. Assay was performed in triplicate. Data are expressed as mean±standard error of the mean (SEM) unless differently reported. *p<0.01; p<0.001; *p<0.0001. Abbreviations: IGF-I, insulin-like growth factor 1; IGFBP3, insulin-like grown factor binding protein 3; IGF-IR, insulin-like grown factor 1 receptor; CoSC, colonic stem cell; T1D, type 1 diabetes; ESRD, end stage renal disease; CTRL, healthy subjects; RT-PCR, real-time polymerase chain reaction; ACTB, beta actin; LFQ, Label-free quantitation; SEM, standard error of the mean; siRNA, small RNA interference; inhib, inhibitor.

FIG. 4A is a bar graph representing normalized mRNA expression of TMEM219, LRP1, TGF-β type I and II, in EphB2$^+$ sorted single cells obtained from crypts of healthy subjects. Experiments were performed in triplicate. FIG. 4E is a schematic attempt to represent the effect of circulating IGF-I and IGFBP3 on the CoSCs. FIG. 4F, 4G, 4I are bar graphs reporting the number of crypts (FIG. 4F), depth of crypts (FIG. 4G) and width of crypts (FIG. 4I) assessed on intestinal lower tract sections harvested at baseline and after 8 weeks from STZ-treated B6 mice developing diabetic enteropathy (B6+STZ), naïve B6 (WT), and naïve B6 treated with IGFBP3 (WT+IGFBP3). WT: wild type, STZ: streptozoticin-treated. N=3 mice per group were evaluated. H1-H3. Representative images of intestinal crypts on H&E sections of WT, B6+STZ mice developing diabetic enteropathy, and naïve B6 treated with IGFBP3 (WT+IGFBP3). Histology magnification, 400×. FIG. 4J is a bar graph representing the number of Aldh$^+$ cells/mm$^2$ in immunostained sections of STZ-treated B6 mice developing diabetic enteropathy, WT, and naïve B6 treated with IGFBP3 (WT+IGFBP3). FIGS. 4M, 4O, 4Q are representative images of MIB1$^+$ and Aldh$^+$ cells, and EphB2$^+$ expression in immunostained rectal mucosa bioptic samples of T1D+ESRD who underwent kidney alone (K+T1D) or simultaneous pancreas-kidney (SPK) transplantation at 8 years of follow-up. Histology 400× in FIG. 4M (panels M1-M2) and FIG. 4O (panels O1-O2), 20× in FIG. 4Q (panels Q1-Q2). Scale bar 80 micron. Data are expressed as mean±standard error of the mean (SEM) unless differently reported. *p<0.01; p<0.001; *p<0.0001. Abbreviations: WT, wild type; STZ, streptozoticin-treated; B6, C57BL/6J mice; IGF-I, insulin-like growth factor 1; IGFBP3, insulin-like growth factor binding protein 3; IGF-IR, insulin-like growth factor 1 receptor; CoSC, colonic stem cell; T1D, type 1 diabetes; ESRD, end stage renal disease; CTRL, healthy subjects; SPK, simultaneous kidney-pancreas transplantation; K+T1D, kidney transplantation alone in type 1 diabetes; H&E, hematoxylin and eosin; MIB1, antibody against Ki67; EphB2, Ephrin B receptor 2; Aldh, Aldehyde dehydrogenase; SEM, standard error of the mean.

FIGS. 5A-5M. Treatment of long-standing T1D with SPK replenishes CoSCs and restores the CoSC signature profile and mini-gut development through restoration of circulating IGF-I and IGFBP3. FIGS. 5A, 5B, 5C are bar graphs depicting results of flow cytometric analysis of EphB2$^{hi+}$, EphB2$^{hi+}$LGR5$^+$, EphB2$^+$h-TERT$^+$ cells obtained from isolated crypts in long-standing T1D (Baseline), T1D+ESRD who underwent kidney pancreas (SPK) or kidney alone (K+T1D) transplantation at 8 years of follow-up. N=10 subjects per group were evaluated. FIGS. 5D, 5E, 5F are bar graphs depicting normalized mRNA expression of intestinal stem cell markers EphB2, LGR5, h-TERT, measured by quantitative RT-PCR on isolated intestinal crypts obtained from long-standing T1D (Baseline), T1D+ESRD who underwent kidney pancreas (SPK) or kidney alone (K+T1D) transplantation at 8 years of follow-up. All samples were run in triplicate and normalized to expression of the housekeeping gene ACTB using the ΔΔCt method. N=10 subjects per group were evaluated. FIG. 5G is a Western blot analysis depicting the expression of EphB2, LGR5, h-TERT in isolated intestinal crypts of the four groups at 8 years of follow-up. N=5 subjects per group were evaluated. FIG. 5H is a bar graph depicting the % of developed mini-guts of the total at 8 days of culture of freshly isolated intestinal crypts obtained from long-standing T1D individuals (Baseline), SPK and K+T1D subjects at 8 years of follow-up. N=10 subjects per group were evaluated. FIG. 5I is a heat map representing the CoSC signature marker transcriptomic profiling examined in freshly isolated intestinal crypts of CTRL, long-standing T1D individuals (T1D+ESRD), SPK and K+T1D subjects at 8 years of follow-up. N=10 subjects per group were evaluated. FIG. 5J is a bar graph representing IGF-I levels measured by ELISA in serum of the four groups of subjects at 8 years at follow-up. N=10 subjects per group were evaluated. FIG. 5K is a bar graph depicting IGFBP3 levels measured by ELISA in serum of the four groups of subjects. N=20 subjects per group were evaluated. FIGS. 5L-5M show the correlation between IGFBP3 serum levels and intestinal symptoms assessed using the GSRS questionnaire (0-7) in n=20 subjects of K+T1D (FIG. 5L) and SPK (FIG. 5M) group. Analysis was conducted using ANOVA (p<0.05) in comparing all groups. Data are expressed as mean±standard error of the mean (SEM) unless differently reported. *p<0.01; p<0.001; *p<0.0001. Abbreviations: CoSC, colonic stem cell; T1D, type 1 diabetes; ESRD, end stage renal disease; CTRL, healthy subjects; SPK, simultaneous kidney-pancreas transplantation; EphB2, Ephrin B receptor 2; LGR5, leucine-rich repeat containing G protein-coupled receptor 5; RT-PCR, real-time polymerase chain reaction; ACTB, beta actin; K+T1D, kidney transplantation alone in type 1 diabetes; IGF-I, insulin-like growth factor 1; IGFBP3, insulin-like growth factor binding protein 3; SEM, standard error of the mean.

FIGS. 6A-6N. Treatment with the newly generated recombinant protein ecto-TMEM219 (ecto-TMEM219) abrogates IGFBP3-mediated mini-gut destruction and preserves CoSCs in preclinical model. FIG. 6A is a bar graph grouping % of developed mini-guts of the total obtained from healthy subjects in different conditions and showing the effect of ecto-TMEM219 at various concentrations (1:2, 1:1 and 2:1 molar ratio as compared to IGFBP3) in IGFBP3-treated mini-guts and in those exposed to high glucose. The p values are relative to baseline conditions. FIG. 6B is a bar graph representing normalized mRNA expression of EphB2 in crypts isolated from healthy subjects cultured in the presence of IGFBP3 and ecto-TMEM219+IGFBP3, performed in triplicate. FIGS. 6C-6D are bar graphs representing normalized mRNA expression of Caspase 8 and 9 in crypts isolated from healthy subjects cultured in the presence of IGFBP3 and ecto-TMEM219+IGFBP3, performed in triplicate. FIGS. 6E, 6F, 6G are bar graphs reporting the number of crypts (FIG. 6E), depth of crypts (FIG. 6F) and width of crypts (FIG. 6G) assessed on intestinal lower tract sections harvested at baseline and after 8 weeks from STZ-treated B6 mice developing diabetic enteropathy (B6+STZ), naïve B6 (WT), and STZ-B6 mice treated with ecto-TMEM219. WT: wild type, STZ: streptozoticin-treated. N=3 mice per group were evaluated. FIG. 6H is a bar graph reporting the weight at baseline and after 8 weeks of STZ-treated B6 mice developing diabetic enteropathy (B6+STZ), naïve B6 (WT), and of STZ-treated B6 mice developing diabetic enteropathy treated with ecto-TMEM219. WT: wild type, STZ: streptozoticin-treated. N=3 mice per group were evaluated. FIG. 6I is a bar graph representing results of flow cytometric analysis of EphB2$^+$ cells isolated from intestinal samples collected from naïve B6 mice, STZ-treated B6 mice and in STZ-B6 mice treated with ecto-TMEM219 at 8 weeks. FIG. 6J provides representative flow histograms of EphB2$^+$ cells isolated from crypts isolated from naïve B6 mice, STZ-treated B6 mice and in STZ-B6 mice treated with ecto-TMEM219 at 8 weeks. N=3 to 5 mice per group were evaluated. FIG. 6K is a bar graph representing normalized mRNA expression of EphB2 in intestinal samples collected from naïve B6 mice, STZ-treated B6 mice and in STZ-B6 mice treated with ecto-TMEM219 at 8 weeks. FIGS. 6L, 6M are bar graphs representing normalized mRNA expression of Caspase 8 (K) and Caspase 9 (L) in intestinal samples collected from naïve B6 mice, STZ-treated B6 mice and in STZ-B6 mice treated with ecto-TMEM219 at 8 weeks. FIG. 6N is a bar graph representing IGFBP3 circulating levels measured in naïve B6 mice (WT) and STZ-treated B6 mice (B6+STZ) and in B6+STZ mice treated with ecto-TMEM219 at 8 weeks. Data are expressed as mean±standard error of the mean (SEM) unless differently reported. *p<0.01; p<0.001; *p<0.0001. Abbreviations: WT, wild type; STZ, streptozoticin-treated; B6, C57BL/6J mice; IGF-I, insulin-like growth factor 1; IGFBP3, insulin-like growth factor binding protein 3; CoSC, colonic stem cell; H&E, hematoxylin and eosin; EphB2, Ephrin B receptor 2; SEM, standard error of the mean, T1D, type 1 diabetes; ESRD, end stage renal disease; CTRL, healthy subjects; RT-PCR, real-time polymerase chain reaction; ACTB, beta actin.

FIG. 7C shows the correlation between serum and urine IGFBP3 levels in all subjects of the cohort evaluated for this study. FIGS. 7D-7E shows the correlation between IGFBP3 serum levels and eGFR calculated with MDRD formula in subjects with T1D+ESRD on dialysis (FIG. 7D) and with T1D with eGFR>15 ml/min/m2 (FIG. 7E). FIG. 7F shows the correlation between serum and urine IGFBP3 levels in all subjects of the cohort evaluated for this study. The gray area indicates the normal range within urinary and serum levels of IGFBP3.

FIGS. 8A-8N. CoSC profile, in vitro generation of mini-guts, expression of IGFBP3 in the liver and of IGF-IR on CoSCs in long-standing T1D and healthy subjects. FIGS. 8A-8B are representative flow dot plots of PI$^-$ cells gating strategy in healthy subjects (CTRL) and long-standing T1D individuals (T1D+ESRD). FIG. 8N shows representative pictures of IGF-IR+ cells on rectal mucosa samples obtained from CTRL and from T1D+ESRD individuals. The black arrow on the panel labeled N1 indicates positive cells at the crypt base. Magnification 200×. Data are expressed as mean±standard error of the mean (SEM) unless differently reported. *p<0.01. Abbreviations: PI, propidium iodide; IGF-I, insulin-like growth factor 1; IGFBP3, insulin-like growth factor binding protein 3; IGF-IR, insulin-like growth factor 1 receptor; CoSC, colonic stem cell; T1D, type 1 diabetes; ESRD, end stage renal disease; CTRL, healthy subjects; EphB2, Ephrin B receptor 2; LGR5, leucine-rich repeat containing G protein-coupled receptor 5; RT-PCR, real-time polymerase chain reaction; ACTB, beta actin; SEM, standard error of the mean.

FIGS. 9A-9H. Caspases expression in IGF-I/IGFBP3 cultured mini-guts and the lack of effect of other circulating factors confirmed IGFBP3 major pro-apoptotic effect on mini-guts development. FIG. 9A is a bar graph representing normalized mRNA expression of Caspase 8 in crypts isolated from individuals with T1D+ESRD cultured in the presence of IGFBP3, IGF-I+IGFBP3 and IGF-I, performed in triplicate. FIG. 9B is a bar graph representing normalized mRNA expression of Caspase 9 in crypts isolated from individuals with T 1 D+ESRD cultured in the presence of IGFBP3, IGF-I+IGFBP3 and IGF-I, performed in triplicate. FIGS. 9C-9D are bar graphs grouping % of mini-guts developed from healthy subjects (FIG. 9C) and from long-standing T1D individuals (FIG. 9D), cultured in the presence of medium with FBS and medium with serum obtained from healthy subjects, "CTRL serum". Assay was run in triplicate. FIG. 9E is a bar graph grouping % of developed mini-guts of the total obtained from healthy subjects, cultured for 8 days, exposed to TMEM219 targeting with siRNA and anti-IGF-IR, and finally compared to TMEM219-expressing crypts in medium alone and in medium+high glucose+long-standing T1D serum. Assay was performed in triplicate. FIGS. 9F-9G are bar graphs grouping % of developed mini-guts at 8 days of culture, obtained from healthy subjects (FIG. 9F) and long-standing T1D individuals (FIG. 9G) cultured in the presence of medium alone and various molecules identified with proteomic analysis (Table S7). Assay was performed in triplicate. FIG. 9H is a bar graph grouping % of mini-guts obtained from healthy subjects and cultured in the presence of medium alone, medium+high glucose, medium+high glucose and long-standing T1D serum, IGF-I, IGFBP3 with/without insulin. Assay was performed in triplicate. Data are expressed as mean±standard error of the mean (SEM) unless differently reported. *p<0.01; **p<0.001. Abbreviations: IGF-I, insulin-like growth factor 1; IGFBP3, insulin-like growth factor binding protein 3; IGF-IR, insulin-like growth factor 1 receptor; CoSC, colonic stem cell; T1D, type 1 diabetes; ESRD, end stage renal disease; CTRL, healthy subjects; RT-PCR, real-time polymerase chain reaction; ACTB, beta actin; SEM, standard error of the mean; siRNA, small RNA interference; ALDOA, Fructose-bisphosphate aldolase A; RNASE, Ribonuclease pancreatic; MASP, Mannan-binding lectin serine protease 1.

FIGS. 10A-10J. Effect of IGF-I/IGFBP3 dyad on single cell derived mini-guts, on stem cell transcriptome profile and on apoptotic pathways. FIG. 10A is comprised of images of single cell-derived mini-guts, cultured for 8 days in vitro obtained from previously isolated EphB2$^+$ sorted cells of healthy subjects and cultured with medium alone, medium+IGFBP3, medium+Glucose 35 mM+long-standing T1D serum. Images are shown at 10× magnification. Scale bar 50 micron. FIGS. 10B, 10C, 10D are bar graphs representing normalized mRNA expression of Caspase 8, Caspase 9, and Ki67 in single cell-derived mini-guts grown from flow sorted EphB2$^+$ cells isolated from healthy subjects and cultured in different conditions. Assay was performed in triplicate. FIGS. 10E-10F are scatter plots representing the stem cell transcriptome profiling examined in freshly isolated intestinal crypts of healthy subjects (CTRL) and long-standing T1D individuals (T1D+ESRD) cultured with/without IGFBP3 and IGF-I. Assays were run in triplicate. FIGS. 10G-10H are scatter plots representing the apoptosis transcriptome profiling examined in freshly isolated intestinal crypts of health subjects (CTRL) and long-standing T1D individuals (T1D+ESRD) cultured with/without IGF-I. A table summarizes genes and pathways analyzed (Table S3). Assays were run in triplicate. FIGS. 10I-10J are bar graphs grouping % of mini-guts developed from crypts obtained from healthy subjects (FIGS. 10I) and long-standing T1D (FIGS. 10J) and then cultured in the presence of medium alone, Fas Ligand (FasL), hydrogen peroxide ($H_2O_2$) and Tumor Necorsis Factor alpha (TNF-α). Assay was performed in triplicate. Data are expressed as mean±standard error of the mean (SEM) unless differently reported. *p<0.01; p<0.001; *p<0.0001. Abbreviations: IGF-I, insulin-like growth factor 1; IGFBP3, insulin-like growth factor binding protein 3; CoSC, colonic stem cell; T1D, type 1 diabetes; ESRD, end stage renal disease; CTRL, healthy subjects; RT-PCR, real-time polymerase chain reaction; ACTB, beta actin; SEM, standard error of the mean; FasL, Fas Ligand; $H_2O_2$ peroxide; TNF-α, Tumor Necrosis Factor alpha.

FIG. 11A is a bar graph representing IGFPB3 circulating levels measured in naïve B6 mice (WT) and STZ-treated B6 mice (B6±STZ). FIGS. 11M-11N are bar graphs representing normalized mRNA expression of Caspase 8 (FIG. 11M) and Caspase 9 (FIG. 11N) in intestinal samples collected from naïve B6 mice, STZ-treated B6 mice and in STZ-B6 mice treated with IGFBP3 (B6+STZ+IGFBP3). Data are expressed as mean±standard error of the mean (SEM) unless differently reported. *p<0.01; p<0.001; *p<0.0001. Abbreviations: WT, wild type; STZ, streptozoticin-treated; B6, C57BL/6J mice; IGF-I, insulin-like growth factor 1; IGFBP3, insulin-like growth factor binding protein 3; CoSC, colonic stem cell; H&E, hematoxylin and eosin; EphB2, Ephrin B receptor 2; Aldh, Aldehyde dehydrogenase; SEM, standard error of the mean.

FIGS. 12A-12C are bar graphs depicting the score of abdominal pain, diarrhea and constipation according to the GSRS questionnaire in healthy subjects (CTRL), long-standing T1D individuals (Baseline), T1D+ESRD who underwent kidney pancreas (SPK) or kidney alone (K+T1D) transplantation. The gray area indicates normal range for all the parameters. Statistics are expressed as mean±SEM. FIGS. 12D, 12E, 12G, 12J are representative pictures of hematoxylin and eosin (H&E) staining and ultrastructural analysis of neural structures (red arrows indicate localization and presence of neuroendocrine vesicles), Schwann cells (red arrows indicate cytoplasm derangements), and 5HT$^+$ cells performed on rectal mucosa biopsy samples obtained from T1D+ESRD who underwent kidney pancreas (SPK) or kidney alone (K+T1D) transplantation at 8 years of follow-up. Magnification 400×. FIGS. 12F, 12H, 12I, 12K are bar graphs reporting the measurements of neuroendocrine vesicles (% of cases with >3 NE vesicles detected per nerve terminal), % of Schwann cells with picnotic nuclei and cytoplasm derangements (% of positive cases) using electron microscopy, 5HT$^+$ cells, performed on bioptic samples obtained from rectal mucosa of CTRL, long-standing T1D individuals (Baseline), T1D+ESRD who underwent kidney pancreas (SPK) or kidney alone (K+T1D) over an 8-year follow-up period. Statistics are expressed as mean±SEM. N=20 CTRL, n=30 SPK, n=30 K+TID and n=60 T1D+ESRD subjects were evaluated. Statistics are expressed as mean±SEM. All parameters examined were statistically significantly different when comparing different groups as following: *p<0.01; p<0.001; *p<0.0001. N=10 subjects per group were evaluated. Abbreviations: GSRS, Gastrointestinal Symptom Rating Scale; SPK, simultaneous kidney-pancreas transplantation; K+T1D, kidney transplantation alone in type 1 diabetes; CTRL, healthy subjects; T1D, type 1 diabetes; ESRD, end stage renal disease; 5HT, serotonin; H&E, hematoxylin and eosin; NGF, neural growth factor; SEM, standard error of the mean; NE, neuroendocrine vesicles.

FIG. 13A provides images of mini-guts, cultured for 8 days in vitro obtained from previously isolated crypts of long-standing T1D individuals, T1D+ESRD who underwent kidney pancreas (SPK) or kidney alone (K+T1D) transplantation at 8 years of follow-up. Images are shown at 5× and 10X magnification. Scale bar 10 micron. FIG. 13B is a scatter plot representing the stem cell transcriptome profiling examined in freshly isolated intestinal crypts of SPK individuals. N=3 subjects were evaluated. FIG. 13C is a bar graph depicting relative expression levels of IGF-I receptor (IGF-IR) on isolated crypts of healthy subjects (CTRL), long-standing T1D individuals (TID+ESRD), SPK and K+T1D measured by quantitative RT-PCR. All samples were run in triplicate and normalized to the ACTB relative expression level using the ΔΔCt method. Results are expressed as mean±SEM. FIG. 13D is a heat map representing the proteomic profile of long-standing T1D as compared to CTRL and SPK subjects at 8 years of follow-up. The complete dataset of identified and quantified proteins was subjected to statistical analysis (p<0.05). Significantly differentially expressed proteins were further analyzed through hierarchical clustering. Statistics are expressed as mean±SEM. Sera of n=10 subjects per group were evaluated. All parameters examined were statistically significantly different when comparing different groups as following: *p<0.01. Abbreviations: T1D, type 1 diabetes; ESRD, end stage renal disease; CTRL, healthy subjects; SPK, simultaneous kidney-pancreas transplantation; K+T1D, kidney transplantation alone in type 1 diabetes; RT-PCR, real-time polymerase chain reaction; ACTB, beta actin; IGF-I, insulin-like growth factor 1; IGFBP3, insulin-like growth factor binding protein 3; IGF-IR, insulin-like growth factor 1 receptor; SEM, standard error of mean.

FIGS. 14A-14B are bar graphs showing the correlation between insulin serum levels and intestinal 10 symptoms assessed using the GSRS questionnaire and considering the item with the highest score (0-7) in n=20 subjects of K+T1D (FIG. 14A) and SPK (FIG. 14B) group. Analysis was conducted using ANOVA (p<0.05) in comparing all groups. FIG. 14C is a bar graph showing insulin serum levels measured using the Free-insulin method in n=20 subjects of K+T1D (FIG. 14A) and SPK (FIG. 14B) group. Data are expressed as mean±standard error of the mean (SEM). FIGS. 14D, 14E are bar graphs showing the correlation between glycated hemoglobin (HbA1C) serum levels and intestinal symptoms assessed using the GSRS questionnaire (0-7) in n=20 subjects of K+T1D (FIG. 14A) and SPK (FIG. 14B) group. Analysis was conducted using ANOVA (p<0.05) in comparing all groups. FIGS. 14F, 14G are line graphs showing the correlation between blood glucose levels (Glycemia) and intestinal symptoms assessed using the GSRS questionnaire (0-7) in n=20 subjects of K+T1D (FIG. 14A) and SPK (FIG. 14B) group. Analysis was conducted using ANOVA (p<0.05) in comparing all groups. Abbreviations: T1D, type 1 diabetes; ESRD, end stage renal disease; CTRL, healthy subjects; SPK, simultaneous kidney-pancreas transplantation; K+T1D, kidney transplantation alone in type 1 diabetes; IGF-I, insulin-like growth factor 1; IGFBP3, insulin-like growth factor binding protein 3.

FIGS. 15A, 15B, 15C, 15D, 15E are representative images (10× magnification) of citokeratin 20 (KRT20), vimentin, Synaptofisin and Aldehyde Dehydrogenase (ALDH) expression in mini-guts obtained from crypts isolated from healthy subjects, CTRL (FIG. 15A, panels labeled A1-A4), and T1D+ESRD individuals (FIG. 15B, panels labeled B1-B4), cultured with IGFBP3 (FIG. 15C, panels labeled C1-C4), Glucose 35 mM (FIG. 15D, panels labeled D1-D4), and Glucose 35 mM)+long-standing T1D serum (T1D+ESRD serum)+IGF-I (FIG. 15E, panels labeled E1-E4). Immunofluorescence confirmed that expression of all lineages markers is reduced in mini-guts obtained from T1D+ESRD individuals as compared to CTRL (FIG. 15A, panels labeled A1-A4, FIG. 15B, panels labeled B1-B4), with ALDH being the least expressed marker (FIG. 15B, panel labeled B4). Decreased ALDH expression was also detected in IGFBP3-treated mini-guts (FIG. 15C, panel labeled C4), while mini-guts exposed to high glucose and long-standing T1D serum and treated with IGF-I showed evident ALDH expression recovery. FIG. 15F is a bar graph representing expression of TMEM219, KRT20, Epithelial-cell adhesion molecule (Ep-Cam) and Chromogranin A (CHGA) on non-stem cells (EphB2$^+$ cells) measured by quantitative RT-PCR. All samples were run in triplicate and normalized to the ACTB relative expression level using the ΔΔCt method. Results are expressed as mean±SEM. Abbreviations: T1D, type 1 diabetes; ESRD, end stage renal disease; CTRL, healthy subjects; IGF-I, insulin-like growth factor 1; IGFBP3, insulin-like growth factor binding protein 3; IF, immunofluorescence; KRT20, citokeratin 20, ALDH, Aldehyde Dehydrogenase, EpCam, epithelial cell adhesion molecule; CHGA, Chromogranin A; RT-PCR, real-time polymerase chain reaction; ACTB, beta actin.

FIGS. 17A-17G; 17M-17P are bar graphs grouping % of developed mini-guts with at least 1 crypt domain detectable in different conditions already reported throughout the paper.

DETAILED DESCRIPTION OF THE INVENTION

Example 1

Figure 1A:
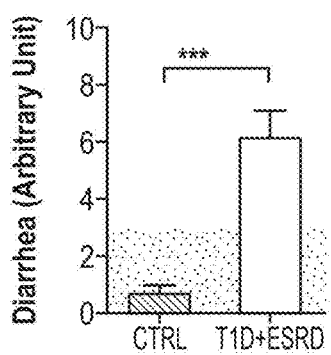

Material and Methods 60 individuals with long-standing T1D (T1D+ESRD) registered on the waiting list for simultaneous pancreas-kidney transplantation (SPK) were enrolled in the study and compared with 20 healthy subjects matched for age and gender (CTRL). Assessment of gastrointestinal symptoms, intestinal motility and intestinal mucosa pathology defined DE. CoSCs were identified on colonic purified crypts based on the expression of CoSC specific markers (flow-cytometry, RT-PCR, Western Blot, transcriptome profiling). CoSCs self-renewal properties were assessed by evaluating the % of in vitro developed mini-guts and by characterizing their expression of cell lineages markers in different conditions (FIGS. 15A-15F). Broad serum proteomic was used to detect circulating factors that may regulate CoSCs and candidate factors were then tested in the in vitro mini-gut assay (FIG. 16). Detailed methods and statistical analysis are described below. The Study was approved by the Institutional Review Board of Istituto di Ricovero e Cura a Carattere Scientifico Ospedale San Raffaele, Milano, Italy (Enteropathy-Pancreas KidneyTransplantation/01 Secchi/Fiorina).

Patients and Study Design 60 individuals with T1D+ESRD registered on the waiting list for simultaneous pancreas-kidney transplantation (SPK) matched for (age 41 to 43 years old), gender, and duration of T1D (29.4±1.8 years) were enrolled in the study. 20 healthy subjects matched for age and gender (CTRL), with normal renal function and normal glycometabolic parameters, were studied as well. T1D+ESRD subjects were all on intensive insulin treatment at the time of enrollment in the study, while the CTRL group was not being administered any medication. All T1D+ESRD subjects were on the same treatment as antiplatelet therapy (ASA) and anti-hypertension (angiotensin-converting-enzyme inhibitors), while 40 out of 60 received statins when enrolled in the study. Subjects with clear signs of inflammatory bowel diseases as well as celiac disease were not enrolled.

T1D+ESRD individuals were followed up for 8 years (mean follow-up: 8.6±1.1 years) after receiving either SPK (n=30) or K+T1D (n=30) transplantation according to the macroscopic surgical evaluation at the time of transplantation. Individuals taking an oral anticoagulant agent were not included. SPK individuals were all insulin-independent for the entire follow-up period, whereas K+T1D individuals were on intensive subcutaneous insulin therapy. All subjects provided informed consent before study enrollment. Studies not included in the routine clinical follow-up were covered by an appropriate Institutional Review Board approval (Enteropatia-trapianto/01 Secchi/Fiorina).

Transplantation and Immunosuppression

Organs for transplantation were obtained from deceased donors through the "North Italia Transplant" organ procurement consortium (NITp, Milan). After induction with ATG (thymoglobulin, IMTIX, SANGSTAT), immunosuppression was maintained using cyclosporine (through levels between 100-250 ng/ml) or FK506 (through levels between 10-15 ng/ml), mycophenolate mofetil (500-2000 mg/day), and methylprednisolone (10 mg/day). Steroids were withdrawn within 3-6 months after transplantation. All patients included in the T1D+ESRD and SPK groups were on anti-platelet therapy (80% ASA and 20% ticlopidine) to prevent graft or fistula thrombosis. Metabolic status, renal function and blood pressure were examined during enrolment and after transplantation every 2 years thereafter. The estimate glomerular filtration rate (eGFR) was calculated using the Modification of Diet in Renal Disease (MDRD) formula (Levey et al., 1999).

The Gastrointestinal Symptom Rating Scale (GSRS)

Gastrointestinal symptoms were evaluated by GSRS questionnaire in healthy subjects, in longstanding T1D individuals (T1D+ESRD) and in SPK and K+T1D groups at 2, 4 and 8 years after transplantation. The Gastrointestinal Symptom Rating Scale (GSRS) is a questionnaire consisting of 15 items with a seven-graded Likert scale defined by descriptive anchors (Svedlund et al., 1988). The questionnaire was originally constructed as an interview-based rating scale designed to evaluate a wide range of gastrointestinal symptoms and was later modified to become a self-administered questionnaire. The higher the scores, the more severe the symptoms: the scale ranges from a minimum value of 1 to a maximum value of 7. If an individual's participation in the study is discontinued, the value at the last available observation will be carried forward in the analysis. The items can be grouped into five dimensions previously identified on the basis of a factor analysis: abdominal pain syndrome (three items), reflux syndrome (two items), indigestion syndrome (four items), diarrhea syndrome (three items) and constipation syndrome (three items).

Anorectal Manometry

Data on anorectal manometry were already available in healthy subjects, and were compared with those obtained by performing anorectal manometry in long-standing T1D individuals (T1D+ESRD) using a custom-designed, open-tip, 14-Fr diameter, PVC probe with seven lumens 15 and a 4-cm latex balloon tied at the end of the probe (Bioengineering Laboratories Plc., Milan, Italy) (Carrington et al., 2014; Remes-Troche et al., 2010). The sphincter length was measured after a 10-minute run-in period, anal pressure was recorded for 15 minutes in resting conditions. Subjects were then instructed to squeeze the anus as tightly as possible and for as long as possible-for at least 20 seconds. Inventors' study evaluated the following items: Resting Tone, Contraction Tone, Reflex Response, and Urgency Response.

Pathology, Immunohistochemistry and Electron Microscopy

Colorectal endoscopy procedure was performed in healthy subjects, in long-standing T1D individuals (T1D+ESRD) at baseline and in SPK and K+T1D groups at 2, 4, and 8 years after transplantation using a Welch Allyn optic sigmoid scope. Intestinal mucosal samples were fixed in buffered formalin (formaldehyde 4% w/v and acetate buffer 0.05 M) and routinely processed in paraffin wax. 3 μm-thick sections of each enrolled case were stained with Hematoxylin & Eosin (H&E) for morphological evaluations. For immunohistochemistry, 3 μm-thick sections were mounted on poly-L-lysine coated slides, deparaffinized and hydrated through graded alcohols to water. After antigen retrieval, performed by dipping sections in 0.01 M citrate buffer, pH 6 for 10 minutes in a microwave oven at 650 W as well as endogenous peroxidase activity inhibition, performed by dipping sections in 3% hydrogen peroxide for 10 minutes, incubation with primary antibodies was performed at 4° C. for 18-20 hours, followed by the avidin-biotin complex procedure (Hsu et al., 1981). Immunoreactions were developed usmg 0.03% 3,3' diaminobenzidine tetrahydrochloride, and then sections were counterstained with Harris' hematoxylin. The following antibodies were used: Ki67 (monoclonal, clone MIB M1B1, 1:100 dilution, Dako, Carpinteria, Calif., USA), aldehyde dehydrogenase (monoclonal, clone 44/ALDH, 1:1000 dilution, Transduction Laboratories, Franklin Lakes, N.J., USA), EphB2 (monoclonal, clone 48CT12.6.4, 1:200 dilution, Lifespan Biosciences, Seattle, Wash., USA), LGR5 (monoclonal, clone 2A2, 1:100 dilution, Origene Technologies, Rockville, Md., USA), hTERT (monoclonal, clone Y182, 1:500 dilution, Millipore, Billerica, Mass., USA), glicentin (polyclonal, 1:1250 dilution, Milab, Malmo, Sweden), pancreatic polypeptide (polyclonal, 1:500 dilution, Peninsula, Belmont, Calif., USA), PYY (polyclonal, 1:1000 dilution, Biogenesis, Bournemouth, UK), serotonin (monoclonal, clone YC5, 1:50 dilution, Biogenesis), somatostatin (polyclonal, 1:550 dilution, Dako), IGF-I (polyclonal, 1:500, Abcam) and IGF-IR (polyclonal, 1:100, Cell Signaling Technologies), (Fiorina et al., 2003). For ultrastructural studies, samples were fixed for 2 hours at 4° C. in a mixture of 2% paraformaldehyde and 2% glutaraldehyde in 0.05 M cacodylate buffer, pH 7.3. They were post-fixed in 1% osmium 15 tetroxide for 1 hour at room temperature, then dehydrated and embedded in Epon-Araldite. Ultrathin sections were cut with a diamond knife and mounted on 200-mesh nickel grids, previously coated with a Formvar film. Ultrathin sections were stained with aqueous uranyl acetate and Reynold's lead citrate solutions and subsequently examined with a Philips Morgagni 268D electron microscope. Cases were grouped according to the number of neuroendocrine vesicles (n>3 and n<3) for statistical analysis. For crypt isolation, tissue was collected in a sample containing a mixture of antibiotics and processed as described in the next paragraph. The immunostaining intensity for EphB2 was graded as 1 (negative EphB2 gradient to few cells positive per crypt per field) to 5 (strong EphB2 gradient in all longitudinal crypts). An anti-IGFBP3 primary antibody (polyclonal, 1:50 dilution, Sigma Aldrich) was immunohistochemically tested in liver biopsies 25 from patients with type 1 diabetes. Liver biopsies without pathological findings were used as controls. All of these tissue samples came from the files stored at the Unit of Pathology of the Department of Biomedical, Biotechnological, and Translational Sciences, University of Parma, Parma, Italy. The immunostaining intensity was graded as 1 (mild), 2 (moderate), and 3 (strong), while its diffusion as 1 (focal), 2 (zonal), and 3 (diffuse).

Immunoflurescence

Immunofluorescence samples obtained from liver biopsies were observed using a confocal system (LSM 510 Meta scan head integrated with the Axiovert 200 M inverted microscope; Carl Zeiss, Jean, Germany) with 63× oil objective. Images were acquired in multitrack mode, using consecutive and independent optical pathways. The following primary antibodies were used: rabbit IGFBP3 (1:10, Sigma) mouse Hep Par-1 (1:20, monoclonal, Dako), mouse CD163 (1:10, cloneMRQ26, CellMarque).

Figures 15A, 15B, 15C, 15D, 15E:
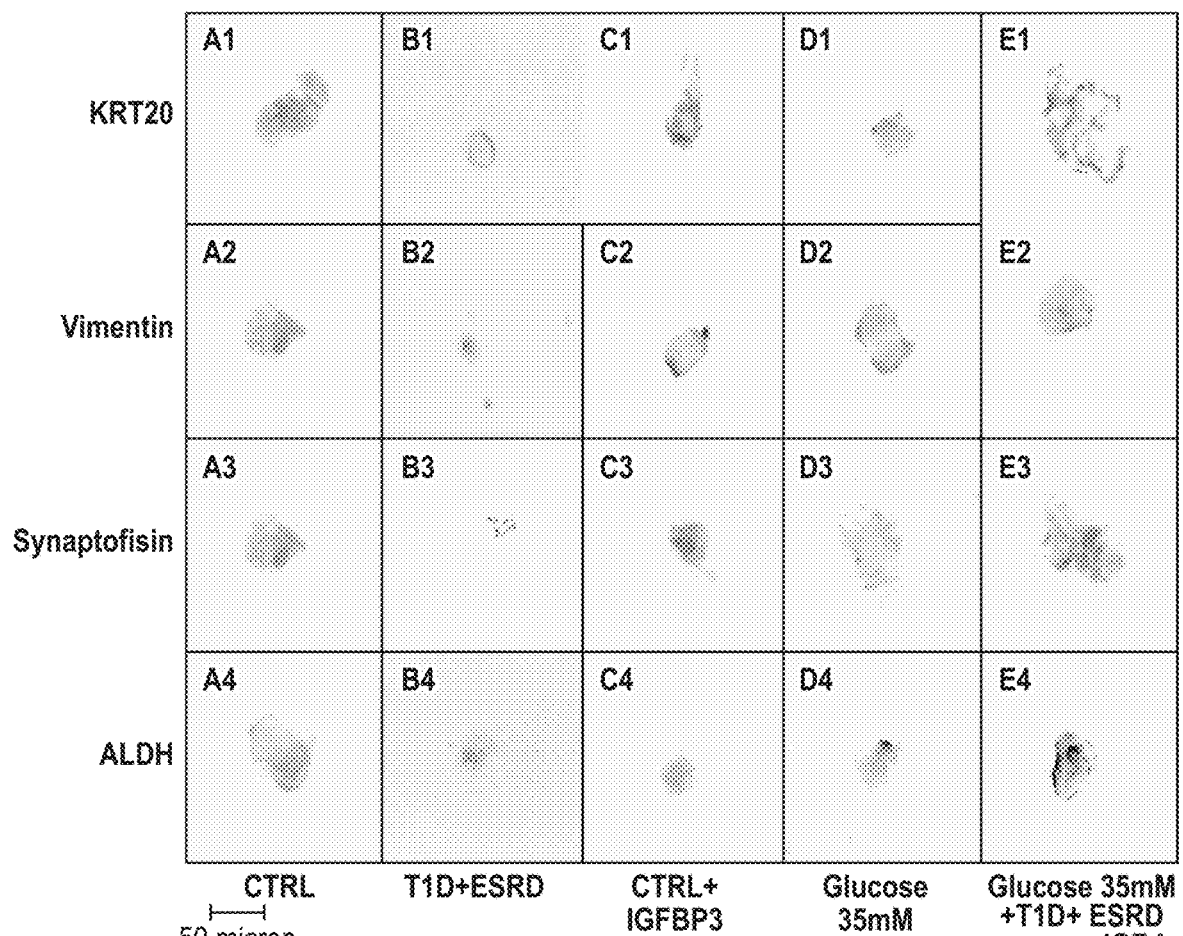
FIGS. 15A-15F. Expression of cell lineages markers in mini-guts exposed to different culturing conditions.
Figure 15F:
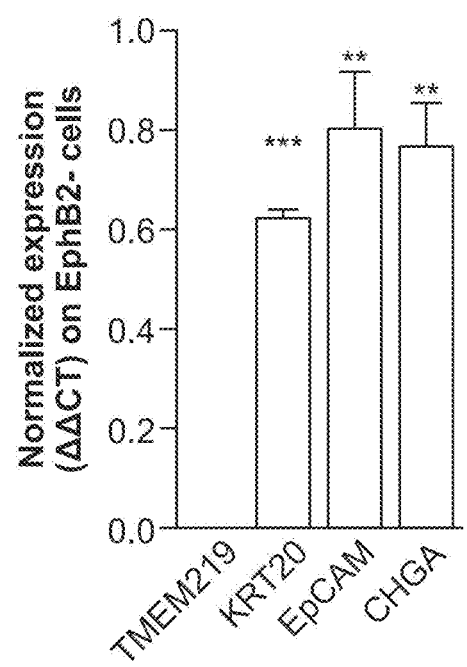
Figure 16:
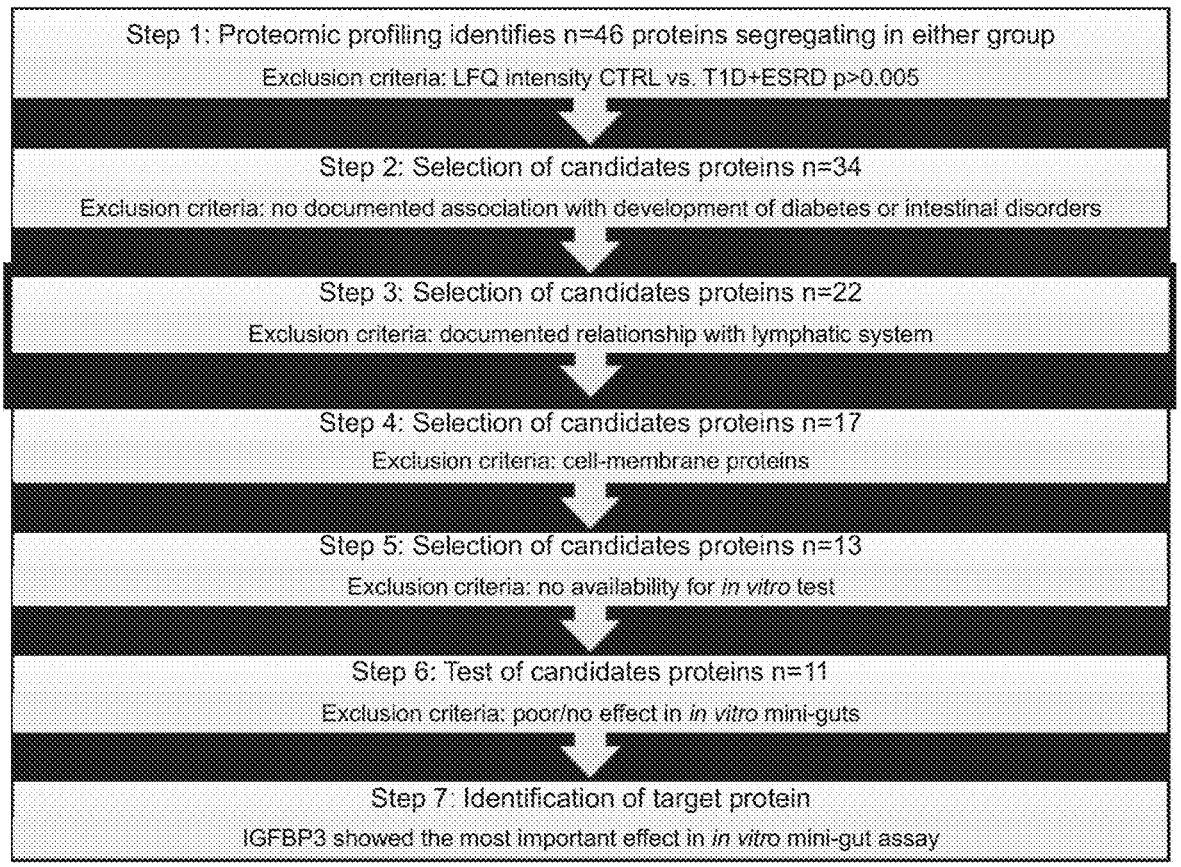
FIG. 16. Selection strategy to test candidate proteins in in vitro mini-guts assay. Flow chart depicting the strategy used to select protein candidates based on proteomic profile to be tested in in vitro mini-guts assay.
Figure 17N:
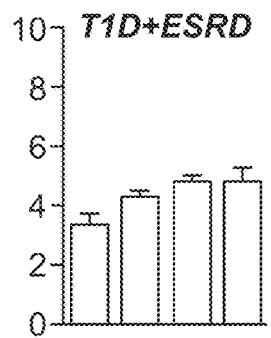
FIGS. 17A-17G; 17M-17P. Analysis of developed mini-guts using the crypt domain quantitative criteria.
Figure 17O:
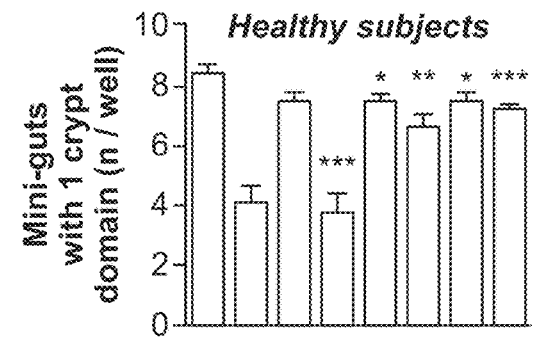
Figure 17P:
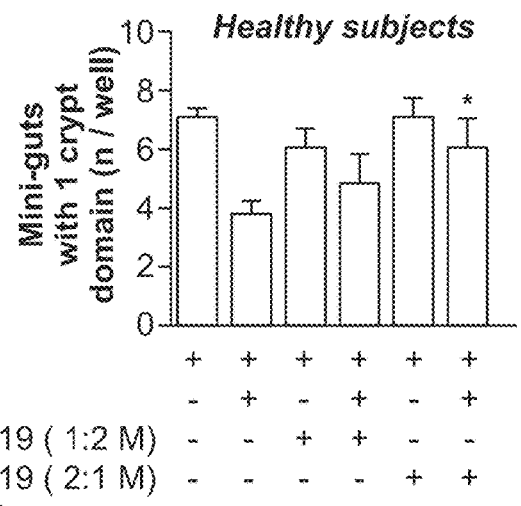

Mini-guts co-cultured with/without IGFBP3, with/without long-standing T1D serum+high glucose (35 mM Glucose) and those obtained from crypts of T1D+ESRD individuals, were stained with Vimentin, Citocheratin 20, Aldheide Dehydrogenase and Synaoptifisin for immunofluorescence analysis to assess expression of cell lineages markers (FIG. 15A, panels labeled A1-A4; FIG. 15B, panels labeled B1-B4; FIG. 15C, panels labeled C1-C4; FIG. 15D, panels labeled D1-D4; FIG. 15E, panels labeled E1-E4). The following primary antibodies were used: mouse vimentin (1:80, monoclonal, clone: V9 Dako) mouse Aldheyde (1:1000, monoclonal, clone: 44, BD), mouse citocherain 20 (1:100, monoclonal, clone:Ks20.8, Dako) and Synaptofisin (1:100, monoclonal, clone: syn88, BioGenex).

In Situ Hybridization

Paraffin sections of human colon mucosa were de-paraffinized and re-hydrated according to standard procedures. After treatment of sections using 0.2M HCl for 15 minutes at room temperature, sections were washed 3 times in PBS and incubated for 15 min at 37° C. in proteinase K (30 μg/ml in PBS). 0.2% glycine in PBS was added for 1 minute in order to neutralize Proteinase K activity, and samples were washed twice in PBS. After post-fixation in 4% PFA for 10 min at room temperature and 3 washes in PBS, histone acetylation was achieved by incubating samples two times for 5 min in an aqueous solution containing 1.5% triethanolamine, 0.15% HCl, and 0.6% acetic anhydride. Samples were then washed and pre-hybridized for 1 hour at 68° C. in hybridization solution (50% formamide, 5×SSC, pH4.5, 2% Blocking Reagent (Roche), 0.05% CHAPS (Sigma), 5 mM EDTA, 50 μg/ml Heparin (Sigma) and 50 μg/ml yeast RNA. For TMEM219, the digoxigenin-labelled probe was diluted 750 ng/ml in hybridization solution and incubated for 24 hrs at 65° C. Post-hybridization washes were performed 3×20 min in 50% Formamide/2×SSC at 65° C. Sections were rinsed in TBS-T buffer (0.1M TrisHCl pH7.5, 0.15M NaCl, 0.1% Tween20) and blocked for 30 min at room temperature in Blocking Solution (0.5% Blocking Reagent, 10% sheep serum in TBS-T). Sheep anti-DIG antibody (Fab fragment, Roche) was diluted 1/2000 in Blocking Solution and incubated overnight at 4° C. After this, samples were washed in TBS-T and then in NTM buffer (0.1M Tris pH9.5, 0.1M NaCl, 0.05M MgCl2) and developed in NBT/BCIP solution (Roche) for 24 hrs.

CoSC Characterization
Crypt Purification

Muscle layer and sub-mucosa were carefully removed from human fresh rectal biopsy specimens, and mucosa was incubated with a mixture of antibiotics (Normocin, [Invivogen, San Diego, Calif. 92121, USA], Gentamycin [Invitrogen, Carlsbad, Calif., USA] and Fungizone [Invitrogen]) for 15 minutes at room temperature (RT). Next, tissue was cut into small pieces and incubated with 10 mM Dithiotreitol (DTT) (Sigma, St. Louis, Mo. 63103, USA) in PBS 2-3 times for 5 minutes at RT. Samples were then transferred to 8 mM EDTA in PBS and slowly rotated for 60-75 minutes at 4° C. Supernatant was replaced by fresh PBS, and vigorous shaking of the sample yielded supernatants enriched in colonic crypts. Fetal bovine serum (FBS, Sigma) was added to a final concentration of 5%, and fractions were centrifuged at 40×g for 2 minutes in order to remove single cells. This washing procedure was repeated 3 times with Advanced DMEM/F12 (ADF, Gibco) medium supplemented with 2 mM GlutaMax (Invitrogen), 10 mM HEPES (Sigma), and 5% FBS (Sigma).

200-300 isolated human colonic crypt units were mixed with 50 μl matrigel and plated on pre-warmed 24-well culture dishes as already described. After solidification (15-20 minutes at 37° C.), crypts were overlaid with 600 μl complete crypt culture medium [Wnt3a-conditioned medium and Advanced DMEM/F12 (Life Technologies, Grand Island, N.Y.) 50:50, supplemented with Glutamax, 10 mM HEPES, N-2 [1×], B-27 without retinoic acid [1×], 10 mM Nicotinamide, 1 mM N-Acetyl-L-cysteine, 50 ng/ml human EGF (Life Technologies, Grand Island, N.Y.), 1 μg/ml RSPO1 (Sino Biological, Beijing, China), 100 ng/ml human Noggin (Peprotech, Rocky Hill, N.J., USA), 1 μg/ml Gastrin (Sigma-Aldrich, St. Louis, Mo.), 500 nM LY2157299 (Axon MedChem, Groningen, The Netherlands), 10 μM SB202190 (Sigma) and 0.01 M PGE2 (Sigma)]. Medium was replaced every other day. Rock inhibitor Y-27632 (10 μM, Sigma) was added to the cultures for the first 2-3 days. Purified crypts were directly cultured for 8 days. Cell Lineages markers for enterocytes and enteroendocrine cells were assessed in the mini-guts and in the EphB2$^+$ and EphB2$^-$ sorted single cells with RT-PCR by testing: CHGA, KRT20 and EPCAM (Life Technologies, Grand Island, N.Y.). Colony forming efficiency (%) was evaluated on freshly isolated crypts in order to exclude that the bioptic procedure and the isolation processing could have compromised their efficiency in forming mini-guts in in vitro culture. DAPI staining was performed to confirm number of nuclei in freshly isolated crypts from CTRL and T1D+ESRD subjects. Developed mini-guts with at least 1 crypt domain were also counted and percentage was calculated in order to add a more quantitative criteria to measure developed mini-guts (FIGS. 17A-17G; 17M-17P). Insulin and glucose levels measured on long-standing T1D (T1D+ESRD) and CTRL serum are reported below:

Glucose levels (T1D+ESRD vs. CTRL, 178±47.5 vs 90±5.5 mg/dl, p0.0001);

Insulin levels (T1D+ESRD vs. CTRL, 12.9±4.6 vs 5.8±1.6 μIU/ml, p=0.009).

Flow Cytometry

The expression of the CoSC markers EphB2 (APC anti-human EphB2 antibody, R&D, Minneapolis, Minn.) and LGR5 (PE anti-human LGR5, Origene, Rockville, Md.) was determined by flow cytometry by excluding CD45- and -positive cells (V450 anti-human CD45 and CD1 b, BD Biosciences, San Jose, Calif.). Propidium iodide (PI) was added (10 jag/ml) to exclude dead cells. EphB2+ cells were also sorted by flow cytometry to obtain a single cell suspension for culturing purposes. Intracellular detection of human-tert (hTERT) was performed by permeabilizing cells and staining with primary anti-human hTERT antibody (GeneTex, Irvine, Calif.) followed by DAPI anti-goat secondary antibody (Life Technologies). With regard to the analysis, cells were all first gated as PI$^-$ before the assessment of other surface or intracellular markers. Samples were run on a BD LSR-Fortessa and analyzed by FSC Express 3.0 (DeNovo Software, Los Angeles, Calif., USA).

In Vitro Mini-Gut Generation Study

Crypts were isolated from healthy subject rectal biopsy samples and cultured as previously described to generate mini-guts. To create hyperglycemic conditions, the culturing medium was modified by adding glucose at different concentrations (35 mM: high glucose; 5 mM: normal glucose). To mimic uremic conditions, human uremic serum obtained from long-standing T1D individuals with ESRD was added to crypts, which were cultured as reported in the crypt culturing methods section. After 8 days, crypts were collected, and the morphology, mini-gut growth, expression of intestinal signature markers (EphB2, LGR5, h-TERT), IGF-IR and TMEM219 (Life Technologies), and Caspase 9 (Life Technologies) were examined using RT-PCR. A pan-caspase inhibitor (caspase inhibitor Z-VAD-FMK, 20 mM, Promega, Madison, Wis.), a Caspase 8 selective inhibitor (Z-IETD-FMK, BD Pharmingen), a Caspase 9 selective inhibitor (Z-LEHD-FMK, BD Pharmingen), a caspase3 inhibitor Z-DEVD-FMK (BD Pharmingen) were used in vitro in mini-guts to confirm the antiapoptotic effect of IGFBP3.

To culture isolated crypts with crypts culturing medium containing healthy subjects human serum, namely CTRL serum, in place of regular FBS, L-Wnt3 cells were grown in 10% CTRL serum to generate conditioned medium that was further added 50:50 to Advanced DMEM/F 12 medium in order to obtain the crypts culture medium as previously described (see Crypt purification).

To assess the properties of sorted EphB2$^+$ cells in generating mini-guts, 2000 sorted cells were mixed with 50 μl matrigel and plated on pre-warmed 24-well culture dishes. After solidification of the matrigel (10-15 min at 37° C.), cells were overlaid with "single cell growth medium" (=complete crypt culture medium+10 M Rock inhibitor Y-27623). Medium was replaced with fresh single cell growth medium every other day. Rock inhibitor was included in the culture medium for seven to nine days.

Immunoblotting

Total proteins of intestinal bioptic samples were extracted in Laemmli buffer (Tris-HCl 62.5 mmol/1, pH 6.8, 20% glycerol, 2% SDS, 5% f3-mercaptoethanol) and their concentration was measured (Lowry et al., 1951). 35 μg of total protein was electrophoresed on 7% SDS-PAGE gels and blotted onto nitrocellulose (Schleicher & Schuell, Dassel, Germany). Blots were then stained with Ponceau S. Membranes were blocked for 1 h in TBS (Tris [10 mmol/1], NaCl [150 mmol/1]), 0.1% Tween-20, 5% non-fat dry milk, pH 7.4 at 25° C., incubated for 12 h with 200 mg/ml of a polyclonal anti-goat EphB2 antibody or polyclonal anti-goat LGR5 antibody (Santa Cruz Biotechnology, Santa Cruz, Calif., USA) or monoclonal IGF-IR (Santa Cruz Biotechnology) and polyclonal TMEM219 (R&D, Minneapolis, Minn.) diluted 1:200 or with a monoclonal mouse anti-β-actin antibody (Santa Cruz Biotechnology) diluted 1:1000 in TBS-5% milk at 4° C., washed four times with TBS-0.1% Tween-20, then incubated with a peroxidase-labeled rabbit anti-goat IgG secondary antibody (or rabbit anti mouse for β-actin) diluted 1:1000 (Santa Cruz Biotechnology) in TBS- 5% milk, and finally washed with TBS-0.1% Tween-20. The resulting bands were visualized using enhanced chemiluminescence (SuperSignal; Pierce, Rockford, Ill., USA).

Live Imaging of Intestinal Crypt Growth

Live imaging of mini-guts, obtained by purification and culture of intestinal crypts of CTRL, T1D+ESRD and SPK individuals, was performed on a Zeiss Axiovert S 100 equipped with environmental control (from Oko-Lab, Italy) with a chamber in which a humidified premixed gas consisting of 5% CO2 and 95% air was infused, and the whole setup was set at 37° C. Images were acquired at 20-minute intervals for 72 hours. Images were acquired and processed using Time Lapse (Oko-Lab, Italy) and, if necessary, image editing was performed using Adobe Photoshop Elements 7.0.

Morphology Imaging Analysis

The images of mini-guts were taken at day 0, 5 and 8 days by inverted microscopy Leica DH/RB and acquired with Axio Vision AC Release 4.3. Pictures reported in figures represent mini-guts at day 5, 10× magnification.

Transcriptome Profiling

Total RNA was isolated from purified intestinal crypt suspension using the RNeasy Mini Kit (Qiagen, Valencia, Calif.) with on-column DNase I digestion. Next, 3 μg total RNA from each sample was reverse-transcribed using the RT2 First Strand kit (C-03; SABiosciences, Frederick, Md.). The inventors used the Human Stem Cell RT2 Profiler PCR Arrays (PAHS-405Z), the human Stem Cell Signaling PCR Array (PAHS-047Z) and a custom array with the following genes: AXIN2, OLFM4, BMI1, RNF43, CDCA7, SLC12A2, CDK6, SOX9, DKC1, ZNRF3, ETS2, EPHB2, FAM84A, LGR5, GPX2, ACTB (SABiosciences). The Profiler PCR Arrays measure quantitatively the expression of a panel of genes using SYBR Green-based real-time PCR (Kosinski et al., 2007). To assess the transcriptome profiling of apoptotic markers and oxidative stress markers the Human Apoptosis PCR Arrays (PAHS-012Z, SABiosciences) and the Human Oxidative Stress PCR Arrays (PAHS-065Z, SABiosciences) were used.

qRT-PCR Analysis

RNA from purified intestinal crypts was extracted using Trizol Reagent (Invitrogen), and qRT-PCR analysis was performed using TaqMan assays (Life Technologies, Grand Island, N.Y.) according to the manufacturer's instructions. The normalized expression values were determined using the ΔΔCt method. Quantitative reverse transcriptase polymerase chain reaction (qRT-PCR) data were normalized for the expression of ACTB, and ΔΔCt values were calculated. Statistical analysis compared gene expression across all cell populations for each patient via one-way ANOVA followed by Bonferroni post-test for multiple comparisons between the population of interest and all other populations. Statistical analysis was performed also by using the software available RT2 profiler PCR Array Data Analysis (Qiagen). For two groups comparison Student t test was employed. Analysis was performed in triplicates after isolation of fresh crypts and/or after 8 days of culture of miniguts. Table I-B reports the main characteristics of primers used.

TABLE I-B

| Gene Symbol | UniGene # | Refseq Accession # | Band Size (bp) | Reference Position |
|---|---|---|---|---|
| LGR5 | Hs.658889 | NM_003667 | 91 | 1665 |
| EPHB2 | Hs.523329 | NM_004442 | 68 | 2908 |
| TERT | Hs.492203 | NM_198253 | 106 | 1072 |
| ACTB | Hs.520640 | NM_001101 | 174 | 730 |
| IGF-IR | Hs.643120 | NM_000875.3 | 64 | 2248 |
| TMEM219 | Hs.460574 | NM_001083613.1 | 60 | 726 |
| KRT20 | Hs.84905 | NM_019010.2 | 75 | 974 |
| CHGA | Hs.150793 | NM_001275.3 | 115 | 521 |
| EpcaM | Hs.542050 | NM_002354.2 | 95 | 784 |
| LRP1 | Hs.162757 | NM_002332.2 | 64 | 656 |
| TGFbR1 | Hs.494622 | NM_001130916.1 | 73 | 646 |
| TGFbR2 | Hs.604277 | NM_001024847.2 | 70 | 1981 |
| Caspase 8 | Hs.599762 | NM_001080124.1 | 124 | 648 |
| Caspase 9 | Hs.329502 | NM_001229.4 | 143 | 1405 |

ELISA Assay

IGF-I and IGFBP3 levels in the pooled sera/plasma of all groups of subjects and in all groups of treated and untreated mice was assessed using commercially available ELISA kits, according to the manufacturer's instructions (R&D and Sigma).

Human immortalized hepatoma cell line HuH-7 was cultured for 5 days in DMEM 10% FBS at different glucose concentrations: 5.5 mM, 20 mM and 35.5 mM. Culturing supernatant was collected, and IGFBP3 was assessed using an IGFBP3 ELISA kit (Sigma) according to the manufacturer's instructions. Collected cells were separated by trypsin and counted with a hemacytometer.

Insulin levels were assayed with a microparticle enzyme immunoassay (Mercodia Iso-Insulin ELISA) with intra- and inter-assay coefficients of variation (CVs) of 3.0% and 5.0%.

Recombinant Proteins and Interventional Studies

Recombinant human IGF-I (Sigma, I3769), (IGF-I), recombinant human IGFBP3 (Life Technologies, 10430H07H5), (IGFBP3), and anti-IGF-IR (Selleckchem, Boston, OSI-906) were added to crypt cultures at day +2 from isolation. IGFBP3 (Reprokine, Valley Cottage, N.Y.) was administered to naive and to STZ-treated B6 mice at 0.3 mg/mouse/day for 15 days; IGF-I (Reprokine) and ecto TMEM219 were administered in vivo to STZ-treated B6 mice after 2 weeks of diabetes at a dose of 5 μg/mouse/day for 20 days and 100 μg/mouse/day for 15 days respectively. Other molecules tested in in vitro mini-guts assay and added to crypt cultures at day +2 from isolation: Adiponectin (R&D), Thymosin β4 (Abcam), C-reactive protein (Merck Millipore), Cystatin C (Cell Signaling Technologies), Chromogranin A (Life Technologies), Fructosebisphosphate aldolase (Novoprotein), Osteopontin (R&D), Ribonuclease pancreatic (RNASE, Novoprotein), Serum amyloid A protein (Abcam), Mannan-binding lectin serine protease 1 (MASPI, Novoprotein), Tumor necrosis factor-alpha (TNF-alpha, R&D), FaS Ligand (FasL, R&D). Hydrogen peroxide ($H_2O_2$, 50 μM) was also tested in the mini-guts assay.

Generation of Recombinant Human Ecto TMEM219

Recombinant human ecto-TMEM219 was generated using *E. Coli* as expression host for synthesis.

Briefly, gene sequence of extracellular TMEM219 was obtained:

(SEQ ID NO. 2)
THRTGLRSPDIPQDWVSFLRSFGQLTLCPRNGTVTGKWRGSHVVGLLTTL

NFGDGPDRNKTRTFQATVLGSQMGLKGSSAGQLVLITARVTTERTAGTCL

-continued

YFSAVPGILPSSQPPISCSEEGAGNATLSPRMGEECVSVWSHEGL VLTK

LL TSEELALCGSR.

The DNA sequence of extracellular TMEM219 was cloned into a high copy-number plasmid containing the lac promoter, which is then transformed into the bacterium *E. coli*. Addition of IPTG (a lactose analog) activated the lac promoter and caused the bacteria to express extracellular TMEM219 (ecto TMEM219). SDS-P AGE and Western Blot were used to confirm purity higher than 90%. The molecular weight of the new generated protein recombinant human ecto TMEM219 was 80 kda.

Crypts from healthy subjects were isolated and cultured as previously described and ecto TMEM219 was added to the culture at three concentrations (260 ng/ml, 130 ng/ml and 75 ng/ml) as compared to IGFBP3 concentration used (2:1, 1:1 and 1:2) and appropriate controls were set up for each concentration. After 8 days of culture, caspase 8 and 9 expression, CoSCSC signature markers (EphB2 and LGR5) expression, number of developed mini-guts, were further assessed.

Small RNA Interference

Isolated crypts obtained from healthy subjects were grown to generate in vitro mini-guts in complete medium and in culturing medium modified by adding high glucose and long-standing T1D serum as previously described (see in vitro mini-gut generation study in online methods). After 72 h of culture, which allowed the crypts to recover, 750 ng of small interfering RNA (siRNA; Flexitube siRNA SI04381013, Qiagen, Valencia, Calif.) in 100 μl culture medium without serum and with 6 μl HiPerFect Transfection Reagent (Qiagen) were incubated at room temperature to allow for the formation of transfection complexes. Crypts were incubated with these transfection complexes under their normal growth conditions for 6 h. Analysis of gene silencing was performed at 24, 48 and 72 h by evaluating the percentage of normal mini-gut development. Control siRNA was used as a negative control to confirm the effect of gene silencing.

Proteomic Analysis

8 μl of pooled serum from 10 patients per group were depleted using a ProteoPrep 20 spin column (Sigma), thus allowing for the removal of the 20 highly abundant proteins. The procedure was twice repeated in order to obtain ~99% depletion, according to the manufacturer's instructions. The recovered supernatant was analyzed to determine total protein concentration using the Direct Detect IR spectrophotometer and BSA as a standard. In order to obtain enough protein for proteomic analysis, 32 μl from each pool were processed as above described. 40 μg of total protein from each sample was in-solution digested using the Filter Aided Sample Preparation (FASP) protocol as reported in the literature (Wisniewski et al., 2009). Samples were desalted using C18 homemade tip columns (C18 Empore membrane, 3M) and injected into a capillary chromatographic system (EasyLC, Proxeon Biosystems, Thermo Scientific). Peptide separations were performed on a homemade 25 cm reverse phase spraying fused silica capillary column, packed with 3 m ReproSil Pur 120 C18-AQ. A gradient of eluents A (pure water with 2% v/v ACN, 0.5% v/v acetic acid) and B (ACN with 20% v/v pure water with 0.5% v/v acetic acid) was used to achieve separation (0.15 μL/minute flow rate) (from 10 to 35% B in 230 minutes, from 35 to 50% B in 5 minutes and from 50 to 70% B in 30 minutes). Mass spectrometry analysis was performed using an LTQ-Orbitrap mass spectrometer (Thermo Scientific, Waltham, Mass.) equipped with a nanoelectrospray ion source (Proxeon Biosystems). Full scan mass spectra were acquired with the lock-mass option and resolution set to 60,000. The acquisition mass range for each sample was from m/z 300 to 1750 Da. The ten most intense doubly and triply charged ions were selected and fragmented in the ion trap using a normalized collision energy 37%. Target ions already selected for the MS/MS were dynamically excluded for 120 seconds. All MS/MS samples were analyzed using Mascot (v.2.2.07, Matrix Science, London, UK) search engine to search the UniProt_Human Complete Proteome_cp_hum_2013_12. Searches were performed with trypsin specificity, two missed cleavages allowed, cysteine carbamidomethylation as fixed modification, acetylation at protein N-terminus, and oxidation of methionine as variable modification. Mass tolerance was set to 5 ppm and 0.6 Da for precursor and fragment ions, respectively. To quantify proteins, the raw data were loaded into the MaxQuant software version 1.3.0.5 (Cox et al., 2011). Label-free protein quantification was based on the intensities of precursors. Peptides and proteins were accepted with an FDR less than 1%, two minimum peptides per protein. The experiments were performed in technical triplicates. The complete dataset of proteins, obtained by proteomic analysis (Table I-C), was analyzed by Student's t-test using MeV software v. 4_8_1. 47 proteins, which were significantly different (p-value<0.01) in control pool versus T1D-ESDR pool, were further submitted to hierarchical clustering analysis.

TABLE I-C

List of quantified proteins identified by proteomic analysis. The table reports correspondence between numbers and names of proteins detected by proteomic analysis and is shown as a heat-map in FIG. 10.

| Original row | Protein names |
| --- | --- |
| 1 | 14-3-3 protein zeta/delta |
| 4 | Actin, cytoplasmic 1; Actin, cytoplasmic 1, N-terminally processed; Actin, cytoplasmic 2; Actin, cytoplasmic 2, N-terminally processed |
| 5 | Adiponectin |
| 6 | Afamin |
| 8 | Alpha-1-antichymotrypsin; Alpha-1-antichymotrypsin His-Pro-less |
| 9 | Alpha-1-antitrypsin; Short peptide from AAT |
| 12 | Alpha-2-HS-glycoprotein; Alpha-2-HS-glycoprotein chain A; Alpha-2-HS-glycoprotein chain B |
| 13 | Alpha-2-macroglobulin |
| 14 | Alpha-actinin-1 |

TABLE I-C-continued

List of quantified proteins identified by proteomic analysis. The table reports correspondence between numbers and names of proteins detected by proteomic analysis and is shown as a heat-map in FIG. 10.

| Original row | Protein names |
|---|---|
| 16 | Angiotensinogen; Angiotensin-1; Angiotensin-2; Angiotensin-3 |
| 17 | Antithrombin-III |
| 18 | Apolipoprotein A-I; Truncated apolipoprotein A-I |
| 20 | Apolipoprotein A-IV |
| 21 | Apolipoprotein B-100; Apolipoprotein B-48 |
| 22 | Apolipoprotein C-I; Truncated apolipoprotein C-I |
| 23 | Apolipoprotein C-II |
| 24 | Apolipoprotein C-III |
| 25 | Apolipoprotein C-IV |
| 26 | Apolipoprotein D |
| 28 | Apolipoprotein F |
| 29 | Apolipoprotein L1 |
| 31 | Apolipoprotein(a) |
| 34 | Attractin |
| 35 | Basement membrane-specific heparan sulfate proteoglycan core protein; Endorepellin; LG3 peptide |
| 36 | Beta-2-glycoprotein 1 |
| 37 | Beta-2-microglobulin; Beta-2-microglobulin form pI 5.3 |
| 39 | Beta-Ala-His dipeptidase |
| 42 | C4b-binding protein beta chain |
| 43 | Cadherin-1; E-Cad/CTF1; E-Cad/CTF2; E-Cad/CTF3 |
| 44 | Cadherin-13 |
| 45 | Cadherin-5 |
| 46 | Calreticulin |
| 50 | Carboxypeptidase N subunit 2 |
| 51 | Cartilage oligomeric matrix protein |
| 54 | CD44 antigen |
| 57 | Ceruloplasmin |
| 59 | Chromogranin-A; Vasostatin-1; Vasostatin-2; EA-92; ES-43; Pancreastatin; SS-18; WA-8; WE-14; LF-19; AL-11; GV-19; GR-44; ER-37 |
| 60 | Clusterin; Clusterin beta chain; Clusterin alpha chain; Clusterin |
| 62 | Coagulation factor V; Coagulation factor V heavy chain; Coagulation factor V light chain |
| 63 | Coagulation factor X; Factor X light chain; Factor X heavy chain; Activated factor Xa heavy chain |
| 65 | Cofilin-1 |
| 66 | Collagen alpha-3(VI) chain |
| 68 | Complement C1r subcomponent; Complement C1r subcomponent heavy chain; Complement C1r subcomponent light chain |
| 71 | Complement C2; Complement C2b fragment; Complement C2a fragment |
| 72 | Complement C3; Complement C3 beta chain; Complement C3 alpha chain; C3a anaphylatoxin; Complement C3b alpha chain; Complement C3c alpha chain fragment 1; Complement C3dg fragment; Complement C3g fragment; Complement C3d fragment; Complement C3f fragment; Complement C3c alpha chain fragment 2 |
| 73 | Complement C4-A; Complement C4 beta chain; Complement C4-A alpha chain; C4a anaphylatoxin; C4b-A; C4d-A; Complement C4 gamma chain |
| 74 | Complement C4-B; Complement C4 beta chain; Complement C4-B alpha chain; C4a anaphylatoxin; C4b-B; C4d-B; Complement C4 gamma chain |
| 75 | Complement C5; Complement C5 beta chain; Complement C5 alpha chain; C5a anaphylatoxin; Complement C5 alpha chain |
| 76 | Complement component C1q receptor |
| 77 | Complement component C6 |
| 78 | Complement component C7 |
| 84 | Complement factor D |
| 88 | Complement factor I; Complement factor I heavy chain; Complement factor I light chain |
| 89 | Corticosteroid-binding globulin |
| 90 | C-reactive protein; C-reactive protein(1-205) |
| 91 | Cystatin-C |
| 92 | Cystatin-M |
| 95 | EGF-containing fibulin-like extracellular matrix protein 1 |
| 96 | Endothelial protein C receptor |
| 97 | Extracellular matrix protein 1 |
| 98 | Extracellular superoxide dismutase [Cu—Zn] |
| 99 | Fetuin-B |
| 100 | Fibrinogen alpha chain; Fibrinopeptide A; Fibrinogen alpha chain |
| 101 | Fibrinogen beta chain; Fibrinopeptide B; Fibrinogen beta chain |
| 102 | Fibrinogen gamma chain |
| 103 | Fibronectin; Anastellin; Ugl-Y1; Ugl-Y2; Ugl-Y3 |
| 104 | Fibulin-1 |
| 105 | Ficolin-3 |

TABLE I-C-continued

List of quantified proteins identified by proteomic analysis. The table reports correspondence between numbers and names of proteins detected by proteomic analysis and is shown as a heat-map in FIG. 10.

| Original row | Protein names |
|---|---|
| 106 | Fructose-bisphosphate aldolase A; Fructose-bisphosphate aldolase |
| 107 | Galectin-3-binding protein |
| 108 | Gamma-glutamyl hydrolase |
| 109 | Gelsolin |
| 111 | Glyceraldehyde-3-phosphate dehydrogenase |
| 112 | Haptoglobin; Haptoglobin alpha chain; Haptoglobin beta chain |
| 117 | Heparin cofactor 2 |
| 122 | Hypoxia up-regulated protein 1 |
| 123 | Ig alpha-1 chain C region |
| 125 | Ig gamma-1 chain C region |
| 126 | Ig gamma-2 chain C region |
| 127 | Ig gamma-3 chain C region |
| 129 | Ig heavy chain V-II region SESS; Ig heavy chain V-II region OU |
| 130 | Ig heavy chain V-III region BRO; Ig heavy chain V-III region TEI; Ig heavy chain V-III region BUT; Ig heavy chain V-III region WEA |
| 134 | Ig heavy chain V-III region VH26 |
| 135 | Ig kappa chain C region |
| 136 | Ig kappa chain V-I region EU; Ig kappa chain V-I region CAR |
| 142 | Ig kappa chain V-III region WOL; Ig kappa chain V-III region SIE; Ig kappa chain V-III region Ti; Ig kappa chain V-III region GOL |
| 144 | Ig kappa chain V-IV region Len |
| 145 | Ig lambda chain V-I region HA; Ig lambda chain V-I region WAH; Ig lambda chain V-II region MGC; Ig lambda chain V-II region WIN |
| 146 | Ig lambda chain V-III region LOI |
| 148 | Ig lambda-2 chain C regions; Ig lambda-3 chain C regions; Ig lambda-6 chain C region |
| 153 | Immunoglobulin lambda-like polypeptide 5; Ig lambda-1 chain C regions |
| 154 | Insulin-like growth factor-binding protein 2 |
| 155 | Insulin-like growth factor-binding protein 3 |
| 156 | Insulin-like growth factor-binding protein 6 |
| 158 | Inter-alpha-trypsin inhibitor heavy chain H1 |
| 159 | Inter-alpha-trypsin inhibitor heavy chain H2 |
| 160 | Inter-alpha-trypsin inhibitor heavy chain H3 |
| 161 | Inter-alpha-trypsin inhibitor heavy chain H4; 70 kDa inter-alpha-trypsin inhibitor heavy chain H4; 35 kDa inter-alpha-trypsin inhibitor heavy chain H4 |
| 164 | Keratin, type I cytoskeletal 10 |
| 165 | Keratin, type I cytoskeletal 9 |
| 166 | Keratin, type II cytoskeletal 1 |
| 167 | Kininogen-1; Kininogen-1 heavy chain; T-kinin; Bradykinin; Lysyl-bradykinin; Kininogen-1 light chain; Low molecular weight growth-promoting factor |
| 168 | Leucine-rich alpha-2-glycoprotein |
| 171 | L-lactate dehydrogenase B chain; L-lactate dehydrogenase |
| 174 | Lumican |
| 175 | Lymphatic vessel endothelial hyaluronic acid receptor 1 |
| 176 | Lysozyme C |
| 178 | Mannan-binding lectin serine protease 1; Mannan-binding lectin serine protease 1 heavy chain; Mannan-binding lectin serine protease 1 light chain |
| 180 | Monocyte differentiation antigen CD14; Monocyte differentiation antigen CD14, urinary form; Monocyte differentiation antigen CD14, membrane-bound form |
| 181 | Multimerin-1; Platelet glycoprotein Ia*; 155 kDa platelet multimerin |
| 183 | Neudesin |
| 185 | Neural cell adhesion molecule L1-like protein; Processed neural cell adhesion molecule L1-like protein |
| 187 | Osteopontin |
| 188 | Peptidase inhibitor 16 |
| 189 | Peptidyl-prolyl cis-trans isomerase A; Peptidyl-prolyl cis-trans isomerase |
| 192 | Phosphatidylethanolamine-binding protein 4 |
| 194 | Pigment epithelium-derived factor |
| 197 | Plasminogen; Plasmin heavy chain A; Activation peptide; Angiostatin; Plasmin heavy chain A, short form; Plasmin light chain B |
| 198 | Platelet basic protein; Connective tissue-activating peptide III; TC-2; Connective tissue-activating peptide III(1-81); Beta-thromboglobulin; Neutrophil-activating peptide 2(74); Neutrophil-activating peptide 2(73); Neutrophil-activating peptide 2; TC-1; Neutrophil-activating peptide 2(1-66); Neutrophil-activating peptide 2(1-63) |
| 199 | Platelet glycoprotein Ib alpha chain; Glycocalicin |
| 200 | Plexin domain-containing protein 2 |
| 203 | Profilin-1 |
| 204 | Proline-rich acidic protein 1 |

TABLE I-C-continued

List of quantified proteins identified by proteomic analysis. The table reports correspondence between numbers and names of proteins detected by proteomic analysis and is shown as a heat-map in FIG. 10.

| Original row | Protein names |
|---|---|
| 205 | Properdin |
| 206 | Prostaglandin-H2 D-isomerase |
| 207 | Protein AMBP; Alpha-1-microglobulin; Inter-alpha-trypsin inhibitor light chain; Trypstatin |
| 209 | Prothrombin; Activation peptide fragment 1; Activation peptide fragment 2; Thrombin light chain; Thrombin heavy chain |
| 212 | Receptor-type tyrosine-protein phosphatase gamma |
| 213 | Retinol-binding protein 4; Plasma retinol-binding protein(1-182); Plasma retinol-binding protein(1-181); Plasma retinol-binding protein(1-179); Plasma retinol-binding protein(1-176) |
| 214 | Rho GDP-dissociation inhibitor 2 |
| 215 | Ribonuclease pancreatic |
| 216 | Scavenger receptor cysteine-rich type 1 protein M130; Soluble CD163" |
| 217 | Secreted and transmembrane protein 1 |
| 221 | Serotransferrin |
| 222 | Serum albumin |
| 223 | Serum amyloid A protein |
| 225 | Serum amyloid P-component; Serum amyloid P-component(1-203) |
| 226 | Serum paraoxonase/arylesterase 1 |
| 228 | SPARC-like protein 1 |
| 230 | Talin-1 |
| 232 | Tenascin-X |
| 233 | Tetranectin |
| 234 | Thrombospondin-1 |
| 235 | Thrombospondin-4 |
| 236 | Thymosin beta-4; Hematopoietic system regulatory peptide |
| 237 | Thyroxine-binding globulin |
| 239 | Transgelin-2 |
| 240 | Trans-Golgi network integral membrane protein 2 |
| 242 | Tropomyosin alpha-4 chain |
| 243 | Vascular cell adhesion protein 1 |
| 244 | Vasorin |
| 245 | Vinculin |
| 247 | Vitamin K-dependent protein C; Vitamin K-dependent protein C light chain; Vitamin K-dependent protein C heavy chain; Activation peptide |
| 248 | Vitamin K-dependent protein S |
| 249 | Vitamin K-dependent protein Z |
| 250 | Vitronectin; Vitronectin V65 subunit; Vitronectin V10 subunit; Somatomedin-B |
| 251 | von Willebrand factor; von Willebrand antigen 2 |
| 254 | Zinc-alpha-2-glycoprotein |
| 258 | Vitamin D-binding protein |
| 259 | Complement factor H |
| 266 | Fibulin-1 |
| 267 | Mannan-binding lectin serine protease 1 |
| 270 | Complement factor H-related protein 4 |

Strategy to Select Candidate Proteins

Among the 46 factors that segregated separately in long-standing T1D subjects and healthy controls, the inventors first selected those with a more significant difference in LFQ intensity in comparing the two groups (p>0.005), leading to the exclusion of 12 factors (FIG. 16). Next, the inventors evaluated whether altered factors may be associated with intestinal disorders and/or with the development of diabetes by searching for already reported studies and publications in the field. This led us to exclude other 12 factors. The inventors also excluded those factors mainly related to the lymphoid compartment (n=5). The inventors ended up with 17 factors. The inventors excluded cell-membrane proteins (n=4) and proceeded with testing the remaining (n=13) in the mini-gut assay. Two factors were not available to be tested in vitro. The inventors tested n=1 proteins in total.

Animal Studies

C57BL/6 (B6) mice were obtained from the Jackson Laboratory, Bar Harbor, Me. All mice were cared for and used in accordance with institutional guidelines approved by the Harvard Medical School Institutional Animal Care and Use Committee. Mice were rendered diabetic with streptozotocin injection (225 mg/kg, administered i.p.; Sigma). Diabetes was defined as blood glucose levels >250 mg/dL for 3 consecutive measures. Diabetic enteropathy was assessed as follows: briefly, the entire intestine was extracted from sacrificed mice and flushed with PBS. The extreme part of the colon was then cut and divided in two pieces. One piece of colon tissue was directly submerged in formalin while the other was cut longitudinally to expose the lumen and the internal mucosa and then submerged in formalin. Tissue was then paraffin embedded and processed for H&E and immunostaining. In addition, colonic tissue was also cut and isolation of colonic stem cells was performed as previously described (Merlos-Suarez et al., 2011). Briefly, colon was cut into 2-4 mm pieces and the fragments were washed in 30 mL ice-cold PBS. Fragments were the transferred in 50 ml tubes containing pre-warmed 20 mM EDTA-PBS and incubated at 37° C. for 30 min. After incubation the suspended tissue was transferred into tube containing 30 ml cold PBS and centrifuged. Crypts were resuspended in 13 ml cold DMEMF12, washed with PBS and digested in 5-10 ml of trypsin/DNAse solution at 37° C. for 30 min. Crypts were then resuspended in DMEMF12/EDTA, filtered in 40 micron strainer twice and washed.

Finally, crypts were then resuspended in flow medium (DMEM+FBS+ EDTA) and stained for anti EphB2-APC (R&D), mouse anti-CD45-PeRCP and mouse anti-CD11b-PE (BD Pharmingen). Samples were run using a FACSCalibur Analyzer and data analyzed with FlowJo.

Part of the tissue was also snap frozen and stored in Tryzol to perform RT-PCR studies for the following markers:

| Gene Symbol: | UniGene #: | Refseq Accession #: | Band Size (bp): | Reference Position: |
|---|---|---|---|---|
| LGR5 | Mm.42103 | NM_010195.2 | 64 | 571 |
| EPHB2 | Mm.250981 | NM_010142.2 | 85 | 1696 |
| Casp8 | Mm.336851 | NM_001080126.1 | 96 | 1525 |
| Casp9 | Mm.88829 | NM_001277932.1 | 68 | 377 |
| GAPDH | Mm. 304088 | NM_008084.2 | 107 | 75 |

Finally, plasma and serum were collected to perform analysis of IGF-I (IGF-I ELISA kit, R&D), IGFBP3 (IGFBP3 ELISA kit, R&D) and insulin levels (Mercodia Mouse Insulin ELISA kit). Blood glucose was monitored twice a week for the 8 weeks in order to confirm diabetes onset and permanence.

Statistical Analysis

Data are presented as mean and standard error of the mean (SEM) and were tested for normal distribution with the Kolmogorov-Smirnov test and for homogeneity of variances with Levene's test. The statistical significance of differences was tested with two-tailed t-test and the chi-square ($x^2$) tests. Significance between the two groups was determined by two-tailed unpaired Student's t test. For multiple comparisons, the ANOVA test with Bonferroni correction was employed. All data were entered into Statistical Package for the Social Science (SPSS®, IBM®, SPSS Inc., Chicago, Ill.) and analyzed. Graphs were generated using GraphPad Prism version 5.0 (GraphPad Software, La Jolla, Calif.). All statistical tests were performed at the 5% significance level.

Results

Intestinal Dysfunction and Clinical Symptoms are Present in Long-Standing T1D

Figure 1B:
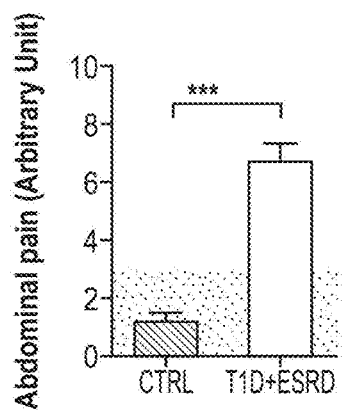
Figure 1C:
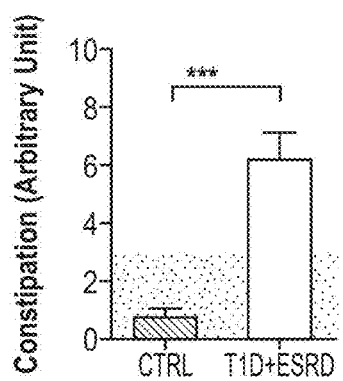
Figure 1D:
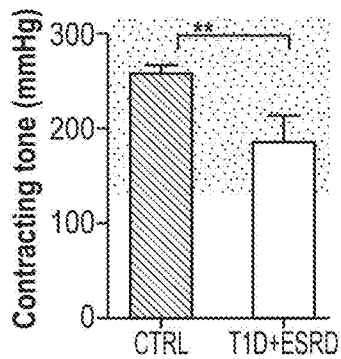
FIGS. 1D-1F are bar graphs reporting the measurements of anorectal sphincter contracting tone (mmHg), reflex response (ml) and urgency volume (ml) by anorectal manometry in healthy subjects (CTRL) and long-standing T1D individuals (T1D+ESRD). Gray area indicates normal range for the parameter. N=20 CTRL and n=60 T1D+ESRD individuals were included in the evaluation.
Figure 1E:
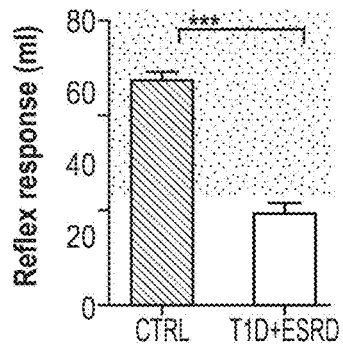
Figure 1F:
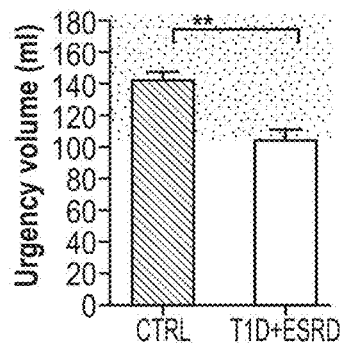
Figure 1G:
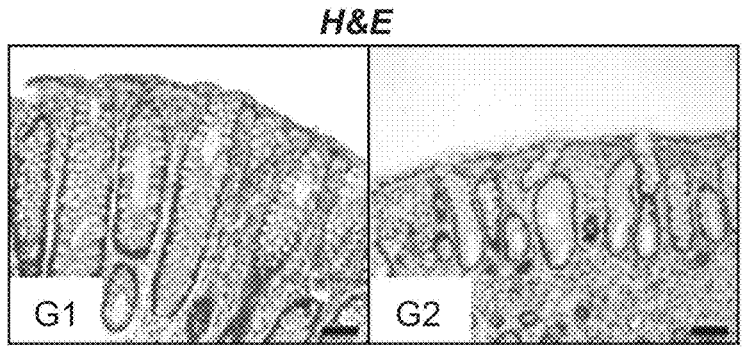
Figure 1H:
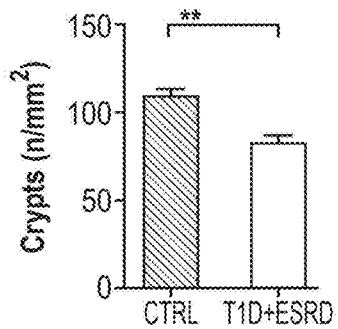
Figure 1I:
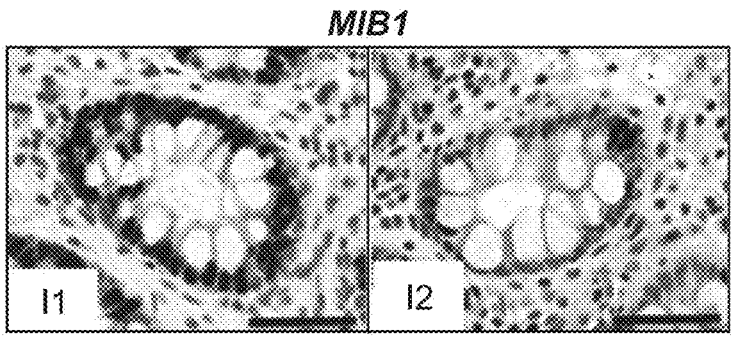
Figure 1J:
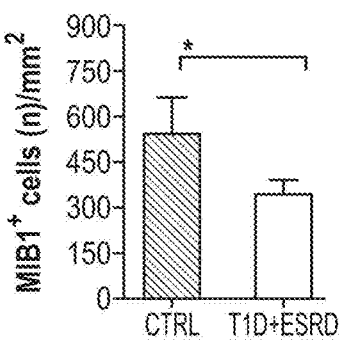

The inventors first characterized intestinal morphology and function in a population of individuals with long-standing T1D and end stage renal disease (T1D+ESRD) and in healthy subjects (CTRL). Severe intestinal symptoms, such as diarrhea, abdominal pain and constipation, were evident in T1D+ESRD individuals as assessed using the Gastrointestinal Symptom Rating Scale (GSRS) questionnaire (FIGS. 1A-1C). Symptoms were associated with abnormalities in anorectal sphincter function (FIGS. 1D-1F). The intestinal mucosa was altered in individuals with T1D+ESRD as compared to healthy subjects, with lower number of crypts, distortion and zonal sclerosis of the lamina propria (FIG. 1G, panels labeled G1-G2; FIG. 1H). A significant reduction in epithelial cell proliferation as assessed by Ki67 (MIB1 antibody) staining (FIG. 1I, panels labeled I1-I2; FIG. 1J), signs of neural degeneration (FIG. 1K, panels labeled K1-K2; FIG. 1L) and reduction in serotonin expression in intestinal neuroendocrine cells (FIG. 1M, panels labeled M1-M2; FIG. 1N) were observed, confirming the presence of DE in these individuals.

CoSCs are Altered in Long-Standing T1D

Figure 2I:
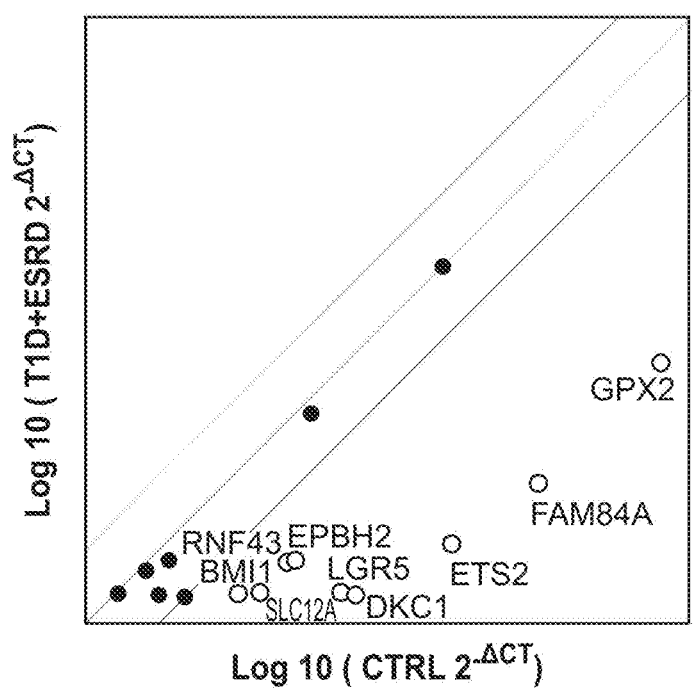
FIG. 2I is a scatter plot representing the CoSC signature markers and stem cell transcriptome profiling examined in freshly isolated intestinal crypts of n=10 healthy subjects (CTRL) and n=10 long-standing T1D individuals (T1D+ESRD).
Figures 8A, 8B:
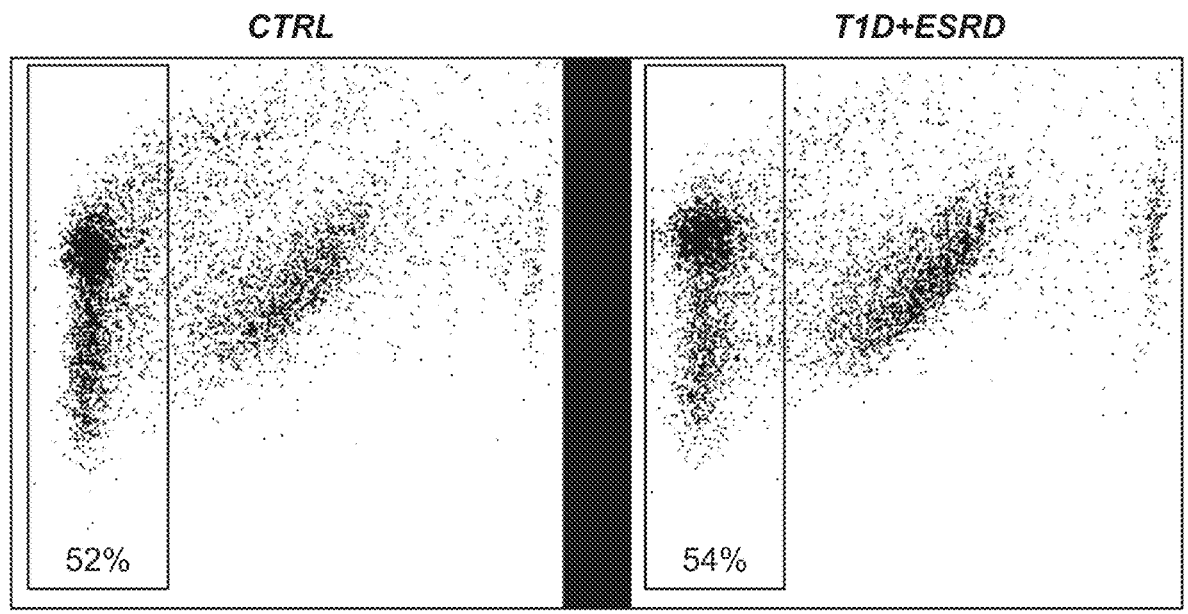
Figure 8C:
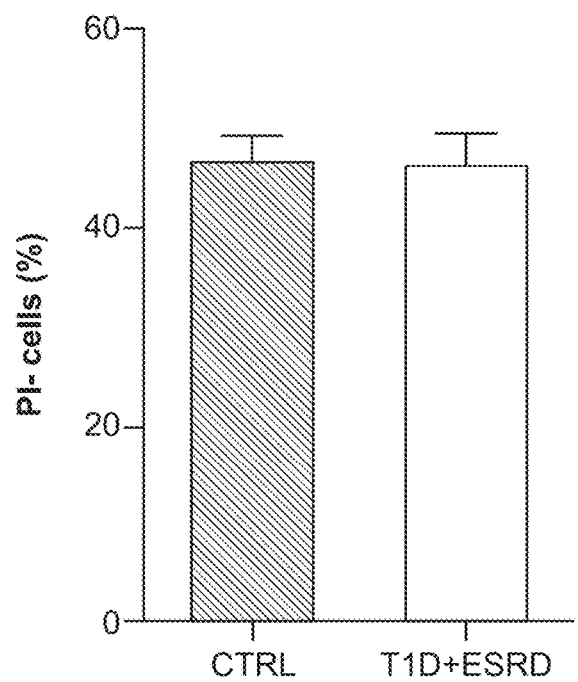
FIG. 8C provides bar graphs depicting results of flow cytometric analysis of PI$^{31}$ cells in freshly isolated crypts (n=10 CTRL and n=10 T1D+ESRD).
Figure 8D:
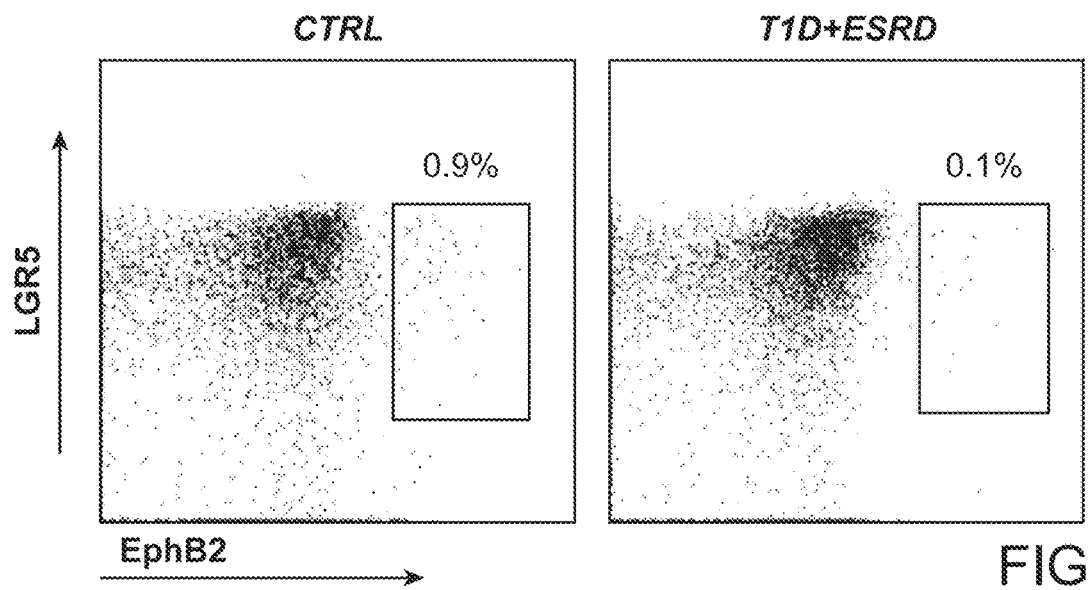
FIGS. 8D-8E are flow dot plots of EphB2$^{hi}$LGR5$^+$ (FIG. 8D) and EphB2$^+$h-TERT$^+$ cells in healthy subjects (CTRL) and long-standing T1D individuals (T1D+ESRD).
Figure 8E:
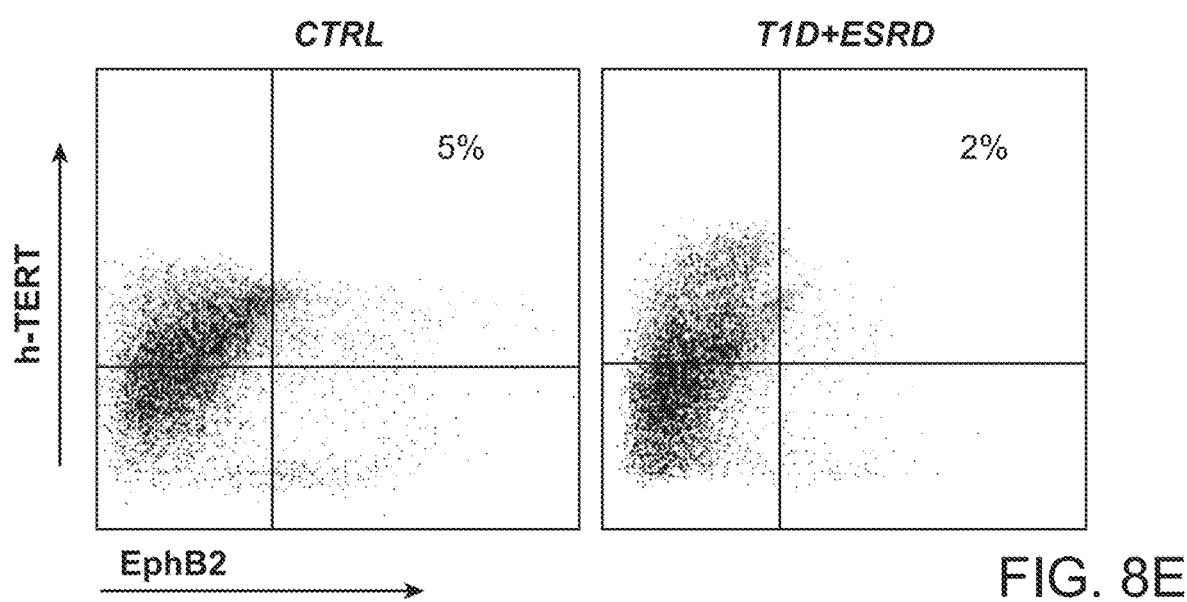
Figure 8F:
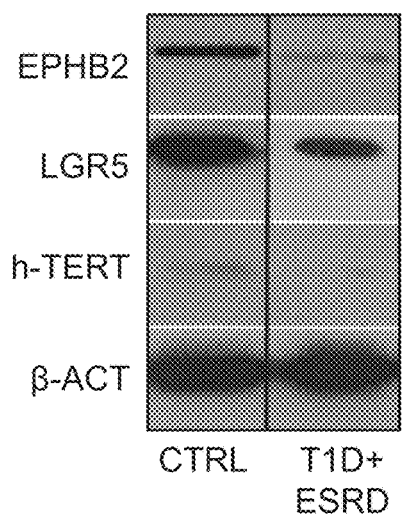
FIG. 8F is a Western blot analysis (cropped blots) confirming low expression of EphB2, LGR5, h-TERT in in vitro isolated intestinal crypts of long-standing T1D individuals (T1D+ESRD). Full-length blots are presented in FIG. 5G. N=5 subjects per group were evaluated.
Figure 8G:
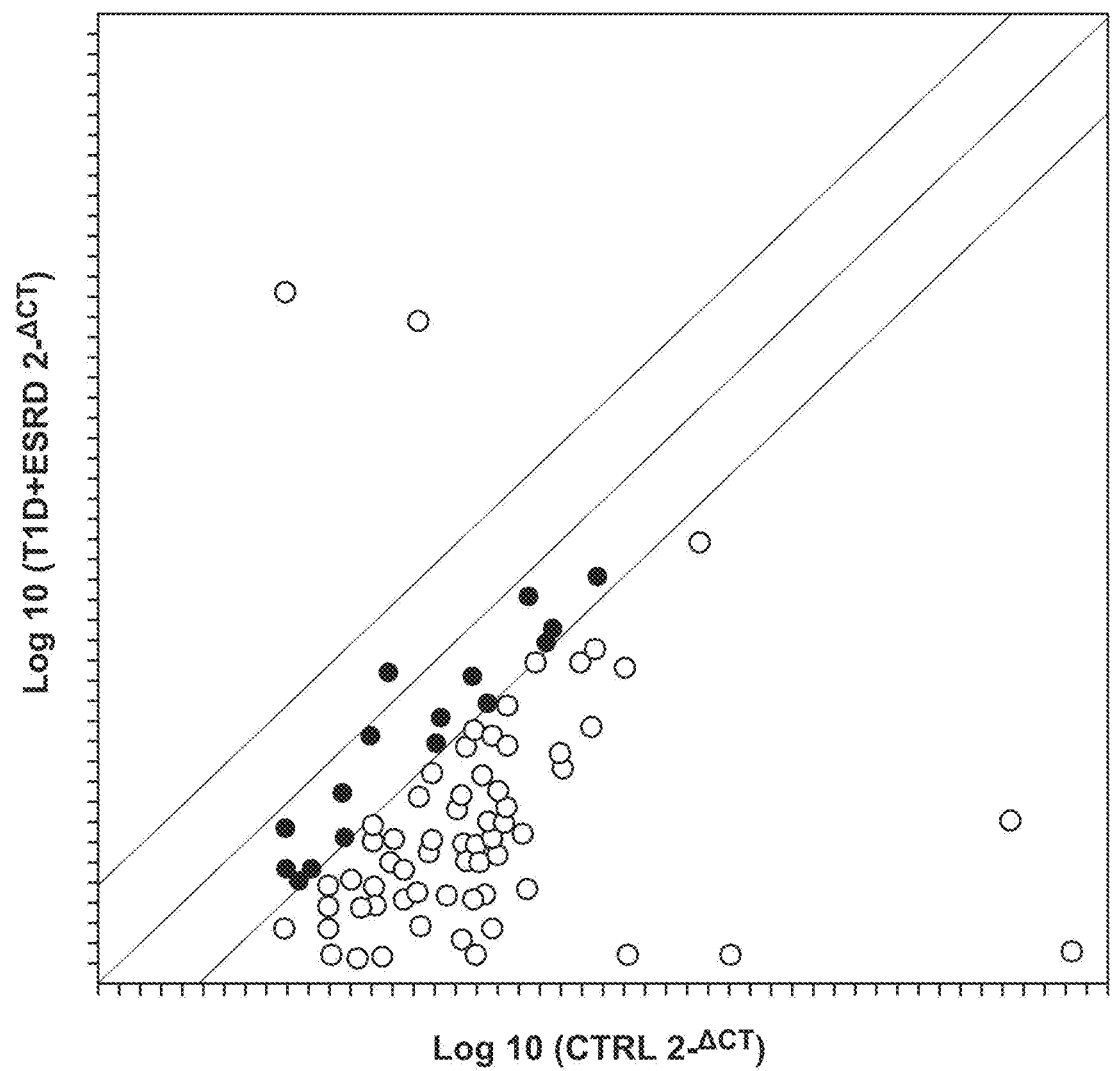
FIG. 8G is a scatter plot representing the stem cell transcriptome profiling examined in freshly isolated intestinal crypts of healthy subjects (CTRL) and long-standing T1D individuals (T1D+ESRD). A table summarizes genes and pathways analyzed (Table S1). N=10 subjects per group were evaluated.

The characterization of colonic crypts, revealed a significant reduction in EphB2$^+$ expression and in the number of aldehyde dehydrogenase (Aldh)$^+$immunoreactive cells, both markers of local stem cells (Carpentino et al., 2009; Jung et al., 2011), in T1D+ESRD individuals as compared to healthy subjects (FIG. 1O, panels labeled O1-O2; FIG. 1P; FIG. 1Q, panels labeled Q1-Q2; FIG. 1R). A profound decrease was evident, upon gating on PI cells at FACS analysis (FIGS. 8A-8C), in the percentage of EphB2$^{hi}$, EphB2$^{hi}$+LGR5$^+$ and EphB2$^+$h-TERT$^+$ cells isolated from intestinal crypts obtained from T1D+ESRD individuals as compared to healthy subjects (FIGS. 2A-2B; FIGS. 2C-2E; FIGS. 8D-8E) and was confirmed by RT-PCR (FIGS. 2F-2H) and western blot (WB) analysis (FIG. 8F). Transcriptome profiling of crypts obtained from T1D+ESRD documented a decreased expression of Notch pathway (Notch1 and 2, JAG1, Dll1, Sox1 and 2), Wnt pathway (APC, FZD1, DKC1, ETS2, FAM84A, GPX2, RNF43) and BMP pathway (BMP1, BMP2, BMP3) genes, previously known pathways that control CoSCs, as compared to the expression of these genes in healthy subjects (FIG. 8G and Table II).

TABLE II

List of up and down regulated stem cell target genes identified by transcriptomic profiling in CTRL vs. T1D + ESRD freshly isolated colonic crypts (at least p < 0.05).

| Down-regulated genes | | | Up-regulated genes |
|---|---|---|---|
| ACTC1 | APC | CD44 | DVL1 |
| BTRC | SOX1 | SOX2 | WNT1 |
| CCND2 | FZD1 | ADAR | |
| ACAN | ALPI | CD8A | |
| COL1A1 | COL2A1 | COL9A1 | |
| BMP1 | BMP2 | BMP3 | |
| CCNA2 | CCNE1 | CDC42 | |
| CDK1 | | | |
| CTNNA1 | CXCL12 | PARD6A | |
| CD3D | CD8B | MME | |
| CD4 | | | |
| DLL1 | HDAC2 | NOTCH1 | |
| DLL3 | JAG1 | NOTCH2 | |
| DTX2 | KAT2A | NUMB | |
| EP300 | | | |
| FGF2 | FGF3 | FGFR1 | |
| GDF3 | ISL1 | KRT15 | |
| MSX1 | MYOD1 | T | |
| GJA1 | GJB1 | GJB2 | |
| KAT8 | RB1 | h-TERT | |
| NCAM1 | SIGMAR1 | TUBB3 | |
| ABCG2 | ALDH1A1 | | |
| PDX1 | | | |
| IGF-I | | | |
| DHH | | | |
| BGLAP | | | |

Analysis of—CoSC signature genes revealed that LGR5, EphB2 (Gracz et al., 2013; Merlos-Suarez et al., 2011), h-TERT (Breault et al., 2008) and other intestinal stem cell marker genes (Hughes et al., 2011; Munoz et al., 2012; Ziskin et al., 2013) were significantly underexpressed in T1D+ESRD as compared to healthy subjects as well (FIG. 2I), confirming that the CoSCs are altered in individuals with DE.

In Vitro Generation of Mini-Guts is Altered in Long-Standing TID

Figures 2M, 2N:
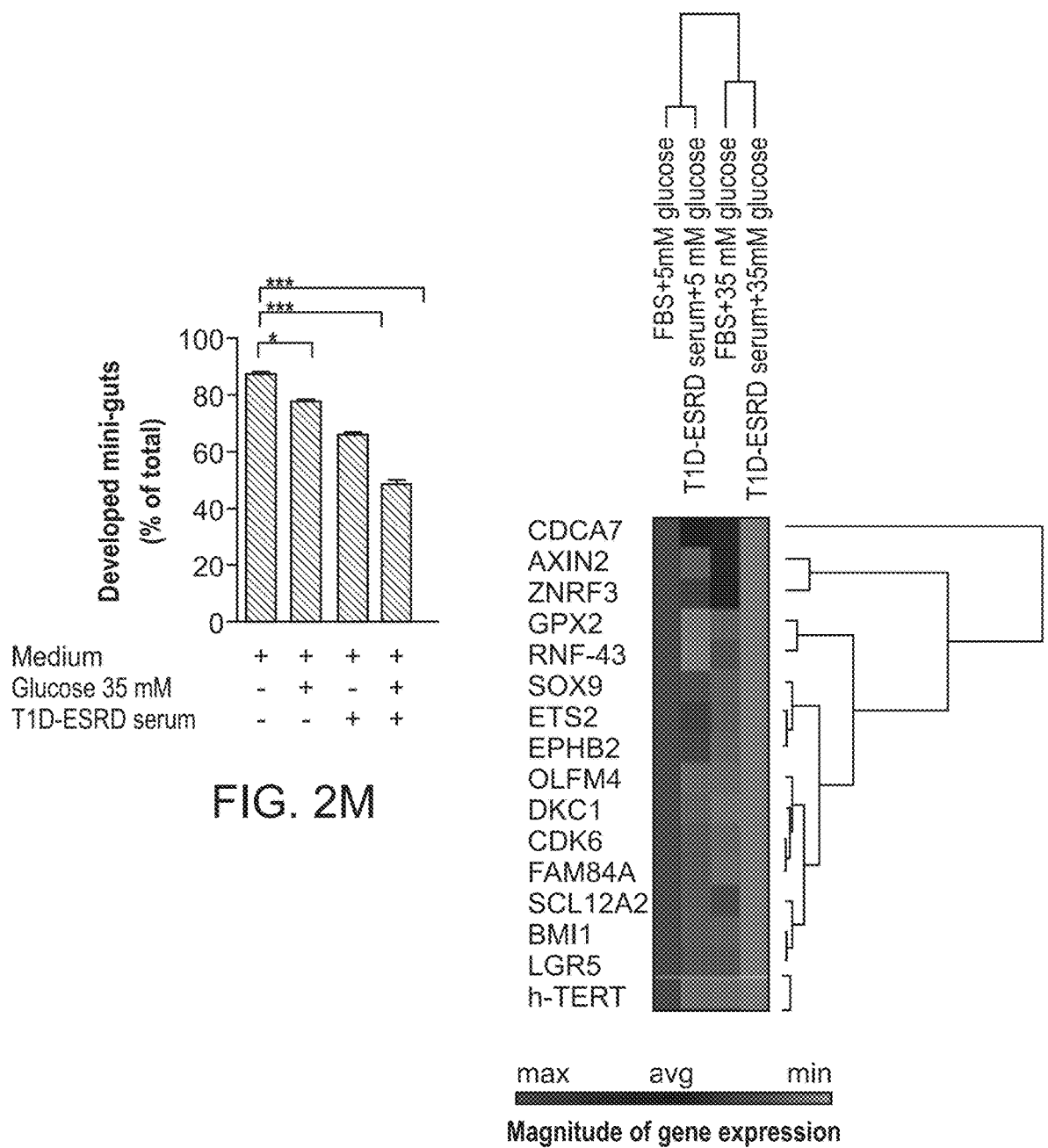
Figures 8H, 8I:
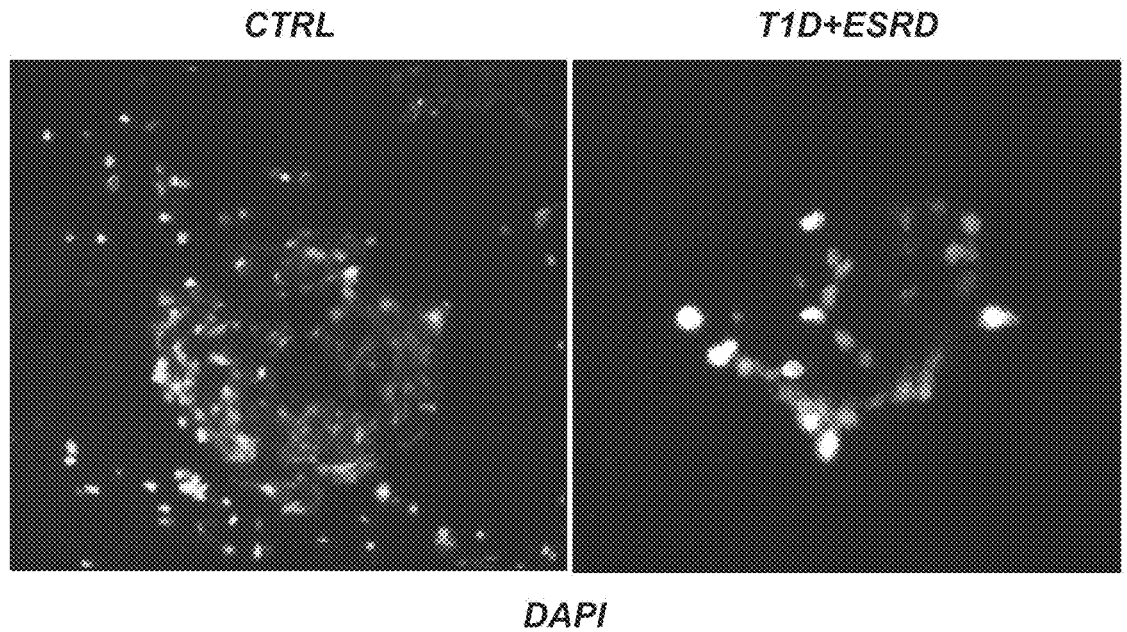
FIGS. 8H-8I are representative images of freshly isolated crypts obtained from healthy subjects and long-standing T1D individuals stained with DAPI. 20× magnification.
Figure 8J:
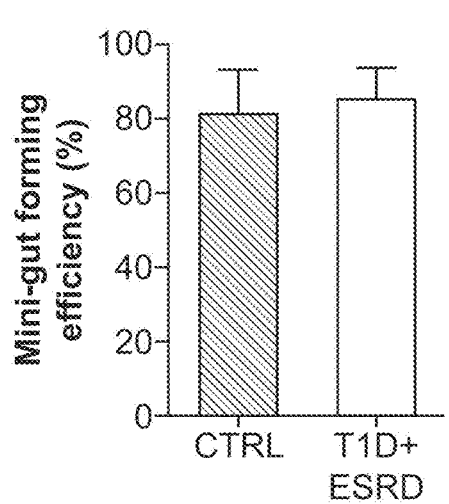
FIG. 8J is a bar graph representing the percentage of mini-guts forming efficiency of plated crypts obtained from healthy subjects and long-standing T1D individuals at 12 hours. N=10 subjects per group were evaluated.

In order to evaluate CoSC self-renewal properties, the inventors used the in vitro mini-gut assay. Indeed, crypts isolated from T1D+ESRD individuals and cultured in vitro for 8 days formed small spheroid mini-guts that failed to grow as compared to healthy subjects (FIG. 2J, panels labeled JI, J2; FIG. 2K), despite a comparable viability (FIGS. 8H-8I) and efficiency of forming mini-guts in both groups (FIG. 8J). To begin to elucidate the effect of circulating factors and high glucose on CoSCs, the inventors cultured isolated intestinal crypts obtained from healthy subjects in high glucose with/without serum obtained from long-standing T1D individuals in vitro for 8 days (FIG. 2L, panels labeled L1-L4; FIG. 2M). High glucose partially prevented the generation of fully mature mini-guts and synergized with serum of long-standing T1D individuals in altering CoSC self-renewal properties, such that mini-guts appeared collapsed (FIG. 2L, panels labeled L2-L4). Analysis of gene expression also revealed changes in the CoSC signature (FIG. 2N), thus suggesting that hyperglycemia and circulating factors act together to alter CoSC regenerative properties in long-standing T1D.

Figure 3A:
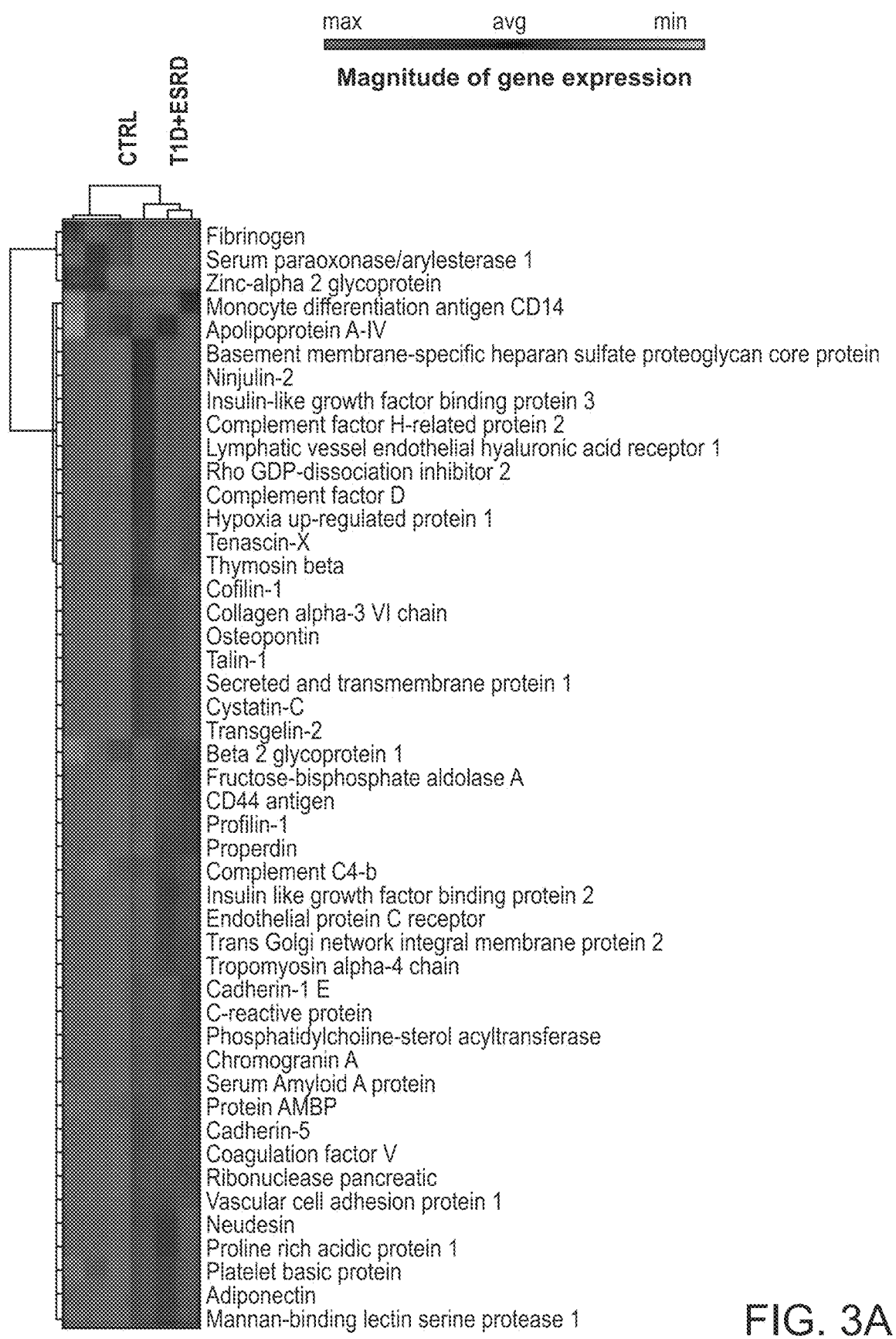
Figure 3B:
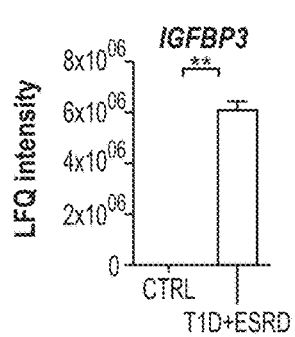
Figure 3C:
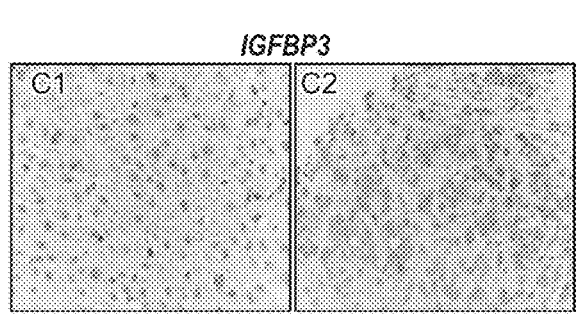
Figure 3D:
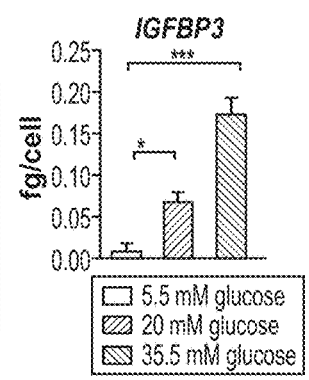
Figure 8K:
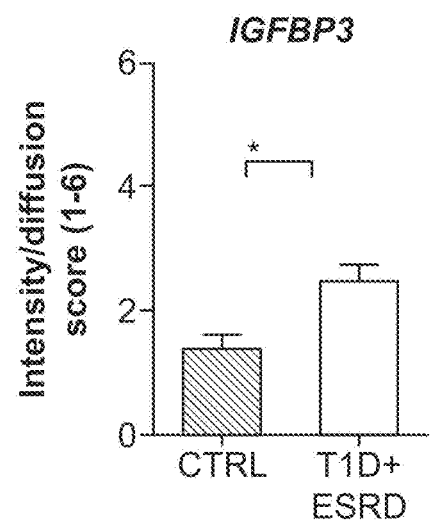
FIG. 8K is a bar graph representing the calculated combined score of IGFBP3 intensity/diffusion (0-6) upon immunohistochemical evaluation in liver samples obtained from healthy subjects and long-standing T1D individuals. N=3 subjects per group were evaluated.
Figure 8L:
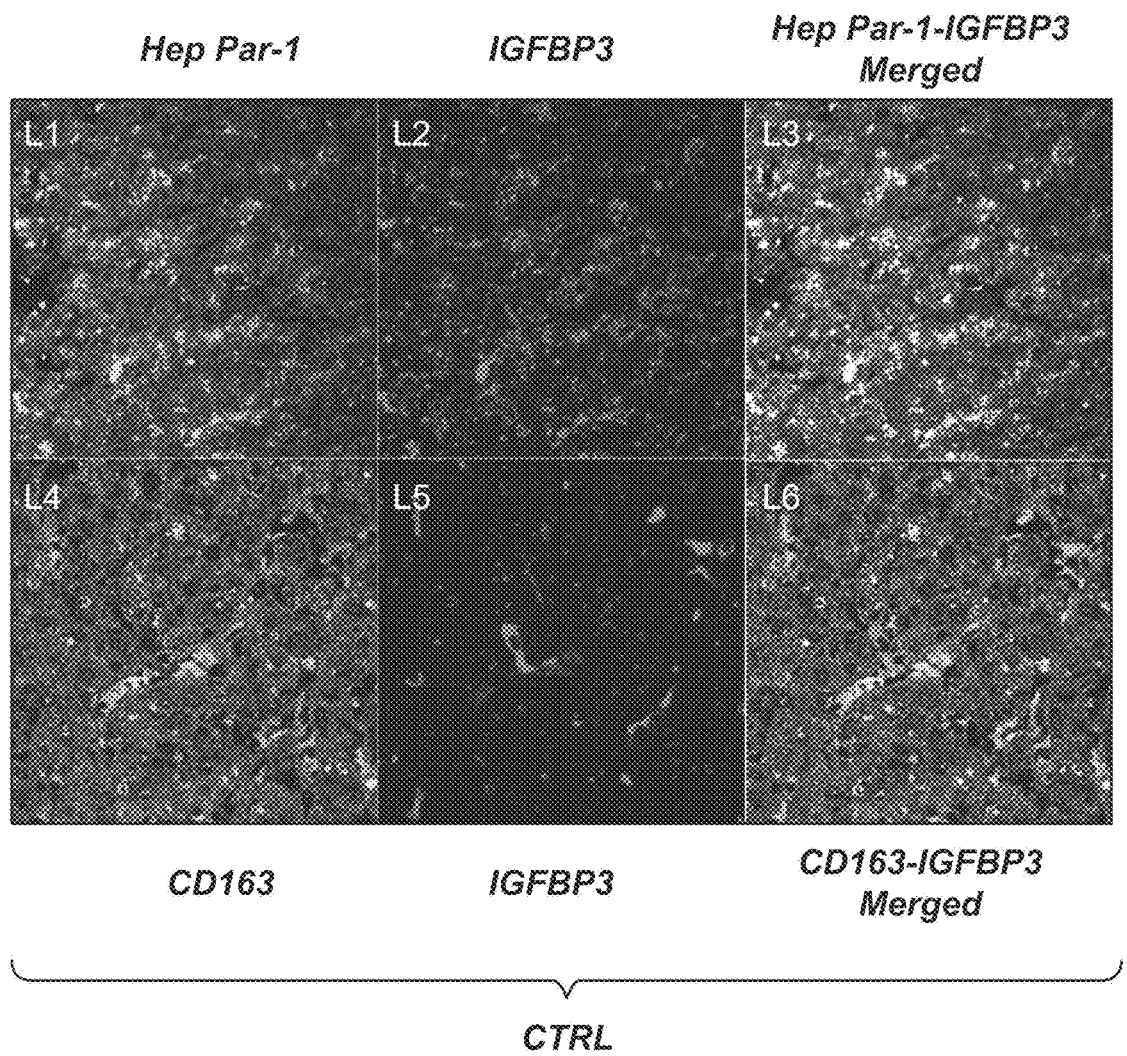
FIG. 8L shows representative images (63× magnification) of IGFBP3 expression in the liver. Immunofluorescence confirmed the colocalization of Hep Par-1$^+$ cells and IGFBP3 expression (panels labeled L1-L3), while no colocalization was observed between IGFBP3 and CD163$^+$ cells (panels labeled L4-L6).

Serum Unbiased Proteomic Profiling Revealed Increased Levels of IGFBP3 in Long-Standing T1D In order to identify potential circulating factors that may serve as enterotrophic hormones and may have a role in regulating the CoSCs, the inventors compared the serum proteome of healthy subjects with T1D+ESRD individuals using an unbiased proteomic array. A clear proteomic profile was evident in T1D+ESRD individuals as compared to healthy subjects, with more than 50% of the detected proteins segregating in either one group or the other (FIG. 3A). Some proteins were associated with diabetes, and some were growth factors or stem cell-related proteins or were potentially involved in intestinal functions (FIG. 3A). In particular, the levels of IGF-I binding proteins (IGFBP2 and 3) were detectable in long-standing T1D individuals as compared to healthy subjects, with IGFBP3 almost 5-fold increased (FIG. 3B), while IGFBP 1, 4, 5 and 6 remained almost undetectable. Interestingly, in the liver of individuals with long-standing T1D, hepatocytes, but not Kuppfer cells, showed a higher IGFBP3 immunohistochemical expression as compared to healthy subjects (FIG. 3C, panels labeled C1-C2; FIG. 8K; FIG. 8L, panels labeled L1-L6), suggesting an increase in IGFBP3 hepatic synthesis and release. The effect of high glucose on IGFBP3 hepatic release was confirmed by the detection of increased IGFBP3 levels in the supernatant of human immortalized hepatocytes exposed to high glucose (FIG. 3D). Finally, serum levels of free IGF-I appeared significantly reduced in long-standing T1D as compared to healthy subjects (FIG. 3E), indicating that circulating IGF-I and IGFBP3 levels are altered in long-standing T1D.

Peripheral IGFBP3 and IGF-I Control CoSCs

Figures 3E, 3F:
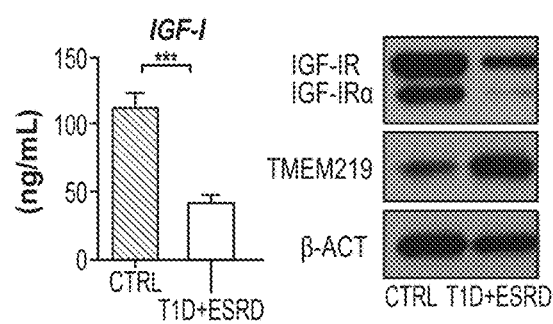
Figure 3G:
Figure 3H:
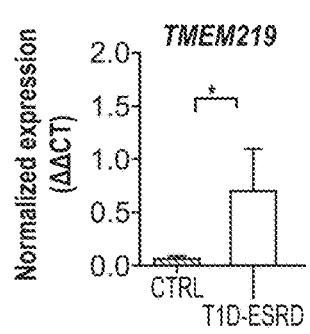
Figure 3I:
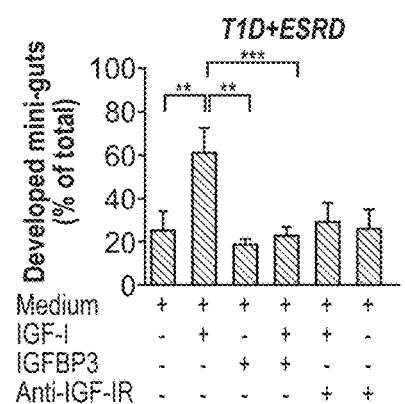
Figure 8M:
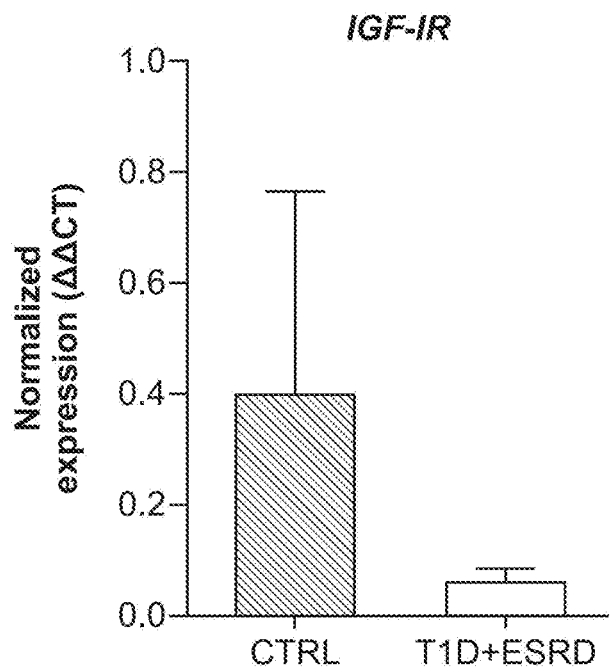
FIG. 8M is a bar graph depicting normalized mRNA expression of the IGF-I receptor (IGF-IR) measured by quantitative RT-PCR on isolated intestinal crypts. All samples were run in triplicate and normalized to the housekeeping gene ACTB using the ΔΔCt method.
Figure 8N:
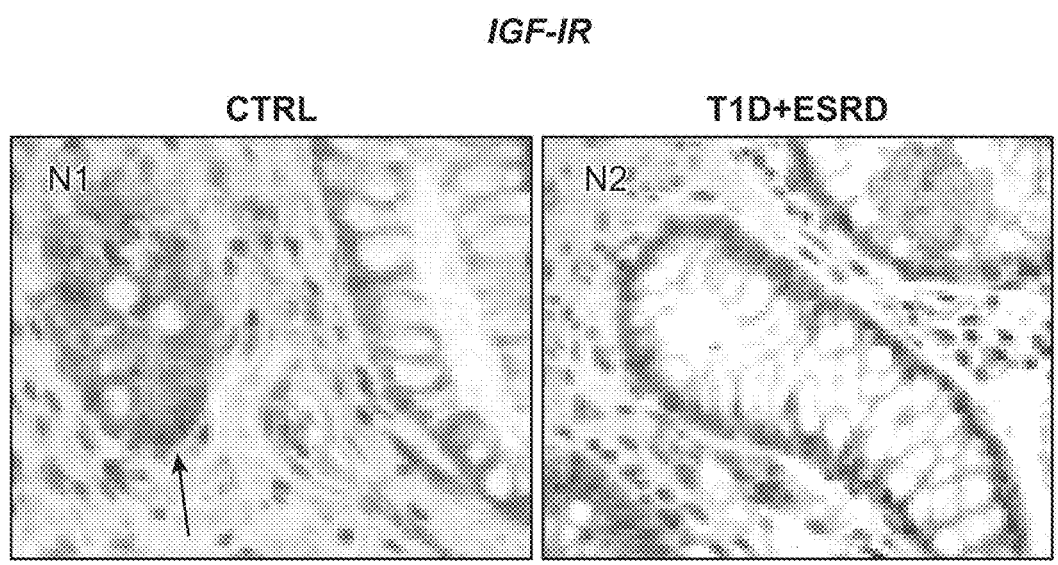

To further elucidate the role of circulating IGF-I and IGFBP3 in the regulation of the CoSCs and of intestinal epithelial proliferation, the inventors demonstrated the expression of IGF-IR and of IGFBP3 receptor (TMEM219) on isolated crypts (FIGS. 3F, 3H; FIG. 8M; FIG. 8N, panels labeled N1-N2) using RT-PCR and WB (FIGS. 3F, 3H; FIG. 8M), and confirmed the expression of IGF-IR on CoSCs with immunostaining (FIG. 8N, panels labeled N1-N2), and of TMEM219 with in situ hybridization (FIG. 3G, panels labeled G1-G2). In order to mechanistically confirm the role of IGF-I and IGFBP3 on CoSC, the inventors tested the effect of several molecules, identified by proteomic profiling, in their in vitro mini-gut assay. Inventors' strategy to select potential targets is reported in Supplemental Information. The severely altered mini-guts generated from intestinal samples obtained from T1D+ESRD individuals were rescued by the addition of recombinant human IGF-I (IGF-I) to the culture medium (FIG. 3I), while the addition of recombinant human IGFBP3 (IGFBP3) resulted in the abrogation of the positive effect observed with IGF-I, with a decreased development of mini-guts and increased formation of collapsed and distorted organoids (FIG. 3I). Because IGFBP3 has been recently shown to act independently of IGF-I (Williams et al., 2007) via the IGFBP3 receptor (TMEM219) (Baxter, 2013), it was necessary to clarify whether IGFBP3 exerts its effects on CoSCs by binding IGF-I or by directly targeting TMEM219 on CoSCs. The inventors first confirmed that IGFBP3 has a direct pro apoptotic effect on CoSCs by demonstrating increased Caspase 8 and 9 expression in mini-guts obtained from healthy subjects and long-standing T1D individuals and cultured with IGFBP3 (FIG. 3J, FIGS. 9A-9B), while the addition of a Pan-Caspase inhibitor (Z-VAD-FMK) or the addition of both selective inhibitors of caspases 8 and 9, but not that of other caspase cascade inhibitors (Caspase 3 inhibitor) abrogated the IGFBP3 effect (FIG. 3K). The inventors then demonstrated that the addition of IGF-I did not rescue the development of mini-guts obtained from healthy subjects and exposed to IGFBP3 (FIG. 3L), confirming that IGFBP3 may act through both a direct and indirect IGF-I mechanism. Interestingly, high glucose alone was unable to completely disrupt mini-gut growth, and anti-IGF-IR did not worsen growth and morphology of mini-guts formed from healthy subjects (FIG. 3L). The addition of IGF-I to mini-guts generated from healthy subjects, but cultured with high glucose and serum from long-standing T1D individuals, rescued mini-gut morphology, while IGFBP3 abolished the positive effect of IGF-I when added to the mini-gut culture (FIG. 3L). Interestingly, the use of healthy subjects "CTRL" serum in culturing crypts obtained from long-standing T1D nearly restored mini-guts development/morphology, indicating that circulating factors, and in particular IGF-I/IGFBP3 dyad, control CoSCs (FIGS. 9C-9D). The inventors then genetically modulated TMEM219 expression by using siRNA in vitro in mini-guts obtained from healthy subjects. Knockdown of TMEM219 in mini-guts preserved their ability to grow and self-renew, despite the addition of IGFBP3 and high glucose with long-standing T1D serum (FIG. 3M). Concomitant blockade of TMEM219 by SiRNA and IGF-IR by blocking antibody did not result in any additional beneficial effect on mini-guts development despite using serum from healthy subjects or from long-standing T1D (FIG. 9E).

Other circulating proteins, which appeared altered in serum proteome of long-standing T1D individuals, were tested in the in vitro mini-gut assay and did not show any significant effect on mini-guts growth (FIGS. 9F-9G). C-peptide and insulin, whose levels are commonly altered in T1D and which may interfere with IGF-I/IGFBP3 dyad by binding IGF-IR (FIG. 9H), were tested as well and did not show any effect.

Figure 4A:
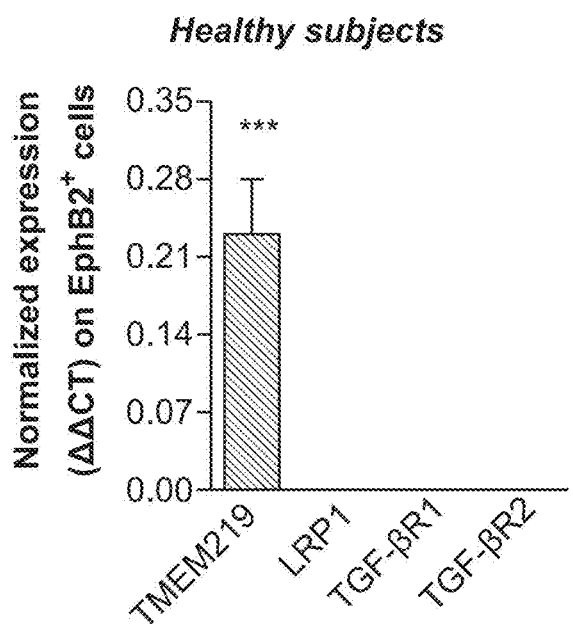
FIGS. 4A-4Q. Effects of the peripheral IGF-I/IGFBP3 dyad on single-cell derived in vitro mini-guts and on caspase cascade. Manipulating the peripheral IGF-I/IGFBP3 dyad alters the progression of diabetic enteropathy in a preclinical model of diabetic enteropathy, while the treatment of long-standing T1D with simultaneous pancreas-kidney transplantation (SPK) ameliorates intestinal symptoms, motility and morphology.
Figure 4B:
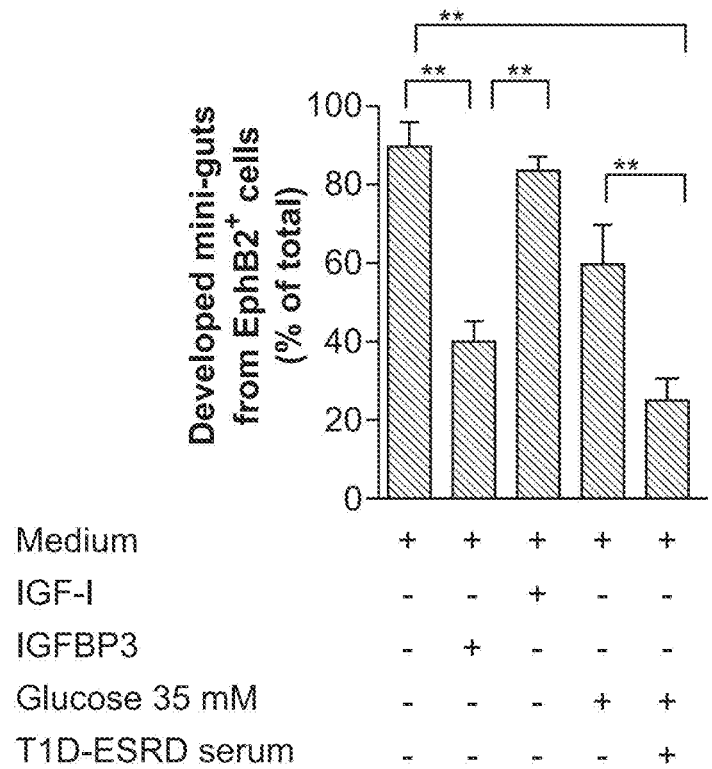
FIG. 4B is a bar graph showing % of developed single cell-derived mini-guts (of the total) obtained from EphB2$^+$ cells sorted from freshly isolated crypts of healthy subjects and cultured in different conditions (normal glucose+normal serum, high glucose+normal serum, T1D+ESRD serum+ normal glucose, T1D+ESRD serum+high glucose) and showing the effect of IGF-I and IGFBP3. The p values are relative to baseline condition.

To further confirm that IGF-I/IGFBP3 dyad targets effectively CoSCs and not only crypts, the inventors tested its effect on single cell-derived mini-guts. The inventors flow sorted EphB2+ cells from isolated crypts and established that TMEM219 was highly expressed on their surface (FIG. 4A). The inventors then cultured EphB2+ cells in the in vitro single cell-derived mini-gut assay and confirmed that high glucose and long-standing T1D serum exposure as well as addition of IGFBP3 significantly abrogate single cell-derived mini-guts growth, thus recapitulating the main features reported in their previous observations on crypt-derived mini-guts (FIG. 4B; FIG. 10A, panels labeled A1-A3).

Moreover, expression of Caspase 8 and 9 was up regulated in IGFBP3-treated mini-guts and in those exposed to high glucose and long-standing T1D serum, while Ki67, marker of proliferation, was significantly under expressed (FIGS. 10B-10D).

Effect of the IGF-I/IGFBP3 Dyad on Previously Known Pathways that Control CoSCs

Figure 10E:
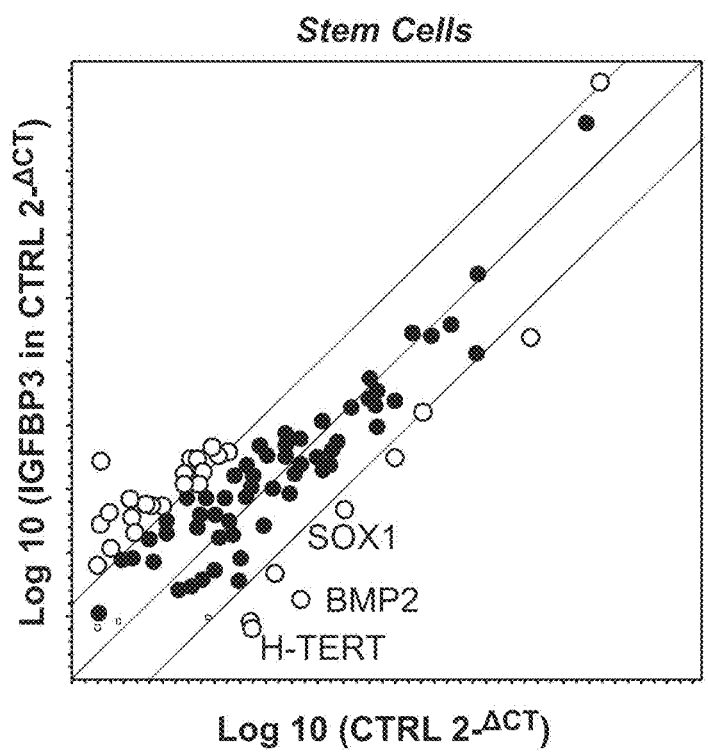
Figure 10F:
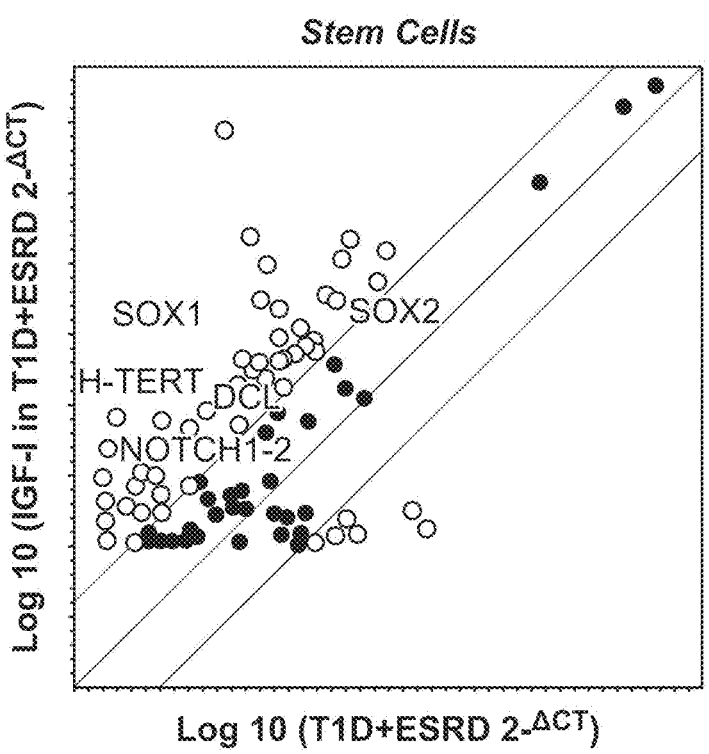

In order to clarify the effects of IGF-I/IGFBP3 dyad on pathways previously known to be involved in CoSC niche function (i.e. Wnt/Notch/BMP), the inventors obtained from their stem cell transcriptome profile the expression of niche specific gene transcripts. IGF-I restores significantly the expression of some factors associated with Wnt/Notch signaling pathways on mini-guts obtained from crypts of T1D+ESRD (FIG. 10E, Table III), while IGFBP3 poorly affects Wnt/Notch/BMP gene expression in mini-guts obtained from crypts of healthy subjects or from those of T1D+ESRD (FIG. 10F, Table III).

TABLE III

List of up and down-regulated stem cell target genes identified by transcriptomic profiling in colonic crypts obtained from CTRL and from T1D + ESRD and cultured with/without IGFBP3 and IGF-I (at least $p < 0.05$).

|  | Down-regulated genes | Up-regulated genes |
| --- | --- | --- |
| CTRL + IGF-I vs. CTRL | CD44, CDH1, COL9A1 | ACAN, COL2A1, DLL1, FGF2, FGF3, GDF3, GJA1, IGF-I, ISL1, MME, MSX1, NCAM1, NOTCH2, PDX1, SOX1, SOX2, h-TERT |
| CTRL + IGFBP3 vs. CTRL | CD8B, COL9A1, RB1, SOX1, h-TERT | ASCL2, COL2A1, DHH, DLL1, DTX1, DVL1, FGF3, FGF4, FOXA2, FRAT1, GDF2, HSPA9, IGF1, KAT2A, MSX1, MYC, NEUROG2, S100B, WNT1 |
| T1D + ESRD + IGF-I vs. T1D + ESRD | ACTC1, CD3D, CD4, COL9A1, DTX1, FGFR1 | ABCG2, ADAR, BMP1, BMP2, BTRC, CDC42, CTNNA1, CXCL12, DLL1, DTX2, GDF3, HDAC2, ISL1, JAG1, NOTCH1, NOTCH2, NUMB, PARD6A, PDX1, RB1, SIGMAR1, h-TERT |
| T1D + ESRD + IGFBP3 vs. T1D + ESRD | ABCG2, ALDH1A1, ALPI, CD3D, CD4, CD44, CD8A, CDC42, FGF2, FGFR1, JAG1, SIGMAR1, SOX1, TUBB3 | ASCL2, KAT2A, MYC, NCAM1, NEUROG2, SOX2 |

Abbreviations: IGF-I, insulin-like growth factor 1; IGFBP3, insulin-like growth factor binding protein 3, CTRL, healthy subjects, T1D, type 1 diabetes, ESRD, end-stage renal disease.

This confirms that IGF-I preserves the expression of some genes involved in Wnt/Notch/BMP signaling, but also that IGFBP3 acts independently on CoSCs, without major alterations in the expression of key-target genes of the other previously known pathways.

Effect of IGF/IGFBP3 Dyad on Apoptotic Pathways in CoSCs

Figure 4C:
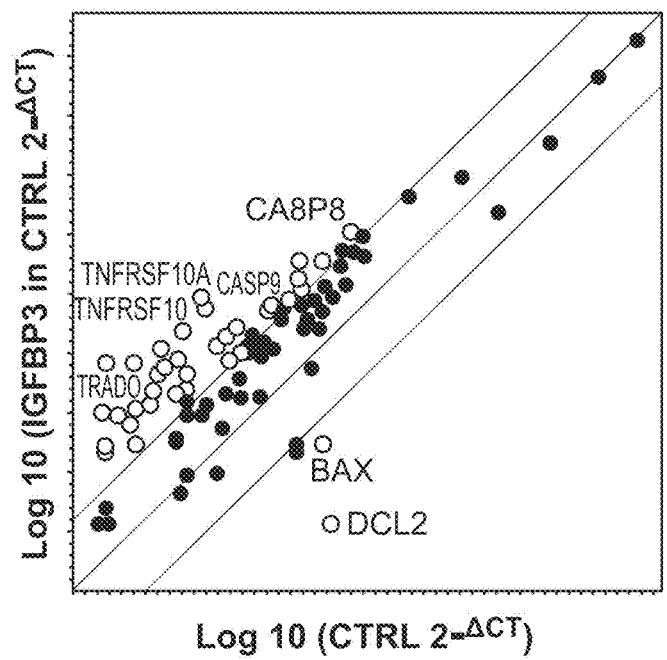
FIGS. 4C-4D are scatter plots representing the apoptosis transcriptome profiling examined in freshly isolated intestinal crypts of healthy subjects (CTRL) and long-standing T1D individuals (T1D+ESRD) cultured with/without IGFBP3 and IGF-I. Experiments were run in triplicate.
Figure 4D:
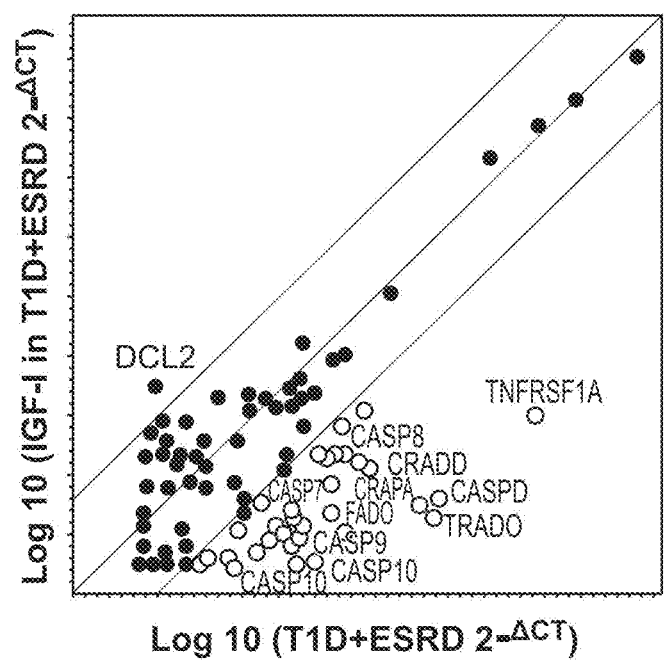
Figure 10G:
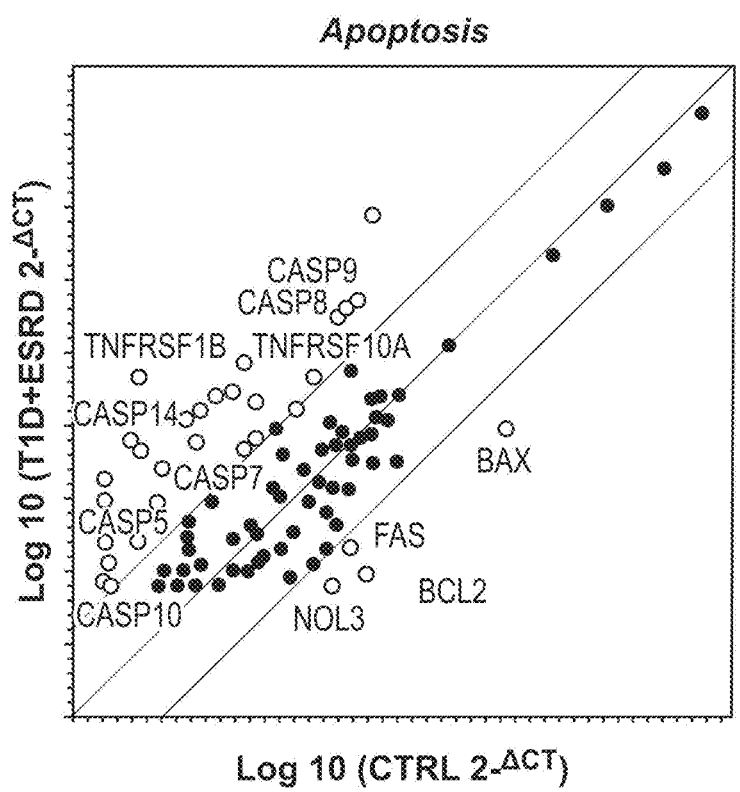
Figure 10H:
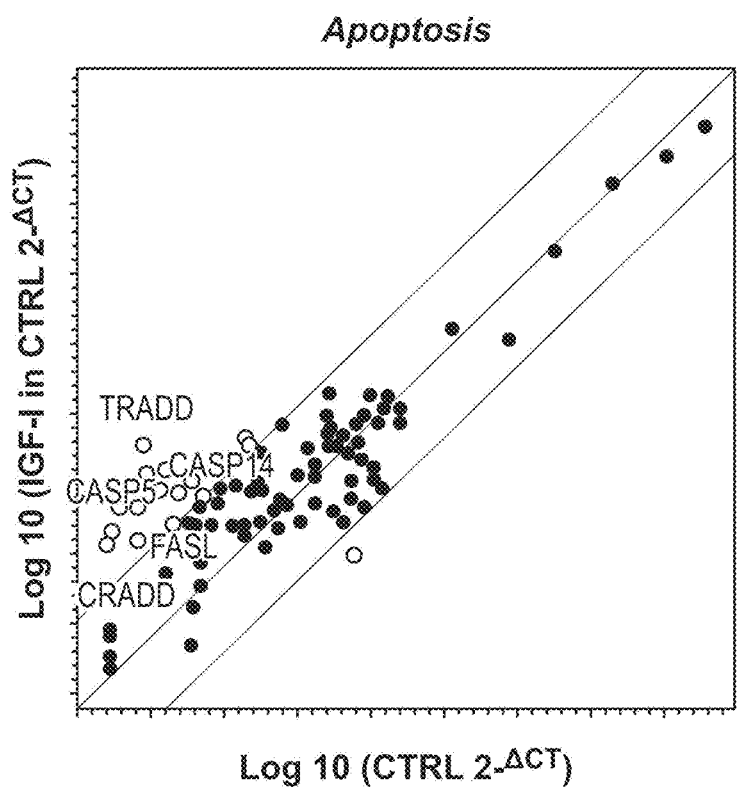
Figures 10I, 10J:
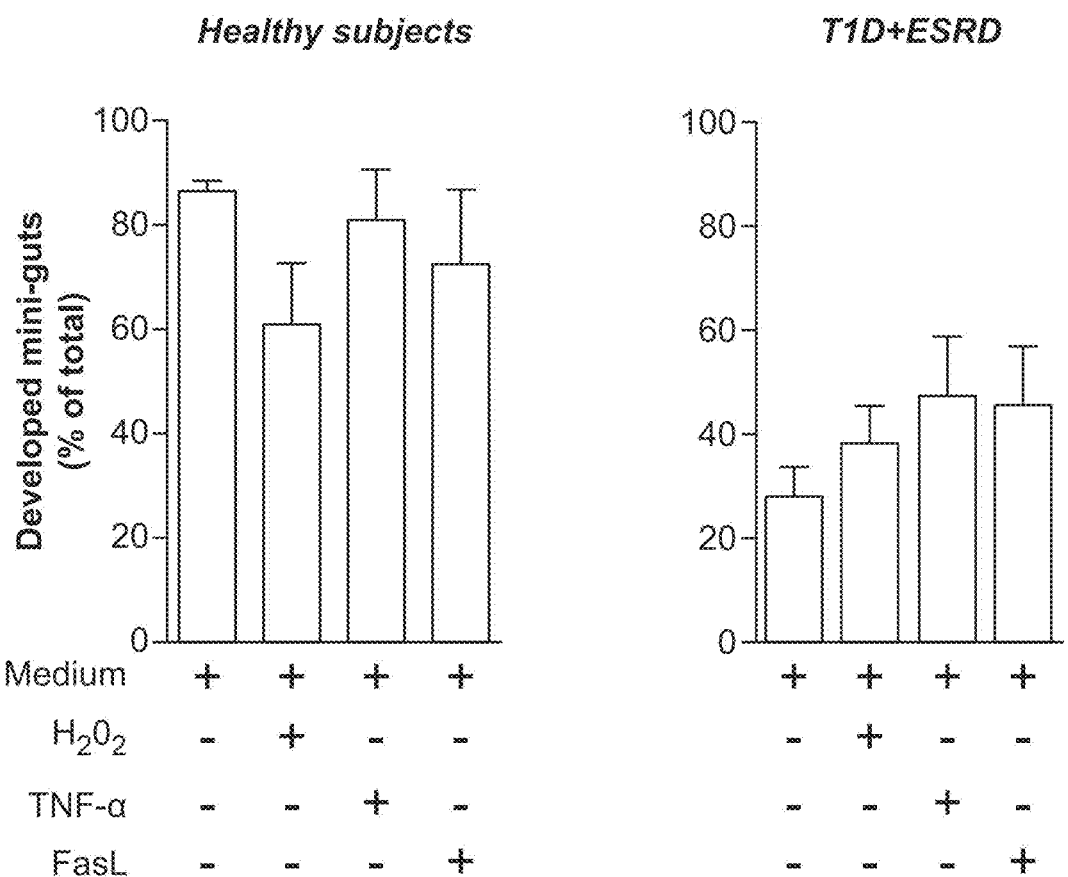

An extensive transcriptome analysis performed to clarify the IGFBP3 caspase-mediated effect on mini-guts, (FIGS. 4C-4D; FIGS. 10G-10H; Table IV), showed that addition of IGFBP3 to mini-guts grown from healthy subjects crypts, was associated with a significant up regulation of caspase-cascade activators (Caspases 8 and 9) and proapoptotic genes, while the anti-apoptotic gene Bcl2 was down regulated (FIG. 4C).

TABLE IV

List of up and down-regulated pro/anti-apoptotic target genes identified by transcriptomic profiling in CTRL vs. T1D + ESRD freshly isolated colonic crypts and in those cultured with IGFBP3 and IGF-I (at least $p < 0.05$).

|  | Down-regulated genes | Up-regulated genes |
| --- | --- | --- |
| T1D + ESRD vs. CTRL | BCL2, NOL3, FAS | CASP1, CASP10, CASP14, CASP5, CASP6, CASP7, CASP8, CASP9, CD27, CRADD, FADD, FASLG, HRK, TNFRSF10A, TNFRSF10B, TNFRSF11B, TNFRSF1A, TNFRSF1B, TNFRSF25, TNFRSF9, TNFSF8, TRADD, TRAF3 |
| CTRL + IGF-I vs. CTRL | BNIPL3 | CASP14, CASP5, CD27, CRADD, FASLG, TNFRSF25, TNFSF8, TRADD |
| CTRL + IGFBP3 vs. CTRL | BAX, BCL2 | CASP5, CASP8, CASP9, FAS, TNFRSF1B, TNFSF8, TRADD, TRAF3 |

TABLE IV-continued

List of up and down-regulated pro/anti-apoptotic target genes identified by transcriptomic profiling in CTRL vs. T1D + ESRD freshly isolated colonic crypts and in those cultured with IGFBP3 and IGF-I (at least $p < 0.05$).

|  | Down-regulated genes | Up-regulated genes |
| --- | --- | --- |
| T1D + ESRD + IGF-I vs. T1D + ESRD | CASP1, CASP10, CASP5, CASP6, CASP7, CASP8, CASP9, CRADD, FADD, TNFRSF11B, TNFRSF9, TNFSF8, TRADD, TRAF3 | BCL2 |
| T1D + ESRD + IGFBP3 vs. T1D + ESRD | BAX, BCL2, NOL3, TNFRSF1B | CASP9, CD27 |

Abbreviations: IGF-I, insulin-like growth factor 1; IGFBP3, insulin-like growth factor binding protein 3, CTRL, healthy subjects, T1D, type 1 diabetes, ESRD, end-stage renal disease.

Interestingly, anti-apoptotic genes (Bcl2, Fas, Nol3) were significantly underexpressed in mini-guts grown from T1D+ ESRD crypts as well, as compared to healthy subjects, while the majority of caspases related genes (Caspase 1, 5, 7, 8, 9, 14) were over expressed (FIG. 10G). Moreover, the expression of genes involved in other pro apoptotic pathways was either not altered (i.e. Fas Ligand, FADD, TNF) or inhibited (TRADD) in T1D+ESRD mini-guts. The opposite effect was observed by adding IGF-I (FIG. 4D, FIG. 10H). The absence of alterations in the expression of oxidative stress target genes (Table V) and of any effect of oxidative stress factors (FIGS. 10I-10J), confirmed the main apoptotic-related caspase-mediated IGFBP3 mechanism whereby circulating IGFBP3 directly controls CoSCs (FIG. 4E).

Figure 4H:
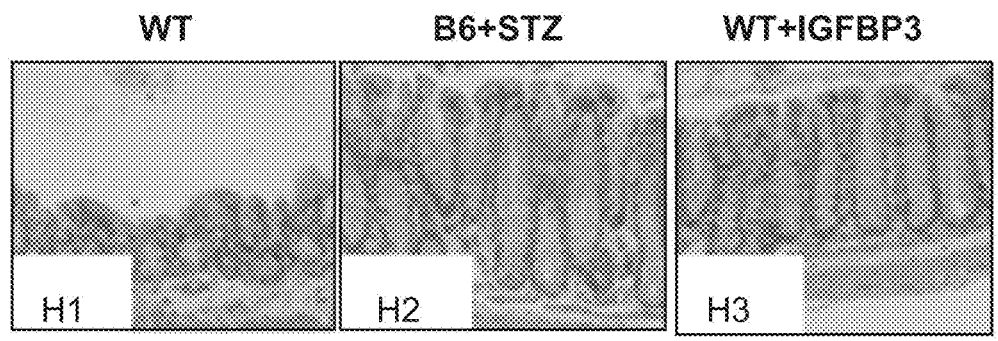
Figures 4I, 4J:
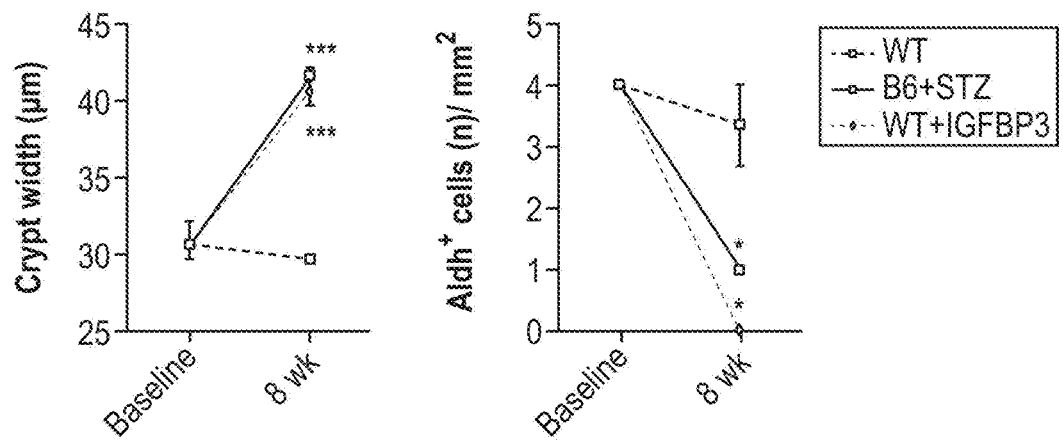
Figure 4K:
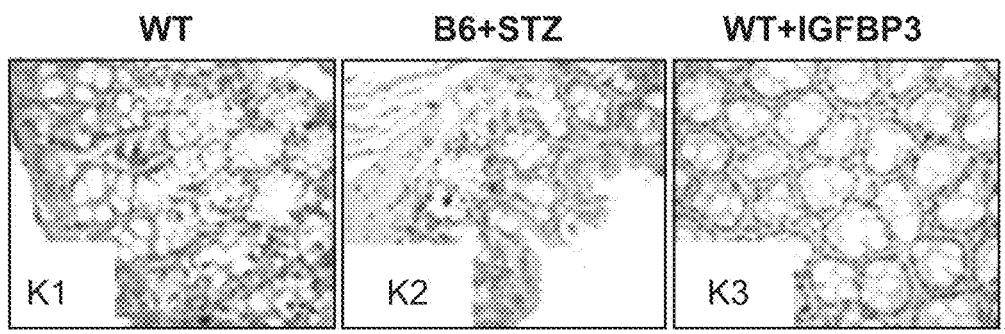
FIG. 4K are representative images of Aldh$^+$ cells on immunostained sections of intestinal lower tract harvested from STZ-treated B6 mice developing diabetic enteropathy, WT, and naïve B6 treated with IGFBP3 (WT+IGFBP3). Histology magnification, 400×.
Figure 11A:
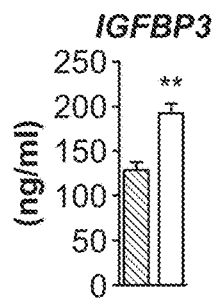
FIGS. 11A-11N. Manipulating IGF-I/IGFBP3 dyad in preclinical models of diabetic enteropathy.
Figure 11B:
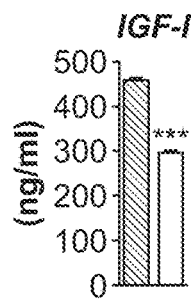
FIG. 11B is a bar graph representing IGF-I circulating levels measured in naïve B6 mice (WT) and STZ-treated B6 mice (B6+STZ).
Figure 11C:
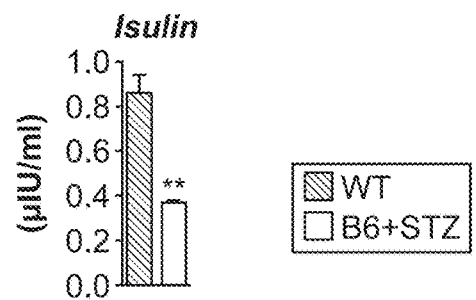
FIG. 11C is a bar graph representing insulin serum levels measured in naïve B6 mice (WT) and STZ-treated B6 mice (B6+STZ).
Figure 11D:
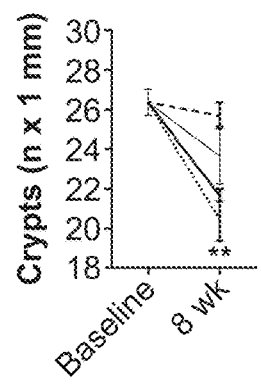
FIGS. 11D, 11E, 11F are line graphs reporting the number of crypts (FIG. 11D), depth of crypts (FIG. 11E) and width of crypts (FIG. 11F) assessed on intestinal lower tract sections harvested at baseline and after 8 weeks from STZ-treated B6 mice developing diabetic enteropathy (B6+STZ), naïve B6 (WT), and STZ-B6 mice treated with IGFBP3 (B6+STZ+IGFBP-3) or with IGF-I (B6+STZ+IGF-I). WT: wild type, STZ: streptozoticin-treated. N=3 mice per group were evaluated.
Figure 11E:
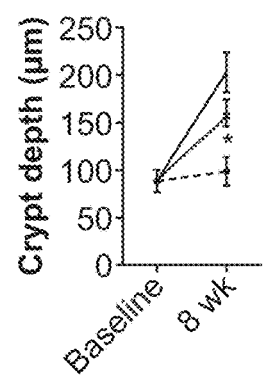
Figure 11F:
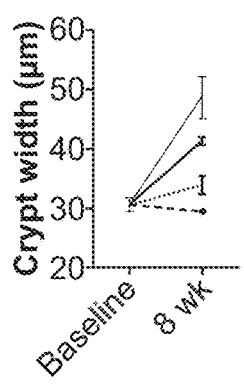
Figure 11G:
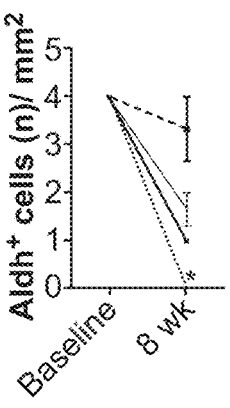
FIG. 11G is a line graph representing the number of Aldh$^+$ cells/mm$^2$ in immunostained sections of STZ-treated B6 mice developing diabetic enteropathy, WT, and STZ-B6 mice treated with IGFBP3 (B6+STZ+IGFBP3) or with IGF-I (B6+STZ+IGF-I).
Figure 11H:
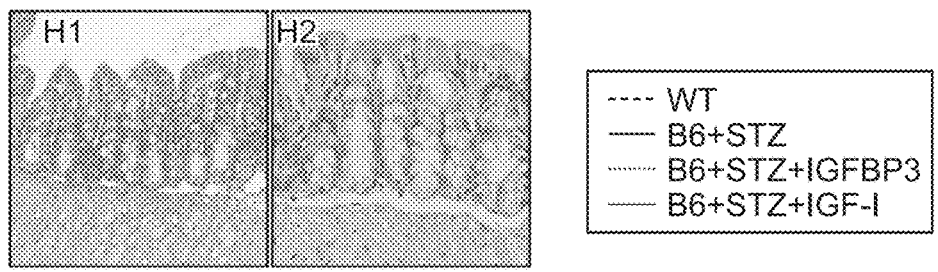
FIG. 11H provides representative images of intestinal crypts on H&E sections of STZ-B6 mice treated with IGFBP3 (B6+STZ+IGFBP3), (panel labeled H1) or with IGF-I (B6+STZ+IGF-I), (panel labeled H2). Histology magnification, 400×.
Figure 11I:
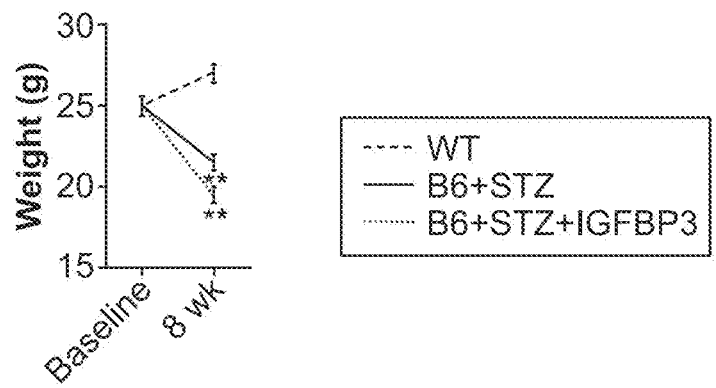
FIG. 11I is a line graph reporting the weight of STZ-treated B6 mice developing diabetic enteropathy (B6+STZ), naïve B6 (WT), STZ-treated B6 mice developing diabetic enteropathy treated with IGFBP3 (B6+STZ+IGFBP3). WT: wild type, STZ: streptozoticin-treated. N=3 mice per group were evaluated.
Figure 11J:
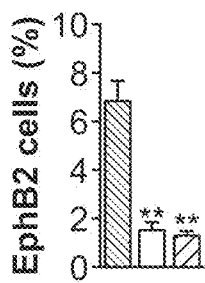
FIG. 11J is a bar graph representing results of flow cytometric analysis of EphB2+ cells in intestinal samples collected from naïve B6 mice, STZ-treated B6 mice and in STZ-B6 mice treated with IGFBP3 (B6+STZ+IGFBP3).
Figure 11K:
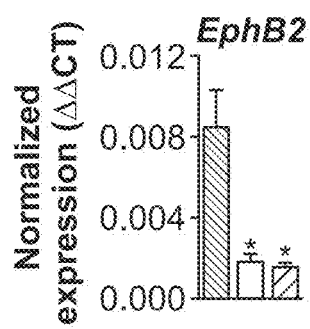
FIGS. 11K-11L are bar graphs representing normalized mRNA expression of EphB2 (FIG. 11K) and LGR5 (FIG. 11L) in intestinal samples collected from naïve B6 mice, STZ-treated B6 mice and in STZ-B6 mice treated with IGFBP3 (B6+STZ+IGFBP3).
Figure 11L:
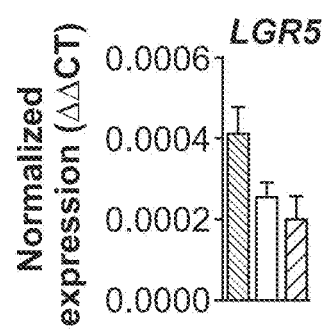
Figure 11M:
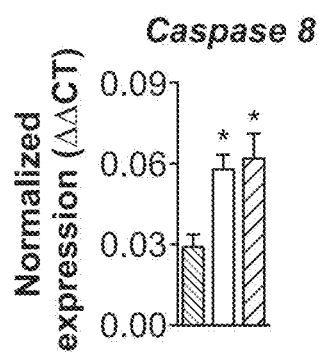
Figure 11N:
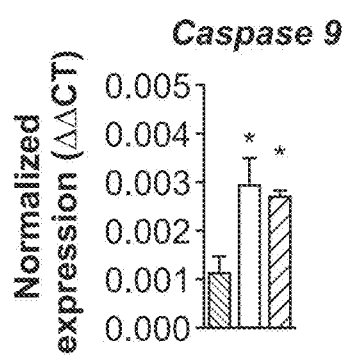

B6 (FIGS. 11A-11C). Intraperitoneal (i.p.) administration of IGFBP3 in naïve B6 mice resulted in a reduction in local crypt numbers (FIG. 4F; FIG. 4H, panel labeled H3), with the majority of crypts showing increased depth and width (FIG. 4G; FIG. 4H, panel labeled H3; FIG. 4I) and significant reduction in Aldh$^+$ cells as compared to untreated mice (FIG. 4J; FIG. 4K, panel labeled K3). Those features were aggravated by IGFBP3 administration to STZ-treated B6 mice (FIGS. 11D-11G; FIG. 11H, panels labeled H1-H2), with evidences of weight decrease (FIG. 11J), CoSCs loss (FIGS. 11J-11L) and up regulated expression of Caspase 8 and 9 (FIGS. 11M-11N). Administration of IGF-I i.p in

TABLE V

List of up and down-regulated oxidative stress target genes identified by transcriptomic profiling in CTRL vs. T1D + ESRD freshly isolated colonic crypts and in those cultured with IGFBP3 and IGF-I (at least $p < 0.05$).

|  | Down-regulated genes | Up-regulated genes |
| --- | --- | --- |
| T1D + ESRD vs. CTRL | DUOX1, PRDX4, STK25, GSS | CYBB, GPX5, KRT1, MT3, NOX4, OXR1, PTGS1, SFTPD |
| CTRL + IGF-I vs. CTRL | DUOX1, TXNRD | AOX1, FTH1, GPX7, GSS, KRT1, LPO, MPO, NCF1, NOS2, NOX4, OXR1, PTGS1, PTGS2, SCARA3, SFTPD, TPO, TTN |
| CTRL + IGFBP3 vs. CTRL | NCF1, SOD3 | AOX1, GPX5, GPX7, HSPA1A KRT1, MB, MPO, NOX5, OXR1, PTGS1, SFTPD, TPO, TTN, TXNRD2, UCP2 |
| T1D + ESRD + IGF-I vs. T1D + ESRD | DUOX1, EPHX2, MB, MT3, NCF1, OXR1, PTGS1, SOD3, SRXN1 | MPO, PRDX4, PRNP, STK25 |
| T1D + ESRD + IGFBP3 vs. T1D + ESRD | CYBB, DUOX1, EPHX2 GPX3, GSTP1, HSPA1A MGST3, NCF1, NQO1, PRDX6, RNF7, TXN | NOS2, STK25 |

Abbreviations: IGF-I, insulin-like growth factor 1; IGFBP3, insulin-like growth factor binding protein 3, CTRL, healthy subjects, T1D, type 1 diabetes, ESRD, end-stage renal disease.

Manipulation of the Circulating IGF-I/IGFBP3 Dyad Alters the Course of Diabetic Enteropathy in a Preclinical Model In order to further demonstrate the relevance of IGF-I/IGFBP3 circulating factors in vivo, the inventors tested the effects of IGF-I and IGFBP3 administration in a preclinical model of DE. After 8 weeks of chemically-induced diabetes (using streptozotocin [STZ]), C57BL/6 (B6) mice showed a reduced number of crypts in the colorectal tissue (FIG. 4F), which displayed increased depth and width in more than 70% of cases (FIG. 4G; FIG. 4H, panels labeled H1-H2; FIG. 4I) and a reduced number of Aldh$^+$ cells (FIG. 4J; FIG. 4K, panels labeled K1-K2). Interestingly, those mice showed increased serum levels of IGFBP3 and low levels of IGF-I, with lower murine insulin levels as compared to naïve STZ-treated B6 mice only partially improved mucosa morphology increased the number of normal crypts, which remained abnormal (FIG. 11D), and only partially restored the number of Aldh$^+$ cells (FIG. 11G; FIG. 11 H, panels labeled H1-H2).

Treatment of Long-Standing T1D with Simultaneous Pancreas-Kidney Transplantation (SPK) Reverts Clinical and Morphological Features of DE The gold standard treatment for long-standing T1D is SPK, which affords stable glycometabolic control, near-normalized risk factors and prolonged survival (Table VI) (Fiorina et al., 2004; Fiorina et al., 2005; Folli et al., 2010; Secchi et al., 1998; Smets et al., 1999).

TABLE VI

Restoration of both normoglycemia and normal renal function in SPK is associated with stable glucose/lipid metabolism and blood pressure control over time at up to 8 years of follow-up as compared to K + T1D (data are shown at 8 years of follow-up).

| Parameters | T1D + ESRD (n = 60) | SPK (n = 30) | K + T1D (n = 30) | P value |
|---|---|---|---|---|
| eGFR (ml/min/1.73 m$^2$) | <15 | 65.6 ± 20.2* | 61.8 ± 25.2§ | *, §<0.0001 |
| HbA1c (%) | 8.4 ± 1.5 | 5.4 ± 0.3* | 7.5 ± 1.4§ | *<0.0001; §<0.001 |
| EIR (UI) | 37.4 ± 2.3 | 0* | 26.0 ± 7.0§ | *<0.0001; §0.001 |
| TG (mg/dl) | 162.5 ± 92.7 | 90.4 ± 23.0* | 147.1 ± 98.0§ | *0.01; §0.04 |
| Chol (mg/dl) | 201.0 ± 45.7 | 185 ± 27.2 | 191.1 ± 41.1 | Ns |
| LDL (mg/dl) | 116.3 ± 40.3 | 119.5 ± 34.0 | 97.8 ± 2.1 | Ns |
| HDL (mg/dl) | 48.1 ± 14.4 | 51.4 ± 4.1 | 43.13 ± 5.7 | Ns |
| Systolic BP | 146.3 ± 18.7 | 133.1 ± 14.2* | 140.1 ± 15.7§ | 0.03; §0.04 |
| Diastolic BP | 83.7 ± 8.3 | 79.1 ± 9.2 | 78.3 ± 9.2 | Ns |

Abbreviations: T1D, type 1 diabetes; ESRD, end stage renal disease; SPK, simultaneous kidney-pancreas transplantation; K + T1D, kidney transplantation alone in type 1 diabetes; eGFR, estimated glomerular filtration rate; HbA1c, glycated hemoglobin; EIR, exogenous insulin requirement; TG, tryglycerides; Chol, total cholesterol; LDL, low density lipoprotein; HDL, high density lipoprotein; BP, blood pressure; UI, International Unit.

Figures 12A, 12B, 12C:
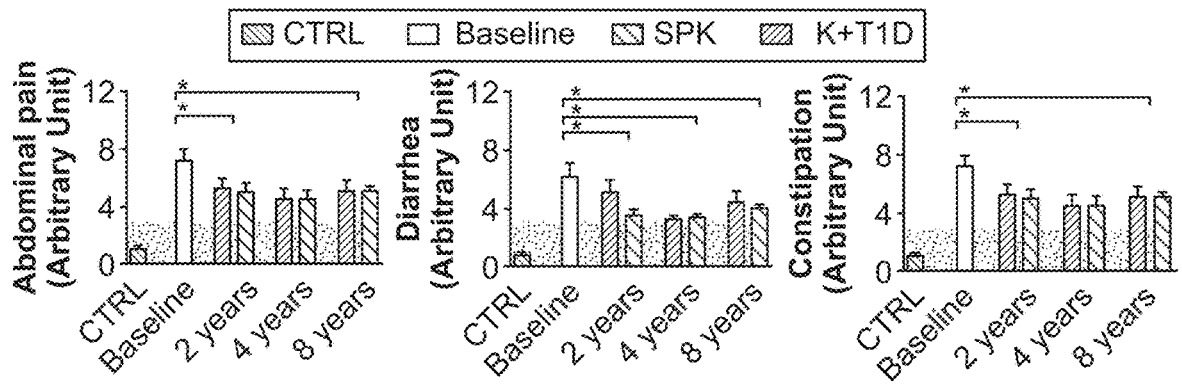
FIGS. 12A-12K. The treatment of long-standing T1D with SPK ameliorates diabetic enteropathy.

However, individuals with T1D+ESRD are also treated with kidney transplantation alone but remain diabetic (K+T1D) (Fiorina et al., 2001). A significant improvement in gastrointestinal symptoms was evident over time after SPK in inventors' cohort of transplanted individuals, while the K+T1D group did not report any benefit (FIGS. 12A-12C), suggesting that DE is reversible.

Figure 4L:
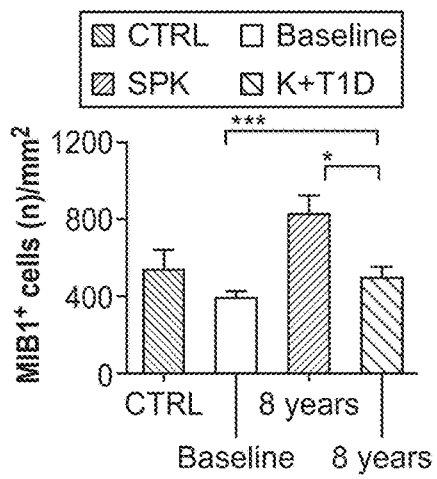
FIGS. 4L, 4N, 4P are bar graphs reporting the measurement of MIB1$^+$ and Aldh$^+$ cells, and EphB2$^+$ expression (intensity score 0-5) in the four groups of subjects (n=20 CTRL, n=30 SPK, n=K+T1D and n=60 T1D+ ESRD).
Figure 4M:
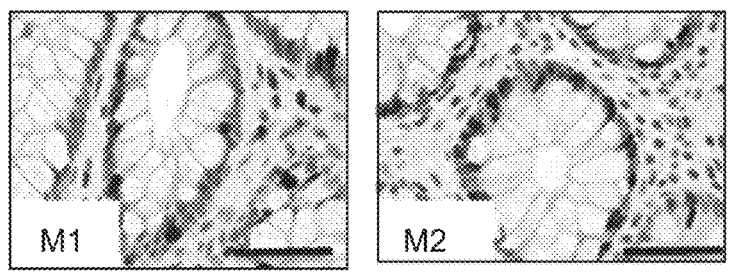
Figure 12D:
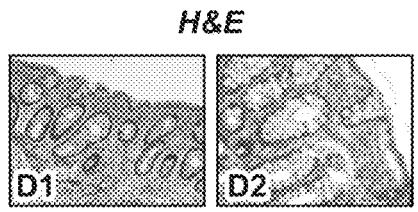
Figure 12E:
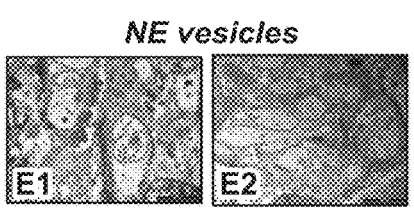
Figure 12F:
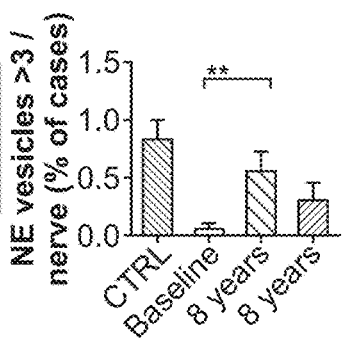
Figure 12G:
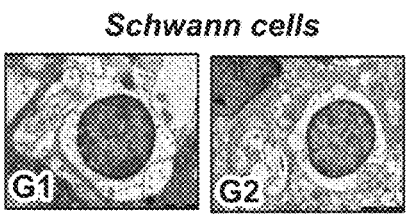
Figure 12H:
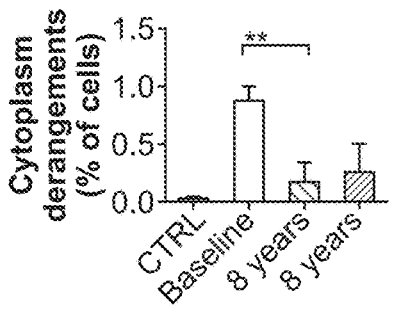
Figure 12I:
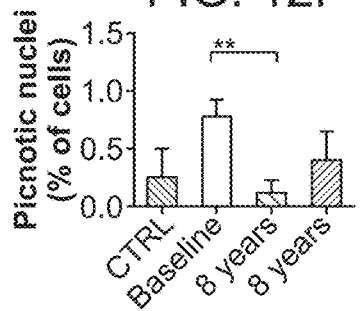
Figure 12J:
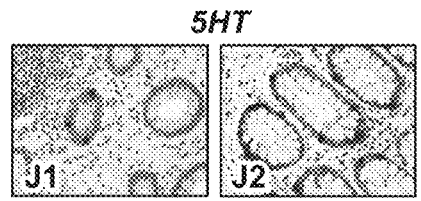
Figure 12K:
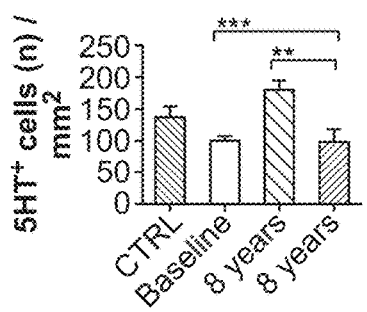

Treatment of Long-Standing T1D with SPK Re-Establishes Intestinal Mucosa Morphology and Local Self-Renewal Properties Analysis of intestinal mucosa samples showed a significant recovery in the structure of the epithelial compartment, with compensatory epithelial hyperplasia in the SPK group (FIG. 12D, panels labeled D1-D2). Recovery of normal crypt histology and number was evident in the SPK group when longstanding T1D was successfully treated while none of these features were evident in individuals who received kidney transplant only and remained diabetic (FIG. 12D, panels labeled D1-D2). Epithelial cell proliferation (MIB1$^+$ cells) increased after SPK over time as compared to baseline and to K+T1D at each timepoint (FIG. 4L; FIG. 4M, panels labeled M1-M2), with near-normalization of intestinal morphology, epithelial renewal and neural features (FIG. 12 E, panels labeled E1-E2; FIG. 12F; FIG. 12G, panels labeled G1-G2; FIGS. 12H-12I; FIG. 12 J, panels labeled J1-J2; FIG. 12K). This demonstrates that treatment of long-standing T1D with SPK promoted recovery of intestinal epithelial repair and of self-renewing properties.

Treatment of Long-Standing T1D Promotes Restoration of CoSCs

Figure 4N:
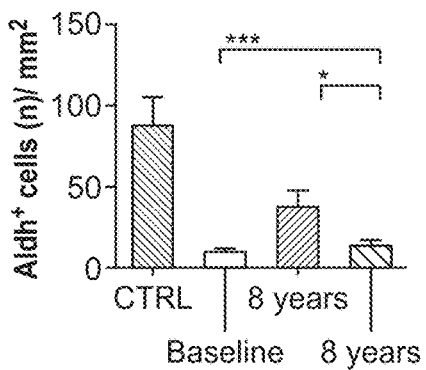
Figure 4O:
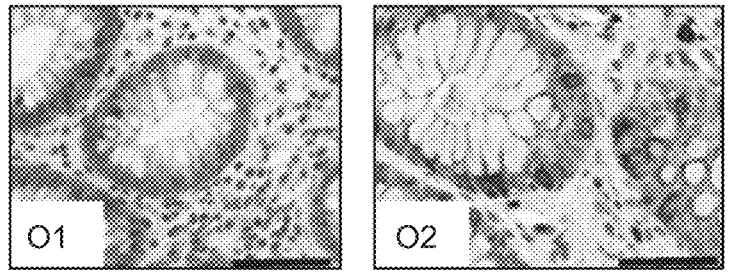
Figure 4P:
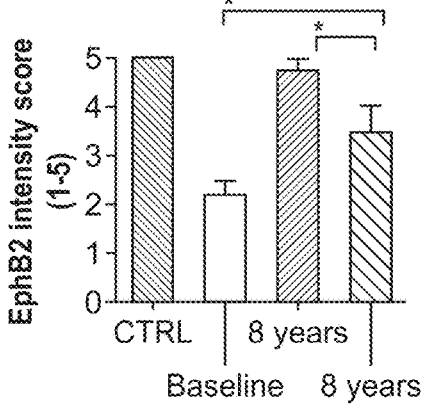
Figure 4Q:
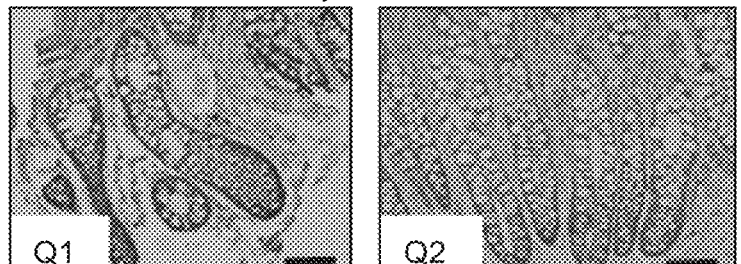
Figure 5G:
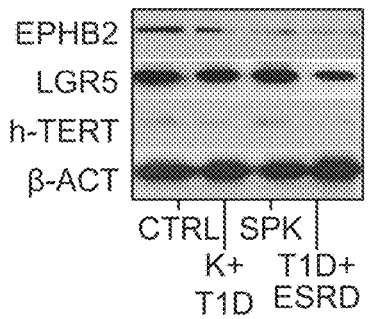
Figure 5H:
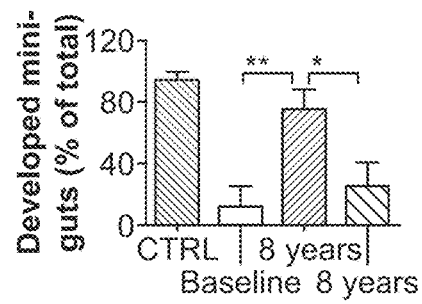
Figure 5I:
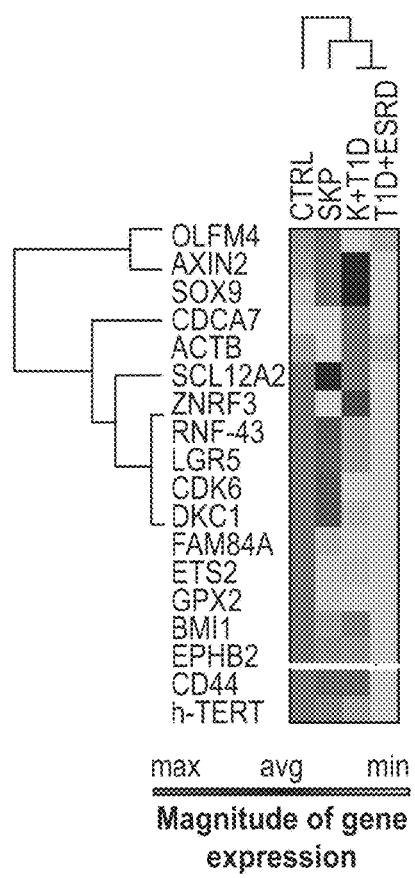
Figure 13A:
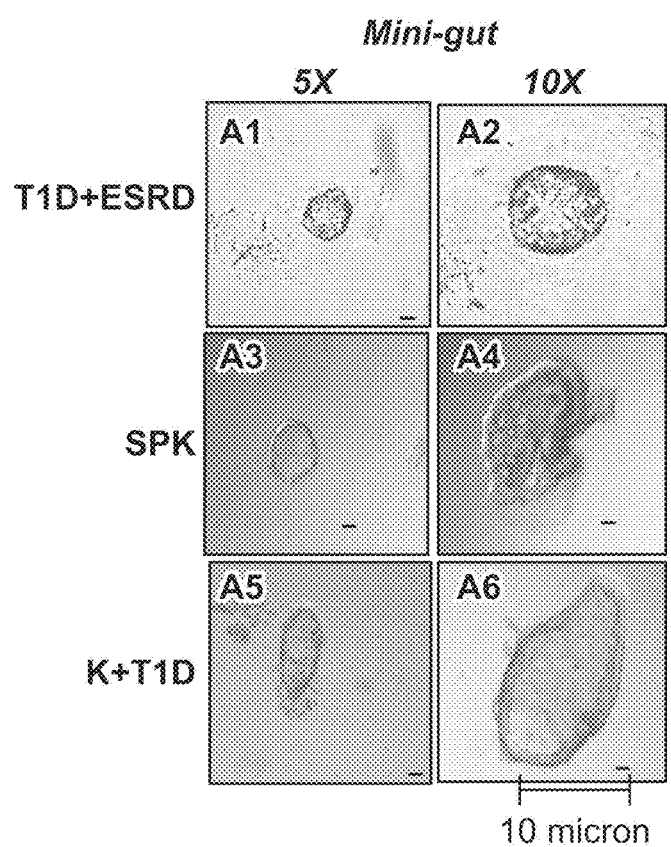
FIGS. 13A-13D. Analysis of colonic stem cells, IGF-IR and proteomic profile of circulating factors in diabetic enteropathy in SPK and K+T1D groups.
Figure 13B:
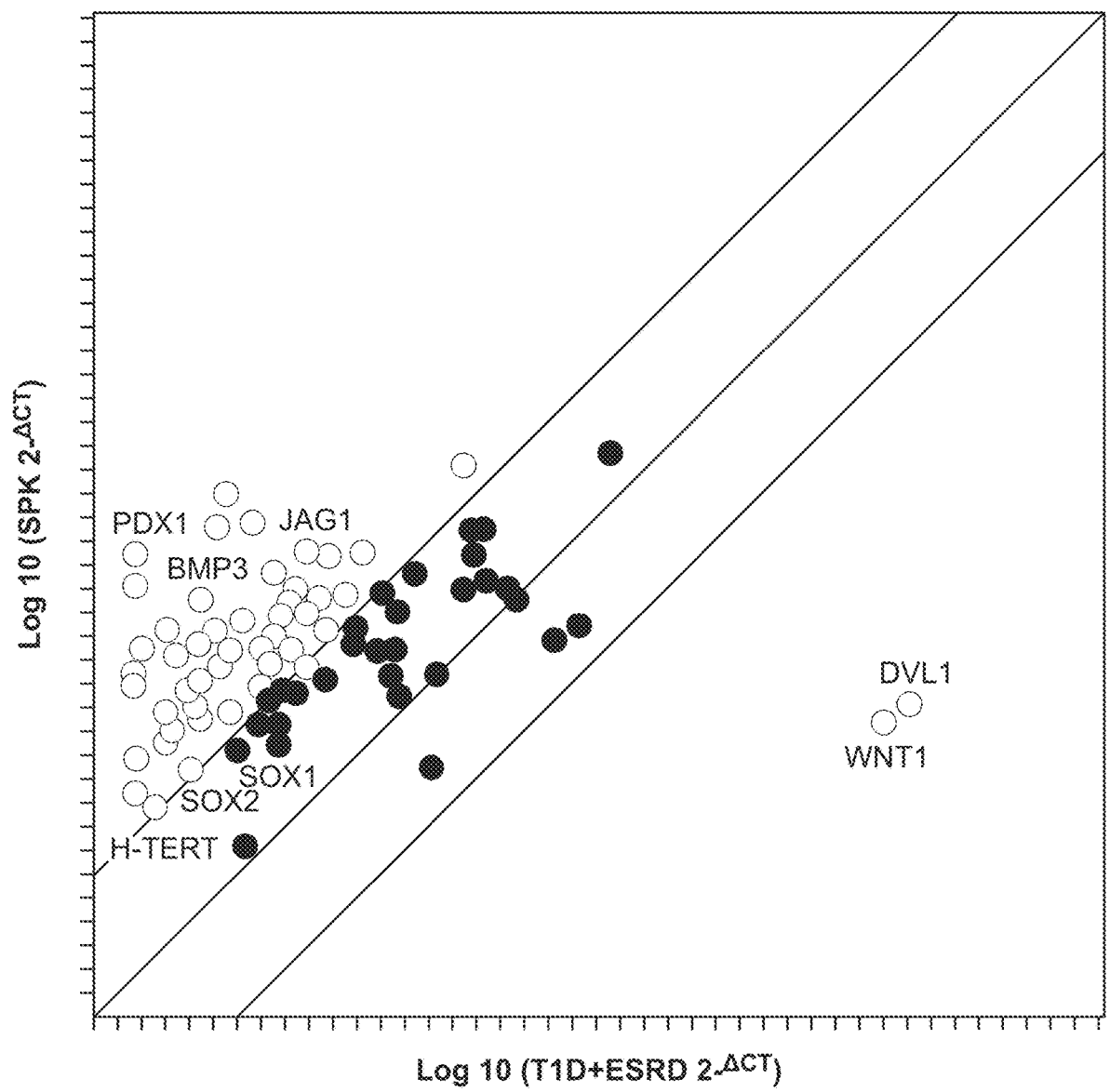

Treatment of long-standing TID with SPK is associated with an increase in Aldh$^+$ cells (FIG. 4N; FIG. 4O, panels labeled O1-O2) and EphB2$^+$ expression in the intestinal crypt (FIG. 4P; FIG. 4Q, panels labeled Q1-Q2) and nearly normalizes the percentage of EphB2$^+$, EphB2$^+$hTERT$^+$ and EphB2$^{hi}$LGR5$^+$ cells in isolated intestinal crypts as compared to baseline (FIGS. 5A-5C). CoSC marker expression (FIGS. 5D-5G) and growth/morphology of mini-guts obtained from SPK individuals were nearly normalized as well (FIG. 5H; FIG. 13A, panels labeled A1-A6). Transcriptome analysis revealed that SPK nearly restored the expression of stem cell and CoSC markers and of pathways involved in preserving CoSCs (FIG. 5I, FIG. 13B, Table VII).

TABLE VII

List of up and down-regulated stem cell target genes identified by transcriptomic profiling in SPK as compared to T1D + ESRD freshly isolated colonic crypts (at least p < 0.05).

| Down-regulated genes | | Up-regulated genes | |
|---|---|---|---|
| DVL1 | ACTC1 | APC | CCND2 |
| WNT1 | BTRC | SOX1 | SOX2 |
| | ACAN | COL1A1 | COL2A1 |
| | BMP3 | | |
| | CCNE1 | CDK1 | |
| | CXCL2 | | |
| | CD8B | MME | |
| | DLL3 | HDAC2 | JAG1 |
| | DTX2 | | |
| | FGF2 | | |
| | GDF3 | ISL1 | MSX1 |
| | MYO1 | | |
| | GJA1 | | |
| | RB1 | h-TERT | |
| | NCA1 | SIGMAR1 | |
| | PDX1 | DHH | BGLA P |

Abbreviations: EGF, epithelial growth factor; FGF, fibroblast growth factor; BMP, bone morphogenetic protein.

It is concluded that treatment of long-standing T1D with SPK promotes restoration of CoSCs.

Treatment of Long-Standing T1D with SPK Restores Circulating IGF-I and IGFBP3

Figure 5J:
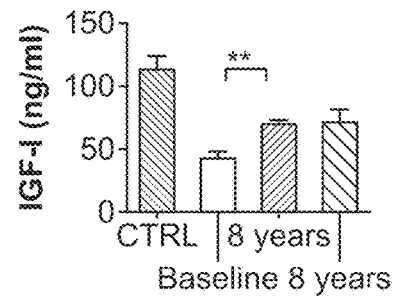
Figure 5K:
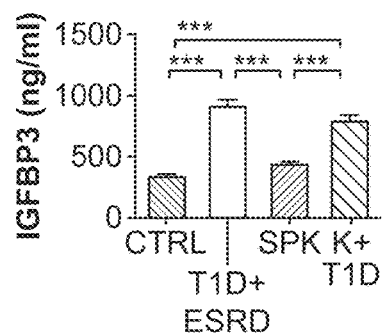
Figure 5L:
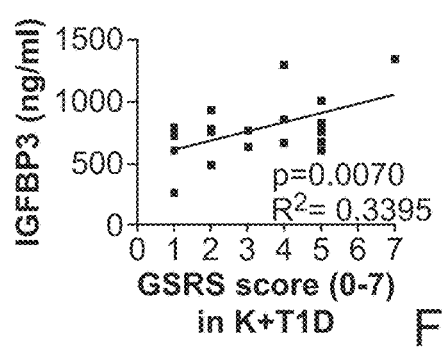
Figure 5M:
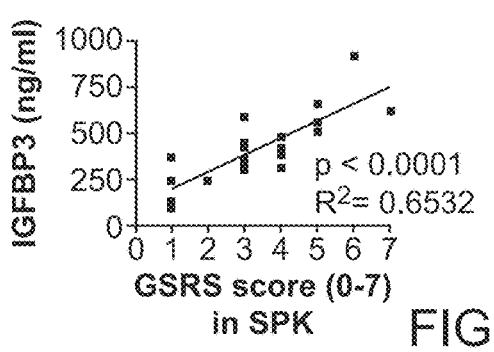
Figure 13C:
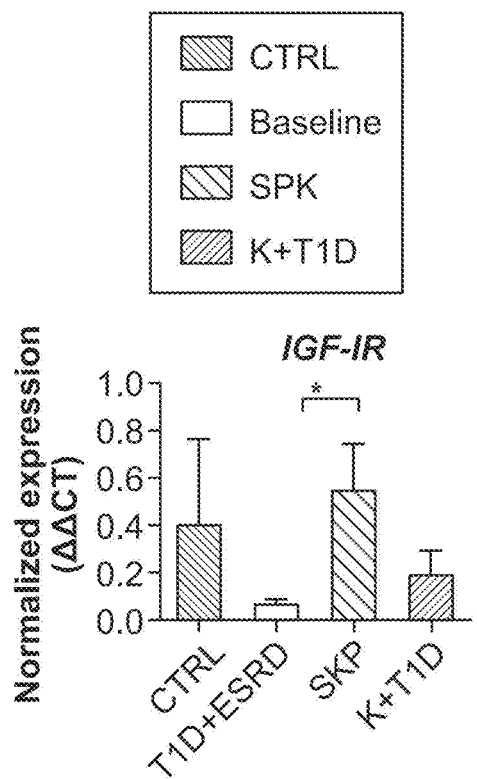
Figure 13D:
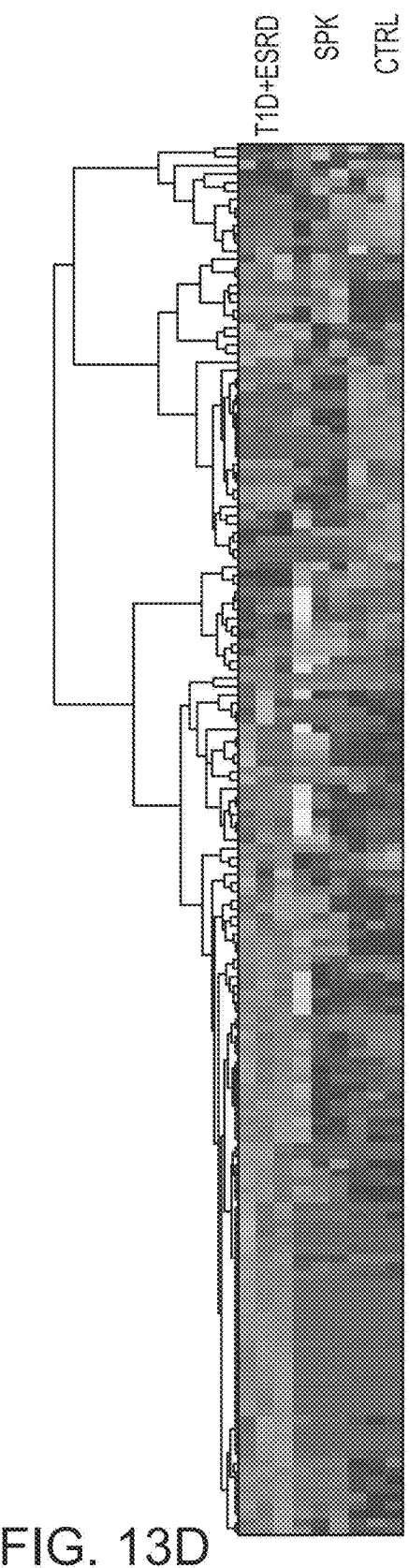
Figure 14A:
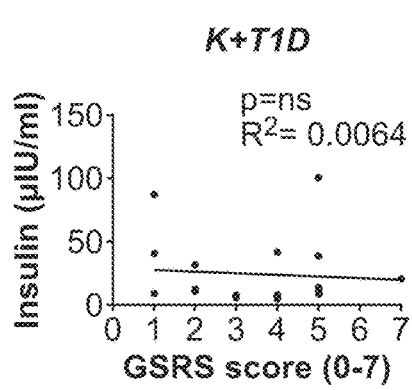
FIGS. 14A-14G. Correlation of intestinal symptoms with levels of insulin, HbA1C and blood glucose in SPK and K+T1D groups.
Figure 14B:
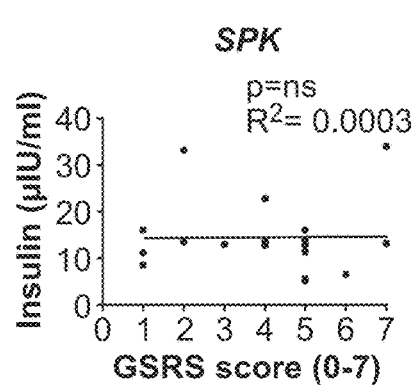
Figure 14C:
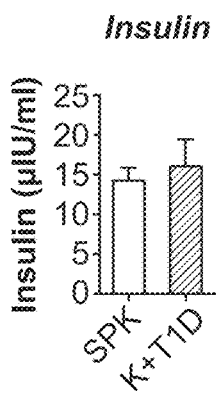
Figure 14D:
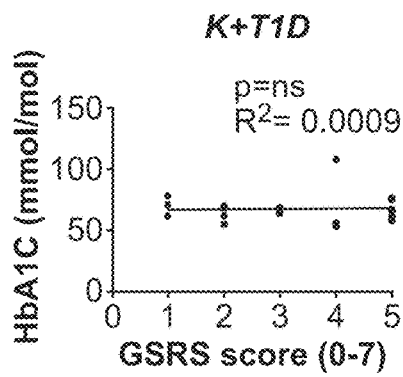
Figure 14E:
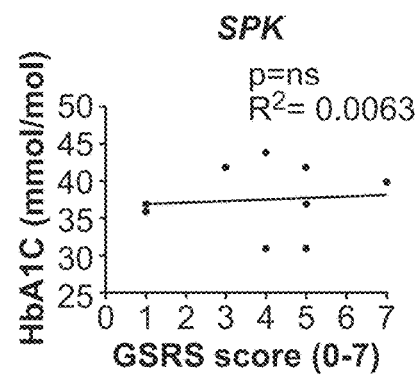
Figure 14F:
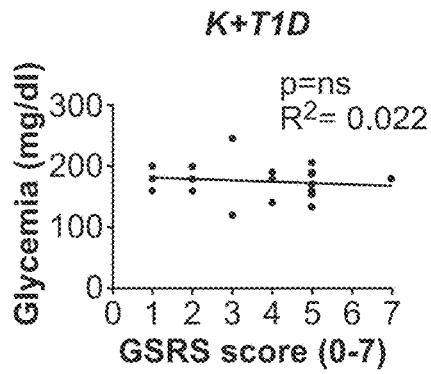
Figure 14G:
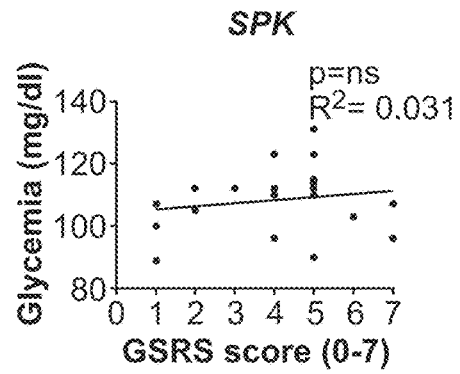

Broad proteomic analysis and targeted immunoassay, revealed a near-normalization of IGFBP3 and IGF-I serum levels after SPK (FIGS. 5J-5K) in association with a nearly re-established expression of IGF-IR (FIG. 13C). These results were not evident in the K+T1D group, who showed low levels of IGF-I (FIG. 5J) and IGF-IR expression (FIG. 13C) and only a partial recovery in their IGFBP profile (FIG. 13D). A significant correlation between IGFBP3 serum levels and intestinal symptoms in both SPK and K+T1D groups, but more evident in the latter, confirmed that the restoration of IGFBP3 levels is associated with an improvement in diabetic enteropathy (FIGS. 5L-5M, FIGS. 14A-14G). Treatment of long-standing T1D with SPK ameliorates diabetic enteropathy via a glucose-associated restoration of the circulating IGF-I/IGFBP3 dyad.

The Ecto-TMEM219 Recombinant Protein Abrogates IGFBP3-Mediated Mini-Gut Destruction In Vitro and Preserves CoSCs In Vivo in a Murine Model of DE.

In order to further demonstrate the IGFBP3-mediated detrimental effects on CoSCs, the inventors generated a recombinant protein based on the TMEM219 extracellular domain (ecto-TMEM219). Addition of ecto-TMEM219 (2:1 molar ratio with IGFBP3) to crypts obtained from CTRL and cultured with IGFBP3 abrogated the pro-apoptotic effect of IGFBP3 on mini-guts and preserved the regenerative properties of crypts to generate mini-guts (FIG. 6A). The expression of CoSC signature markers, EphB2 and LGR5, significantly recovered in mini-guts cultured with IGFBP3 and ecto-TMEM219, emphasizing a favorable effect in preserving CoSCs (FIG. 6B), which was also confirmed in high glucose-cultured mini-guts (FIG. 6A). Moreover, Analysis of Caspase 8 and 9 by RT-PCR documented a net decrease in their expression when ecto-TMEM219 was added to IGFBP3-cultured mini-guts as compared to IGFBP3 alone (FIGS. 6C-6D). The inventors then treated STZ-B6 mice with ecto-TMEM219 and observed improved mucosa morphology with recovered number, depth and width of crypts (FIGS. 6E-6G). Administration of ecto-TMEM219 was associated with an increase in mice body weight as compared to STZ-treated B6 (FIG. 6H), with significant regain of CoSCs (FIGS. 6I-6K), a decreased expression of caspase 8 and 9 (FIGS. 6L-6M) and a re-establishment of circulating IGFBP3 levels (FIG. 6N).

DISCUSSION

Diabetic enteropathy represents a clinically relevant complication in individuals with T1D, as it is associated with lower quality of life, malnutrition and malabsorbtion (Bytzer et al., 2002; Faraj et al., 2007; Talley et al., 2001). Particularly, in individuals with long-standing T1D (T1D+ESRD), intestinal disorders occur with high frequency and severity (Cano et al., 2007; Wu et al., 2004), resulting in body mass loss and cachexia (Pupim et al., 2005), indicating that enteropathy is an important complication of long-standing T1D (Atkinson et al., 2013; Pambianco et al., 2006). Inventors' results demonstrate that individuals with long-standing T1D experienced severe intestinal disorders (Table VIII) and that these clinical conditions are associated with alterations of the intestinal mucosa, with reduced proliferation of intestinal epithelial cells and with signs of neural degeneration.

Similar features have also been reported in rodent models of T1D and DE (Domenech et al., 2011). Inventors' data, for the first time, link DE to a defect in CoSCs and implicate IGFBP3 as having an important role in the maintenance of intestinal epithelium homeostasis. While hyperglycemia is a prominent feature of T1D, inventors' in vitro studies suggest that this feature cannot fully explain DE and that circulating factors may play an important role. Proteomic analysis led to the identification of IGF-I as an enterotrophic factor involved in the homeostasis of CoSCs. The inventors then confirmed that IGF-I and IGFBP3 control CoSCs and that this axis is dysfunctional in long-standing T1D. Inventors' data indicate that IGF-I acts as a circulating enterotrophic factor that promotes crypt growth and controls CoSCs through IGF-IR, while IGFBP3 can block IGF-I signaling by binding circulating IGF-I and reducing its bioavailability.

In addition, and most importantly, the inventors showed that IGFBP3 acts through a pro-apoptotic IGF-I-independent mechanism on CoSCs, which the inventors demonstrated express TMEM219 (the IGFBP3 receptor), thereby inducing the failure of mini-gut growth. This latter effect is Caspase 8 and 9-mediated and TMEM219-dependent; indeed, the absence of the IGFBP3 receptor (TMEM219) on CoSCs greatly diminished high glucose-associated CoSC injuries. T1D together with starvation and cachexia are characterized by low circulating IGF-I levels (Bondy et al., 1994; Giustina et al., 2014) due to reduced hepatic IGF-I release, which is controlled and stimulated by endogenous insulin (Le Roith, 1997; Sridhar and Goodwin, 2009). More importantly, hyperglycemia appeared to have a direct effect on hepatic synthesis and release of IGFBP3. IGFBP3 may thus act as a hepatic hormone that reduces intestinal absorptive capacity during hyperglycemia. Interestingly, SPK provided a proof of concept to the inventors' hypothesis and supported their findings regarding the existence of circulating factors that control CoSCs. The striking improvement of clinical and functional features of DE that the inventors observed in their study, associated with replenishment of the CoSCs and with restoration of the circulating IGF-I and IGFBP3, strengthens inventors' hypothesis. Finally, the

TABLE VIII

Overview of results of diabetic enteropathy assessment in T1D + ESRD individuals as compared to CTRL and SPK.

|  | Results | T1D + ESRD vs. CTRL | SPK±vs. T1D + ESRD |
|---|---|---|---|
| Metabolic Evaluation | Glucose metabolism | --- | +++ |
|  | Lipid metabolism | -- | + |
|  | Blood pressure control | -- | + |
| Intestinal Symptoms | Diarrhea | --- | +++ |
|  | Abdominal pain | --- | +++ |
|  | Constipation | --- | ++ |
| Anorectal Manometry | Resting tone | = | = |
|  | Contracting tone | -- | = |
|  | Reflex response | -- | = |
|  | Urgency volume | -- | ++ |
| Mucosa Epithelial Renewal | Proliferation | --- | +++ |
|  | Differentiation | --- | +++ |
| Neural Regeneration | Nerves | --- | +++ |
|  | Schwann cells | --- | +++ |
| Colonic Stem Cell Turnover | Colonic stem cells | --- | +++ |
|  | Crypt growth | --- | +++ |

Arbitrary unit: +++ (high improvement); ++ (mild improvement); + (slight improvement); = no improvement; --- (severe worsening); -- (mild worsening), - (slight worsening).
Evaluations were performed as follows: T1D + ESRD vs. CTRL, SKP vs. T1D + ESRD, K + T1D vs. SKP.
Abbreviations; T1D, type 1 diabetes; ESRD, end stage renal disease; CTRL, healthy subjects; SPK, simultaneous kidney-pancreas transplantation.

newly generated ecto-TMEM219 recombinant protein improved DE in diabetic mice in vivo and restored the ability of mini-guts to grow normally in vitro, thus confirming the role of IGFBP3 in controlling CoSCs and paving the way for a novel potential therapeutic strategy. In summary, inventors' study shows that an IGFBP3-mediated disruption of CoSCs linked to hyperglycemia is evident in DE. The inventors suggest that circulating IGF-I/IGFBP3 represent a hormonal dyad that controls CoSCs and a novel therapeutic target for individuals with intestinal disorders, in particular caused by diabetes mellitus of long duration (Bondy et al., 1994; Bortvedt and Lund, 2012; Boucher et al., 2010).

Example 2

Materials and Methods
Patients and Study Design 60 individuals with T1D+ESRD registered on the waiting list for simultaneous pancreas-kidney transplantation (SPK) matched for (age 41 to 43 years old), gender, and duration of T1D (29.4±1.8 years) were enrolled in the study. 20 subjects affected by type 1 diabetes (T1D) from 10 to 20 years were enrolled as well. 20 healthy subjects matched for age and gender (CTRL), with normal renal function and normal glycometabolic parameters, were studied as well. T1D+ESRD subjects were all on intensive insulin treatment at the time of enrollment in the study, while the CTRL group was not being administered any medication. All T1D+ESRD subjects were on the same treatment as antiplatelet therapy (ASA) and anti-hypertension (angiotensin-converting-enzyme inhibitors), while 40 out of 60 received statins when enrolled in the study. Subjects with clear signs of inflammatory bowel diseases as well as celiac disease were not enrolled.

T1D+ESRD individuals were followed up for 8 years (mean follow-up: 8.6±1.1 years) after receiving either SPK (n=30) or K+T1D (n=30) transplantation according to the macroscopic surgical evaluation at the time of transplantation. Individuals taking an oral anticoagulant agent were not included. SPK individuals were all insulin-independent for the entire follow-up period, whereas K+T1D individuals were on intensive subcutaneous insulin therapy. All subjects provided informed consent before study enrollment. Studies not included in the routine clinical follow-up were covered by an appropriate Institutional Review Board approval (Enteropatia-trapianto/01 Secchi/Fiorina).

IGFBP3 Assessment in Urine and Serum

Serum was collected from 3 ml of fresh blood after centrifugation. Urine samples were collected fresh, centrifuged and stored at −80° C. IGFBP3 levels of all groups of subjects were assessed in frozen samples of serum and urine using commercially available ELISA kits, according to the manufacturer's instructions (R&D).

Statistical Analysis

Correlation analysis and graphs were performed using Prism Graphpad software. Correlation analysis included assessment of IGFBP3 levels in serum vs. urine of individuals evaluated, IGFBP3 serum levels vs. estimated glomerular filtration rate (eGFR). Statistical significance was considered when p value was <0.05.

Measurement of Renal Function and Glycometabolic Parameters

MDRD formula was used to assess estimated glomerular filtration rate (eGFR) in ml/min/m2. Blood tests included assessment of Creatinine, blood glucose, glycated hemoglobin in all subjects enrolled in the study focusing on comparing CTRL with T1D individuals and individuals with longstanding T1D (T1D+ESRD).

Results

Serum IGFBP3 Levels Correlates with Urinary IGFBP3 Levels

Figure 7A:
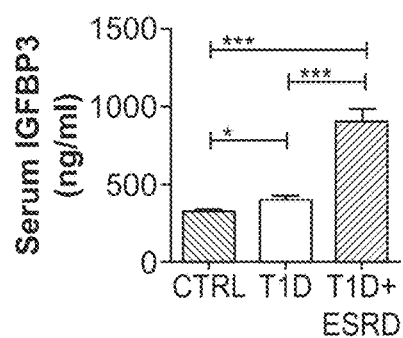
FIGS. 7A-7F. Assessment of IGFBP3 levels in serum (FIG. 7A) and urine (FIG. 7B) of CTRL, T1D and T1D+ESRD individuals.
Figure 7B:
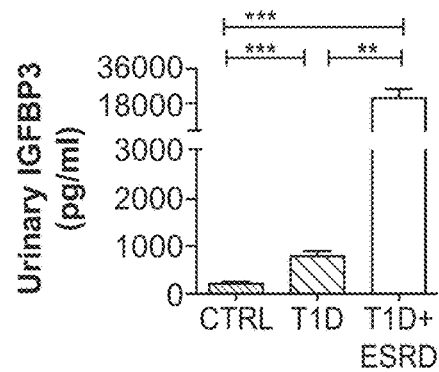
Figure 7C:
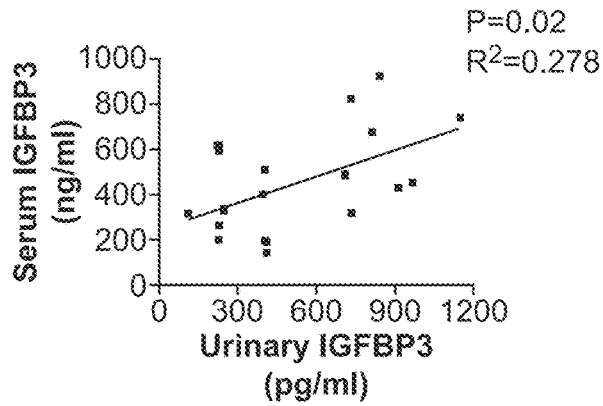
Figure 7D:
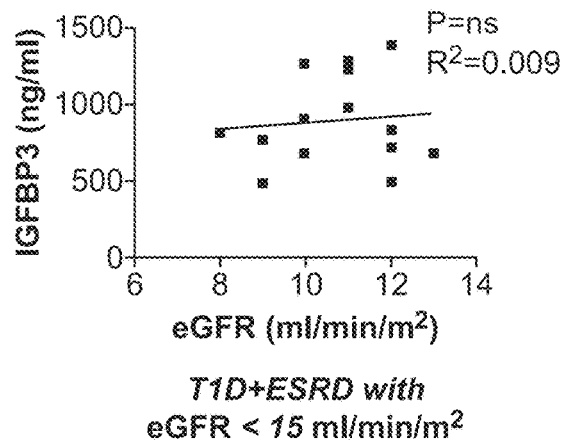
Figure 7E:
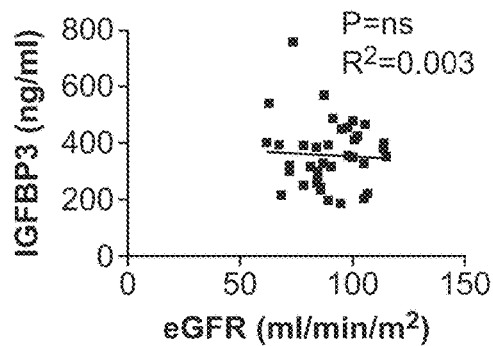

Analysis of serum and urine levels of IGFBP3 in all subjects enrolled in the study documented a significant increase of both serum (FIG. 7A) and urine (FIG. 7B) levels of IGFBP3 in T1D+ESRD subjects as compared to CTRL and to a lesser extent to T1D individuals. A significant correlation between urine levels and serum levels of IGFBP3 was observed in all subjects evaluated (FIG. 7C). Higher levels of serum IGFBP3 correlate with higher levels of urinary IGFBP3. In order to exclude that this might be related to renal function, a correlation between IGFBP3 serum levels and renal function (eGFR) was performed. IGFBP3 serum levels were significantly higher in subjects with ESRD (eGFR<15 ml/min/m2) (FIG. 7D). However, subjects with an eGFR>15 ml/min/m2, thus not affected by ESRD, regardless the presence and history of T1D, did not show any statistical significant correlation between eGFR and IGFBP3 serum levels (FIG. 7E). Considering the correlation between IGFBP3 urinary vs. serum levels in CTRL and comparing their means and medians values within the 25° and 75° percentiles, inventors may set up a range for urinary IGFBP3 as following:

<350 pg/ml: normal levels (levels observed in healthy subjects)
350-500 pg/ml: altered levels (levels observed in T1D with a history of disease<5 years)
>500 pg/ml: indicative of enteropathy (levels observed in long-standing T1D, T1D subjects with other T1D complications, history of T1D>5 years).

Figure 7F:
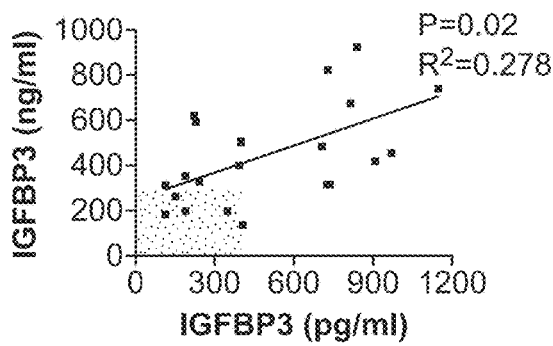

The inventors can also identify a normal range of urinary IGFBP3 levels (<350 pg/ml) by considering its correlation with serum IGFBP3 levels as represented in the gray area in FIG. 7F.

Example 3

Five individuals with long-term (>5 years) inflammatory bowel disease (IBD) were enrolled and screened for peripheral levels of IGFBP3, IGF-I and the ratio of the IGFBP-3/IGF-I, according to the same method described above for the analysis of diabetic samples.

Figure 18:
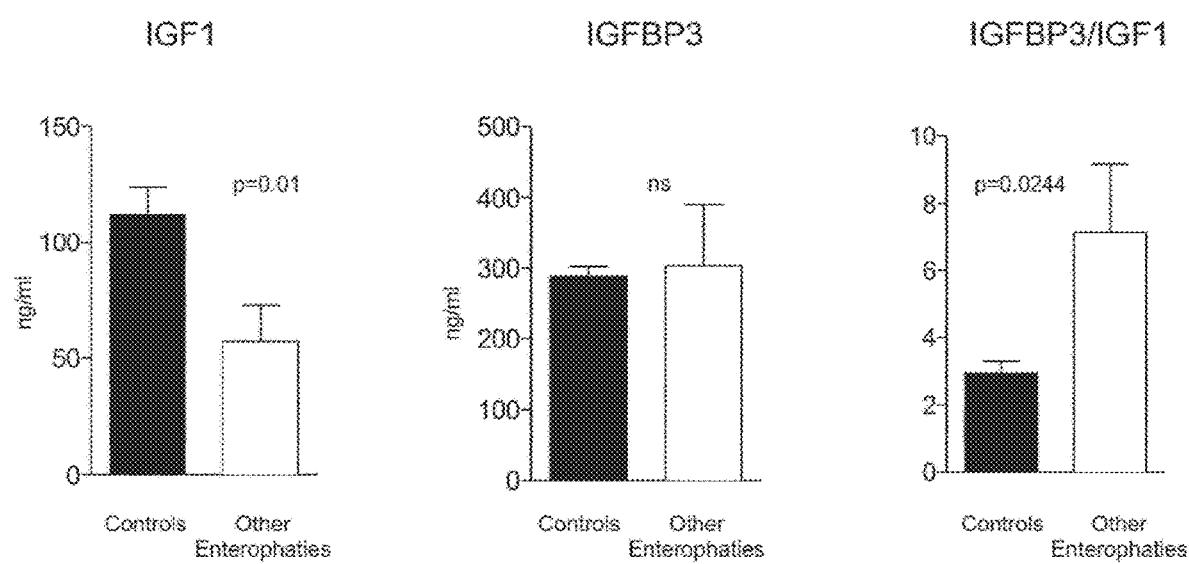
FIG. 18. Peripheral IGFBP3 levels are increased in individuals with inflammatory bowel disease as compared to healthy subjects.

It was found that while IGFBP3 was slightly increased, the levels of IGFI were severely reduced with an overall alteration of IGFBP3/IGF1 ratio (FIG. 18). Thus in inflammatory bowel disease, a large amount of IGFBP3 is free and available to exert its toxic effect on the intestinal stem cells. Consequently, an inhibitor of IGFBP3 is also beneficial for the treatment and/or prevention of inflammatory bowel diseases.

REFERENCES

The Diabetes Control and Complications Trial Res. Group (1993). N Engl J Med 329, 977-986.
Atkinson, M. A. (2013). Type 1 diabetes. Lancet 383, 69-82.
Barker, N. (2014). Nat Rev Mol Cell Biol 15, 19-33.
Baxter, R. C. (2013). J Cell Commun Signal 7, 179-189.
Bondy, C. A., et al., (1994). Ann Intern Med 120, 593-601
Bortvedt, S. F., and Lund, P. K. (2012). Curr Opin Gastroenterol 28, 89-98.
Boucher, J., et al., (2010). Sci Signal 3, ra87.
Breault, D. T., et al., (2008). Proc Natl Acad Sci USA 105, 10420-10425.

Bytzer, P., et al., (2002). Am J Gastroenterol 97, 604-611.
Camilleri, M. (2007). Diabetic gastroparesis. N Engl J Med 356, 820-829.
Cano, A. E., et al., (2007). Am J Gastroenterol 102, 1990-1997.
Carlone, D. L., and Breault, D. T. (2012). Cell Stem Cell 10, 2-4.
Carpentino, J. E., et al., (2009). Cancer Res 69, 8208-8215.
Domenech, A., et al., (2011). Int J Exp Pathol 92, 400-412.
Faraj, J., et al., (2007). Diabet Med 24, 1235-1239.
Feldman, M., and Schiller, L. R. (1983). Ann Intern Med 98, 378-384.
Fiorina, P., et al. (2004). Diabetes 53, 2291-2300.
Fiorina, P., et al. (2001). Diabetes 50, 496-501.
Fiorina, P., et al. (2005). Diabetes Care 28, 1303-1310.
Folli, F., et al. (2010). PLoS One 5, e9923.
Giustina, A., et al., (2014). Acta Diabetol.
Gracz, A. D., et al., (2013). Stem Cells 31, 2024-2030.
Hughes, K. R., Sablitzky, F., and Mahida, Y. R. (2011). Inflamm Bowel Dis 17, 213-220.
Jung, P., et al. (2011). Nat Med 17, 1225-1227.
Le Roith, D. (1997). N Engl J Med 336, 633-640.
Medema, J. P., and Vermeulen, L. (2011). Nature 474, 318-326.
Merlos-Suarez, A., et al. (2011). Cell Stem Cell 8, 511-524.
Munoz, J., et al. (2012). EMBO J 31, 3079-3091.
Pambianco, G., et al., (2006). Diabetes 55, 1463-1469.
Pupim, L. B., et al., (2005). Kidney Int 68, 2368-2374.
Sato, T., and Clevers, H. (2013). Science 340, 1190-1194.
Secchi, A., et al., (1998). Lancet 352, 65; author reply 66.
Smets, Y. F., et al., (1999). Lancet 353, 1915-1919.
Sridhar, S. S., and Goodwin, P. J. (2009). J Clin Oncol 27, 165-167.
Stange, D. E., and Clevers, H. (2013). Stem Cells 31, 2287-2295.
Talley, N. J., et al., (2001). Am J Gastroenterol 96, 71-76.
van der Flier, L. G., and Clevers, H. (2009). Annual review of physiology 71, 241-260.
Williams, A. C., et al., (2007). Cell Death Differ 14, 137-145.
Wu, M. J., et al., (2004). Am J Kidney Dis 44, 322-327.
Zeki, S. S., et al., (2011). Nature reviews. Gastroenterology & hepatology 8, 90-100.
Zhao, J., Yang, J., and Gregersen, H. (2003). Diabetologia 46, 1688-1697.
Ziskin, J. L., et al., (2013). Gut 62, 1012-1023.
Levey, A. S., et al., (1999). Annals of internal medicine 130, 461-470.
Svedlund, J., Sjodin, I., and Dotevall, G. (1988). Digestive diseases and sciences 33, 129-134.
Canington, E. V., et al. (2014). Neurogastroenterology and motility: the official journal of the European Gastrointestinal Motility Society.
Remes-Troche, J. M., et al., (2010). Diseases of the colon and rectum 53, 1047-1054.
Hsu, S. M., Raine, L., and Fanger, H. (1981). The j. of histochem. and cytochemistry: 29, 577-580.
Fiorina, P., et al. (2003). Diabetes care 26, 1129-1136.
Lowry, O. H., et al., (1951). The Journal of biological chemistry 193, 265-275.
Kosinski, C., et al. (2007). PNAS 104, 15418-15423.
Wisniewski, J. R., et al., (2009). Nature methods 6, 359-362.
Cox, J., et al., (2011). Journal of proteome research 10, 1794-1805.
Merlos-Suarez, A., et al. (2011) Cell Stem Cell 8, 511-524.
Gersemann M, Stange E F, Wehkamp J. World journal of gastroenterology 2011; 17:3198-203.
Schonhoff S E, Giel-Moloney M, Leiter A B. Endocrinology 2004; 145:2639-44.
Jung P, Sato T, Merlos-Suarez A, et al. Nature medicine 2011; 17:1225-7.
Merlos-Suarez A, Baniga F M, Jung P, et al. Cell stem cell 2011; 8:511-24.
Piscaglia A C, Rutella S, Laterza L, et al. Journal of translational medicine 2015; 13:220.
Senger S, Sapone A, Fiorentino M R, Mazzarella G, Lauwers G Y, Fasano A. PloS one 2015; 10:e0144634.
Bartfeld S, Bayram T, van de Wetering M, et al. Gastroenterology 2015; 148:126-36 e6.
Boman B M, Huang E. J. of clin. oncol.: official j. of the American Society of Clin. Oncol 2008; 26:2828-38.
D'Addio F, La Rosa S, Maestroni A, et al. Cell stem cell 2015; 17:486-98.
D'Mello S, Trauernicht A, Ryan A, et al. Inflammatory bowel diseases 2012; 18:236-45.
Kundu P, Genander M, Straat K, et al. Science translational medicine 2015; 7:281ra44.

The invention claimed is:

1. A method of treating an intestinal disorder selected from diabetic enteropathy and inflammatory bowel disease in a patient, comprising:
    administering an effective amount of an inhibitor of IGFBP3 to the patient,
    wherein said inhibitor is a fragment of TMEM219, and
    wherein the fragment of TMEM219 comprises the extracellular domain of TMEM219 and is capable of binding IGFBP3.

2. The method of claim 1, wherein the inhibitor is ecto-TMEM219 (SEQ ID NO: 3).

3. The method of claim 2, wherein the intestinal disorder is diabetic enteropathy.

4. The method of claim 2, wherein the intestinal disorder is inflammatory bowel disease.

5. The method of claim 4, wherein the inflammatory bowel disease is Crohn's disease.

6. The method of claim 4, wherein the inflammatory bowel disease is ulcerative colitis.

7. The method of claim 1, wherein the intestinal disorder is diabetic enteropathy.

8. The method of claim 1, wherein the intestinal disorder is inflammatory bowel disease.

9. The method of claim 8, wherein the inflammatory bowel disease is Crohn's disease.

10. The method of claim 8, wherein the inflammatory bowel disease is ulcerative colitis.

* * * * *